(12) United States Patent
Douglas et al.

(10) Patent No.: US 8,367,323 B2
(45) Date of Patent: Feb. 5, 2013

(54) ANALYTICAL METHOD INVOLVING DETECTION OF AN EXCIPLEX

(75) Inventors: Kenneth T. Douglas, Manchester (GB); Elena V. Bichenkova, Manchester (GB); Hannah Savage, Staffordshire (GB); Alireza Sardarian, Shiraz (IR)

(73) Assignee: The University of Manchester, Manchester (GB)

( * ) Notice: Subject to any disclaimer, the term of this patent is extended or adjusted under 35 U.S.C. 154(b) by 1184 days.

(21) Appl. No.: 10/554,266

(22) PCT Filed: Apr. 23, 2004

(86) PCT No.: PCT/GB2004/001803
§ 371 (c)(1),
(2), (4) Date: Oct. 25, 2005

(87) PCT Pub. No.: WO2004/097043
PCT Pub. Date: Nov. 11, 2004

(65) Prior Publication Data
US 2006/0263782 A1    Nov. 23, 2006

(30) Foreign Application Priority Data

Apr. 25, 2003  (GB) .................................. 0309396.0

(51) Int. Cl.
*C12Q 1/68* (2006.01)
*G01N 33/00* (2006.01)
*G01J 3/42* (2006.01)
(52) U.S. Cl. ........................... 435/6.1; 436/132; 356/319
(58) Field of Classification Search .................. None
See application file for complete search history.

(56) References Cited

U.S. PATENT DOCUMENTS

| | | | |
|---|---|---|---|
| 6,194,146 B1 | 2/2001 | Utermohlen et al. | |
| 6,218,108 B1 | 4/2001 | Kool | |
| 6,475,730 B1 | 11/2002 | Douglas et al. | |
| 6,902,900 B2 * | 6/2005 | Davies et al. | 435/6 |

FOREIGN PATENT DOCUMENTS

| | | |
|---|---|---|
| EP | 0 810 291 A1 | 12/1997 |
| WO | WO 00/37674 | 6/2000 |
| WO | WO 01/44220 A2 | 6/2001 |
| WO | WO 01/46121 A2 | 6/2001 |
| WO | WO 02/27031 A2 | 4/2002 |
| WO | WO 03/043402 A2 * | 5/2003 |

OTHER PUBLICATIONS

Zeng, et al. Chemistry. Jan. 3, 2003;9(1):282-90.*
Deere, D. et al. Abstract of Letters in applied microbiology 27(6):352-356 (Dec. 1998; abstract available Jan. 1999).*
Lemp, E. et al. Journal of Organic Chemistry 68(8);3009-3016 (Mar. 2003).*

(Continued)

*Primary Examiner* — Diana Johannsen
(74) *Attorney, Agent, or Firm* — Nixon & Vanderhye P.C.

(57) ABSTRACT

The invention relates to the use of an organic solvent selected from 2,2,2-trifluoroethanol, ethylene glycol or ethylene glycol dimethyl ether for enhancing formation, potential formation, fluorescence and/or detection of an exciplex. The invention is applicable particularly to nucleic acid hybridisation assay using two polynucleotide probes that will hybridise to a target nucleic acid. Each probe is labelled with one of two partners capable of forming an exciplex such that, on photoirradiation, the exciplex is formed when the probes are hybridised to the target nucleic acid.

40 Claims, 45 Drawing Sheets

OTHER PUBLICATIONS

Deere, D. et al. Letters in Applied Microbiology 27:352-356 (1998).*
Bichenkova, E.V. et al. Biochem. Biophys. Res. Comm. 332:956-964 (2005).*
National Library of Medicine Medical Subject Heading ("MeSH") for trifluoroethanol, obtained from www.nlm.nih.gov/mesh/MBrowser.html, 2009.*
Vlahovici et al., "A study of the dimethyl 3-benzoyl-5(2'-pyridyl)-indolisine-1, 2-dic arb oxylate exciplexes with alcohols", Journal of Luminescence, vol. 96, No. 2-4, Mar. 2002, pp. 279-285, XP004343727.
Hamada et al., "Synthesis and fluorescent molecular sensing at exciplex emission of pyrene-and cyanobenzene-modified gamma-cyclodestrins", Journal of the Chemical Society, 2001, No. 3, pp. 388-394, XP002296297.
Balon et al., "Hydrogen-bonding and proton transfer interactions between harmane and trifluorethanol in the ground and excited singlet states", Photochemistry and Photobiology, vol. 67, No. 4, Apr. 1998, pp. 414-419, XP009036503.
Morgan et al., "Photochemistry and Photo Physics of Guanine Containing Di Nucleosides", Photochemistry and Photobiology, vol. 29, No. 6, 1979, pp. 1107-1114, XP009036501.
Yamana et al., "2'-Pyrene modified oligonucleotide provides a highly sensitive fluorescent probe of RNA", Nucleic Acids Research, vol. 27, No. 11, Jun. 1, 1999, pp. 2387-2392, XP002246724.
International Search Report issued in connection with PCT/GB2004/001803 dated Sep. 17, 2004.
GB Search Report issued in connection with Appln. No. GB 0309396.0 dated Aug. 28, 2003.
Paris et al, "Probing DNA sequences in solution with a monomer-excimer fluorescence color change", Nucleic Acids Research 26(16):3789-3793 (1998).
Bhattacharya et al, "Exciplex Formation by Anthracene Monosulphonates in Aqueous Solution and the Role of Monaqueous Solvents", J. Indian Chem. Soc. 70:425-431 (1993).

* cited by examiner

SP-1

SP-2

SP-3

SP-4

SP-17

SP-18

SP-19

SP-20

SP-21

SP-23

SP-24

SP-25

SP-26

SP-34

SP-38

3' Attachment of pyrene

3' Attachment of
naphthalene derivative

5' Attachment of pyrene

5' Attachment of naphthalene derivative

3' Attachment of bio-naphthalene derivative.

Melting temperature experiment for SP-19 in Tris buffer/THF system (10 mM Tris, pH 8.3, Na Cl based on 80% TFE/20% water solution).

Comparison of emission spectra of the RNA-BASED SP-19 system with the DNA-Based SP-19 system in 80% TFE? Tris (pH 8.5) at 10°C. Excitation wavelenght 350 nm; slitwidth 5 nm; spectra are scaled to monomer emissions.

Emissions spectra of 5-pyrene-bearing oligo (ON1-5'pyrene) and the full RNA-BASED SP-19 system in Tris buffer at 10°C showing the small background exciplex fluorescence. Excitation wavelenght 350 nm; slidwith 5 nm; spectra are scaled to monomer emission.

Emission spectra of RNA-BASED SP-19 in Tris buffer at various TFE concentrations. All spectra were recorded at 10°C using an excitation wavelenght of 350 nm; slidwidth 5 nm; spectra are scaled to monomer emission.

Emission spectra of the RNA-BASED SP-19 system in 70% TFE/ Tris buffer (component concentration 0.625 μM) showing how exciplex decreases on heating to 40°C and reappears after cooling back to 10°C. Excitation wavelenght 350 nm; slidwith 5nm; spectra are scaled to monomer emission.

melting curve for RNA_SP19. Spectra are recorded in Tris buffer with 72% TFE and scaled to monomer emissions Comparison of Mismatch systems for SP19 exciplex system I before heating.
A=Parent, B=3'mismatch 3, C=3'mismatch 1, D=5'mismatch 3,
E=3'mismatch 2, F=5'mismatch 1, g=5'mismatch 2, H=3'double mismatch,
I=5'double mismatch Comparison of Insertion for SP19 exciplex system I before heating.

Area under the curve for the SP-19 system from 480-600 nm before and after heating to 40 C. Spectra were recorded in 80% TFE/Tris buffer (10mM Tris, 0.1 M NaCl, pH 8.5) at 10 C. Excitation wavelenght 350nm; slidwith 3nm. Spectra are buffer corrected.

Emission Spectra of SP-19 in 80% TFE/ Tris buffer (10 mM Tris, 0.1 M NaCl, pH 8.5) at 10 C in the presence of 1 and 1.5 M betaine. Excitation wavelenght 350nm, slidwith 5nm. Spectra are scaled to monomer emission at 378nm to correct for dilution effects.

Emission spectra showing the effect of 0.15 M and 0.5 M sulfolane on the emission spectra of SP-19 in 80% TFE/ Tris buffer (10 mM Tris, 0.1 M NaCl, pH 8.5) at 10 C. Excitation wavelenght 350nm; slidwith 5 nm. Spectra are scaled to monomer emissions at 379 nm to correct for dilution effects.

Emission spectra of the SP-19 system in 80% TFE/ Tris buffer (10 mM Tris, 0.1 M NaCl, pH 8.5) at 10 C showing the effect of addition of methylsulfone to give 0.6 and 1.1 M solutions. Excitation wavelenght 350 nm; slidwith 5 nm. Spectra are buffer-corrected and scaled to monomer emissions at 379 nm to correct for dilution effects Emission spectra of SP-19 in 80% TFE/ Tris buffer (10 mM Tris, 0.1 M NaCl, pH 8.5) at 10 C showing the effect of the addition of DMSO (to final level of 10%, 1.41 M). Excitation wavelenght 350 nm, slidwith 5 nm. Spectra are buffer-corrected and scaled to monomer emission at 379 nm correct for dilution effects.

SEQUENCE LISTING

<160> NUMBER OF SEQ ID NOS: 12

<210> SEQ ID NO 1
<211> LENGTH: 16
<212> TYPE: DNA
<213> ORGANISM: Artificial Sequence
<220> FEATURE:
<223> OTHER INFORMATION: 16mer nucleic acid target (SP19)

<400> SEQUENCE: 1
gccaaacaca gaatcg                                             16

<210> SEQ ID NO 2
<211> LENGTH: 16
<212> TYPE: RNA
<213> ORGANISM: Artificial Sequence

```
<220> FEATURE:
<223> OTHER INFORMATION: RNA target strand

<400> SEQUENCE: 2
gccaaacaca gaaucg                                                      16

<210> SEQ ID NO 3
<211> LENGTH: 17
<212> TYPE: DNA
<213> ORGANISM: Artificial Sequence
<220> FEATURE:
<223> OTHER INFORMATION: Target DNA sequence containing insertion 1

<400> SEQUENCE: 3
gccaaacagc agaatcg                                                     17

<210> SEQ ID NO 4
<211> LENGTH: 18
<212> TYPE: DNA
<213> ORGANISM: Artificial Sequence
<220> FEATURE:
<223> OTHER INFORMATION: Target DNA sequence containing insertion 2

<400> SEQUENCE: 4
gccaaacagt cagaatcg                                                    18

<210> SEQ ID NO 5
<211> LENGTH: 16
<212> TYPE: DNA
<213> ORGANISM: Artificial Sequence
<220> FEATURE:
<223> OTHER INFORMATION: Target DNA containing 3' mismatch 1

<400> SEQUENCE: 5
gccaaacaca gaatag                                                      16

<210> SEQ ID NO 6
<211> LENGTH: 16
<212> TYPE: DNA
<213> ORGANISM: Artificial Sequence
<220> FEATURE:
<223> OTHER INFORMATION: Target DNA containing 3' mismatch 2

<400> SEQUENCE: 6
gccaaacaca ggatcg                                                      16

<210> SEQ ID NO 7
<211> LENGTH: 16
<212> TYPE: DNA
<213> ORGANISM: Artificial Sequence
<220> FEATURE:
<223> OTHER INFORMATION: Target DNA containing 3' mismatch 3

<400> SEQUENCE: 7
gccaaacaaa gaatcg                                                      16

<210> SEQ ID NO 8
<211> LENGTH: 16
<212> TYPE: DNA
<213> ORGANISM: Artificial Sequence
<220> FEATURE:
<223> OTHER INFORMATION: Target DNA containing 3' double mismatch

<400> SEQUENCE: 8
gccaaacaca ggatgg                                                      16
```

```
<210> SEQ ID NO 9
<211> LENGTH: 16
<212> TYPE: DNA
<213> ORGANISM: Artificial Sequence
<220> FEATURE:
<223> OTHER INFORMATION: Target DNA containing 5' mismatch 1

<400> SEQUENCE: 9
gacaaacaca gaatcg                                                     16

<210> SEQ ID NO 10
<211> LENGTH: 16
<212> TYPE: DNA
<213> ORGANISM: Artificial Sequence
<220> FEATURE:
<223> OTHER INFORMATION: Target DNA containing 5' mismatch 2

<400> SEQUENCE: 10
gccagacaca gaatcg                                                     16

<210> SEQ ID NO 11
<211> LENGTH: 16
<212> TYPE: DNA
<213> ORGANISM: Artificial Sequence
<220> FEATURE:
<223> OTHER INFORMATION: Target DNA containing 5' mismatch 3

<400> SEQUENCE: 11
gccaaactca gaatcg                                                     16

<210> SEQ ID NO 12
<211> LENGTH: 16
<212> TYPE: DNA
<213> ORGANISM: Artificial Sequence
<220> FEATURE:
<223> OTHER INFORMATION: Target DNA containing 5' double mismatch

<400> SEQUENCE: 12
gacagacaca gaatcg                                                     16
```

ANALYTICAL METHOD INVOLVING DETECTION OF AN EXCIPLEX

This application is the U.S. national phase of international application PCT/GB2004/001803, filed 23 Apr. 2004, which designated the U.S. and claims priority of GB 0309396.0, filed 25 Apr. 2003, the entire contents of each of which are hereby incorporated by reference.

The present invention relates to exciplexes and more particularly to enhancing the formation (or potential formation) and/or detectability thereof particularly (but not necessarily exclusively) for the purposes of improved detection in analytical methods such as nucleic acid hybridisation assays.

An exciplex is an excited state, fluorescent complex formed when different fluorescent donor and acceptor species (e.g. pyrene and dimethylaniline) come into the correct positional relationship relative to each other (usually within 4 nm of each other) and photoirradiated (e.g. by a laser) at the wavelength at which one of the individual fluorescent partners absorbs. More particularly, an exciplex is formed between the electronically excited donor and the acceptor in a process which may be represented by the equation:

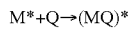

$$M^* + Q \rightarrow (MQ)^*$$

where M* indicates the electronically excited monomer (donor) and Q indicates what is, in effect, a quencher of M* (the acceptor).

The exciplex complex dissociates with emission of fluorescence which is detectably different from the emission of either of the individual exciplex-forming partners. Exciplexes have a red-shifted emission maximum relative to that of either the individual partners from which they are formed (as well as differing in other fluorescent properties) and are therefore detectably different from the individual partners. They also differ in other properties (see, for example, A. Gilbert and J. Baggott, "Essentials of Molecular Photochemistry", published (1991) by Blackwell, Oxford and also Organic Molecular Photophysics, ed J. B. Birks, Wiley, London, Vol 1 (1973), Vol 2 (1975).

Exciplexes are to be distinguished from excimers which are excited state complexes formed when two identical complex forming fluorescent partners (e.g. pyrene) are brought into the correct positional relationship (again within approximately 4 nm of each other) and are photoirradiated at the wavelength at which the individual partners absorb. The formation of an excimer may be represented by the equation:

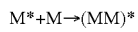

$$M^* + M \rightarrow (MM)^*$$

Once again excimers have a red-shifted emission maximum relative to that of the individual partners from which they are formed. In contrast to excimer emission, exciplex emission is very sensitive to the polarity of the solvent in which the exciplex is formed. Additionally, the exciplex emission maxima and intensities are sensitive to the reduction-oxidation properties of the components. Thus there is the difference between excimers and exciplexes in that, in the case of the latter, there is a degree of charge transfer between the acceptor and donor species due to their difference in redox properties.

Excimers and exciplexes have been proposed for use in various analytical methods.

Thus, for example, excimers and exciplexes have been proposed for use in a method of determining the presence (or otherwise) and/or amount of a target nucleic acid in a biological sample. The method is based on the hybridisation of the target (NA) molecule with two (or more) oligonucleotides, ON1 and ON2, bearing excimer or exciplex partner moieties (e.g. chromophoric labelling groups) at their 5'-terminus and 3'-terminus, respectively, and being complementary to the neighbouring base-pairing sites of the target NA. Thus, under hybridising conditions, the two oligonucleotides are capable of hybridising to the target sequence (if present) such that the 5' terminal nucleotide of the first probe and the 3' terminal nucleotide of the second probe are hybridised to adjacent bases of the target sequence.

The 5' or 3' individual excimer or exciplex partner moieties R1 or R2 are each capable on photoirradiation of forming with the other moiety either an exciplex or an excimer (depending on the nature of the partner moieties) if the two partner moieties are brought into excited complex or excimer forming relationship and this only occurs if both oligonucleotide probes are hybridised to the target sequence. Thus by monitoring of fluorescence at the emission wavelength for the excimer/exciplex, it is possible to determine whether or not the particular polynucleotide target is present (since fluorescence at the emission wavelength of the complex will only be observed if the two probes are correctly hybridised to the target).

It is also possible to use such a method for determining whether or not a target nucleic acid has a point mutation or an insertion, gap etc since the probes may be such that they will bind to the target nucleic acid but the excimer or exciplex signal does not arise or arises with a different level of intensity if the mutation is or is not present (depending on how the assay is "set up"). Furthermore the technique may employ a plurality of pairs of probes as described each of which, if hybridised to the appropriate target sequence, will result in production of a complex having a different fluorescence emission so that by detecting for these different wavelengths the analysis procedure is capable of detecting a plurality of different target sequences.

An example of such a technique is disclosed in EP-A-0 810 291 (Ebata) in which the complex is an excimer and the invention is exemplified by excimers. (There is also a reference in EP-A-0 810 291 to the possibility of the complex being an exciplex but no specific details with regard to such a complex are given). Similar subject matter to EP-A-0 810 291 is disclosed in Ebata et al. Photochem. Photobiol. (1995) v 62, pp 836-839 and Ebata et al. Nucl Acids Symp (1995) Series No. 34, pp 187-188) and in P. L. Paris et al. Nucl. Acids Res. 1 (1998), v 26, pp 3789-373.

There are a number of practical differences as between the uses of excimers and exciplexes in analysis techniques. These differences include:

Their solvent sensitivities (excimers are relatively insensitive to solvent, but exciplexes are widely reported not to emit in solvents more polar than acetonitrile, but see below), The direct linear relationship between the emission frequency of the exciplex and the difference in redox potential of the partners A and B: thus the emitted fluorescence wavelength is tunable chemically for exciplexes, but not for excimers. (see Rehm, D; Weller, A *Zeit Phys. Chem* 1970, 695, 183-200).

The range of structures possible for A and B (very broad in principle for exciplexes, but very limited for excimers where A and B are the same and are usually restricted to pyrene, and quite rarely perylene).

Problems arise in the use of exciplexes in the aqueous conditions of hybridisation assays of the type described above. More particularly, whilst excimer emission is relatively solvent independent in terms of several parameters including emitted wavelength and quantum efficiency, exciplex emission is characterised by a very much more marked dependence on solvent nature. Solvent polarity is crucial to the behaviour of exciplexes and intermolecular exciplexes do not emit usually in solvents even as weakly polar as acetonitrile. Exciplex emission in intermolecular situations occurs preferentially in solvents of low polarity (J. Birks, Photophysics of Aromatic Molecules, publ. Wiley and many other sources). For strongly interacting exciplex partners, such as aromatic hydrocarbons with dialkylanilines (the most widely studied family), the exciplex arises from a partial charge-transferred state, which is sufficiently stable in nonpolar solvents to fluoresce. Increased solvent polarity preferentially solvates and stabilises charge separation and at a dielectric constant of approximately 14, the pyrene:diethylaniline pair has an exciplex absorption spectrum identical with the ion pair, pyrene: $PhNEt_2^+$. This behavioural shift has been ascribed to a change in structure for exciplexes going from compact in nonpolar solvents to loose in polar solvents (Verhoeven et al., Chem. Phys. Lett. (1987) 140, 587; Pur Appl, Chem. (1990) 62, 1585; (1993), 65, 1717), polar solvents here referring to polarity of the order of that possessed by acetonitrile.

There are some exciplex systems which are known to emit in solvents as polar as DMSO, 20% aq. acetonitrile (e.g. Lewis & Cohen, J. Phys. Chem. (1994) 98, 10591) or even water (Pal & Ghosh, J. Photochem. Photobiol. A. Chem. (1994) 78, 31), but only under special circumstances:

WO-A-0146121 (The Victoria University of Manchester) discloses compounds which are capable of forming intramolecular exciplexes in water and polar solvents. For certain of the compounds the emission is pH dependent.

The use of exciplexes as compared to excimers has advantages since it is possible by altering the electron affinity and ionisation potential of the contributing partners to "tune" the fluorescence emission characteristics, such as wavelength, of the complex. For example, an exciplex formed from N,N-diethylamine with chrysene emits at ca 420 nm but one formed from N,N-diethylamine with perylene emits at ca 520 nm.

More particularly, the emission characteristics can be tuned in a predictable sense by the fine chemical structures of the partners, for example the emitted light frequency being linearly related to the difference in electron donor/electron acceptor strengths of the partners (see for example D. Rehm, S. Naturforsch (1970) Vol 25a 1442-1447; J. B. Birks "Photophysics of Aromatic Molecules" published by Wiley Interscience, London).

WO-A-0040751 (The Victoria University of Manchester) proposes various solutions to allow the use of exciplexes in nucleic acid hybridisation assays of the type described above. Examples of the solutions proposed in WO-A-0040751 include:

(i) ensuring that the exciplex is formed in a localised region of greater hydrophobicity than the bulk phase of the sample being analysed;
(ii) including in the sample an additive capable of developing an exciplex fluorescent signal;
(iii) the use of magnetism to enhance exciplex emission; and
(iv) at least one of the steps, in either order, of (a) at least partial removal of the relatively polar medium (water) in which the hybridisation assay is effected, and (b) addition of a less polar medium.

With regard to (iv), WO-A-0040751 discloses acetonitrile and methylcyclohexane (and mixtures of the solvents) as examples of the "less polar medium". However methylcyclohexane does not mix with water and only a certain amount of acetonitrile can be added to DNA without destroying its characteristic duplex structure which is required to obtain exciplex emission.

A further example of analytical technique that relies on excimer or exciplex formation for the purposes of detection is the nucleic acid sequencing method disclosed in WO-A-0037674 (The Victoria University of Manchester).

It is an object of the present invention to obviate or mitigate the above mentioned disadvantages.

In its first aspect the present invention provides the use of an organic solvent selected from 2,2,2-trifluoroethanol, ethylene glycol or ethylene glycol dimethyl ether for enhancing formation, potential formation, fluorescence and/or detection of an exciplex.

Without wishing to be bound by theory, the solvent may enhance formation (or potential formation) of an exciplex or may favour a good signal (from an exciplex that would give no or a poor signal) or otherwise facilitate detection of an exciplex.

By the term "potential formation of an exciplex" we mean that the: invention may be applied to techniques where the exciplex will only be formed if a particular condition exists so that in the absence of that condition there is no exciplex formation but this itself provides useful information, for example as to the presence or otherwise of a target molecule. Therefore it is not a pre-condition of the invention that an exciplex is actually formed.

According to a second aspect there is provided a method of analysis involving detection of an exciplex in a medium containing exciplex forming partners, the method comprising photoirradiating the medium at the appropriate wavelength and detecting for formation of an exciplex characterised in that on photoirradiation the medium contains an organic solvent selected from 2,2,2-trifluoroethanol, ethylene glycol or ethylene glycol dimethyl ether.

Again without wishing to be bound by theory, the presence of the solvent in the method of the second aspect of the invention may enhance formation (or potential formation) of an exciplex or may favour a good signal (from an exciplex that would give no or a poor signal) or otherwise facilitate detection of an exciplex.

It should also be understood that the invention extends to the possibility of detecting a condition which results in a loss of exciplex. Thus, for example, the invention may be applied to an assay in which an exciplex can initially form (on photoirradiation) but which can no longer form when a certain condition prevails. In this case a "positive" result of the assay is determined by loss of exciplex signal.

The invention has been based on our finding that, of a wide range of solvents tested, it was only an organic solvent selected from 2,2,2-trifluoroethanol, ethylene glycol and ethylene glycol dimethyl ether, which have the special characteristics of being able to enhance exciplex emission whereas excimer emission was enhanced by a much wider range of solvents, as demonstrated in the data provided in Example 1 below.

It is particularly preferred that the solvent is 2,2,2-trifluoroethanol.

Preferably the formation or potential formation of the exciplex is effected in a liquid medium which contains the exciplex enhancing solvent (i.e. an organic solvent selected from 2,2,2-trifluoroethanol, ethylene glycol or ethylene glycol dimethyl ether) on irradiation. Preferably also the liquid medium comprises more than 50%, more preferably at least 60%, and more preferably at least 70%, by volume of the exciplex enhancing solvent. It is particularly preferred that the liquid medium comprises 60% to 80% by volume of the exciplex enhancing solvent although higher amounts, e.g. 90% or 95% may be used. Most preferably the liquid medium comprises an admixture of water or buffer and the exciplex enhancing solvent, the latter preferably being present in the amounts indicated.

Exciplexes for use in any one of the above aspects of the invention may be as disclosed, for example, by "The Exciplex" (A. Weller; ed M. Gordon and W. R. Ware, Academic Press N.Y. 1975) and Z. Phys. Chem (1970) 69 1983 (D. Rehm and A Welter). There are very many more specific examples in the literature and these include pyrene and an N,N-dialkylamine, perylene and an N,N-dialkylamine, a metalloporphyrin and a nitroaromatic compound (see J. Amer. Chem. Soc. (1971), 93, 7093; (1974), 96, (6349); and between a phthalocyanine and a nitroaromatic (see Inorg. Chem., (1983), 22, 1672).

With regard to the partners for forming an exciplex it is preferred that:
  (i) the donor and acceptor partners preferably have hydrophobicities that are balanced for mutual attraction without being attracted too much to the nucleic acid; and
  (ii) the donor and acceptor have appropriate redox potentials.

There are many collections of redox potentials available in the literature, for example P. Loach in Handbook of Biochemistry and Molecular Biology, $3^{rd}$ edition, Volume I, p 1222 et seq., CRC Press (1976) Boca Raton, ed. G. d. Fasman.

It is particularly preferred that one of the exciplex forming partners is perylene or pyrene. As applied to pyrene as the acceptor, condition (i) will generally apply that a donor having a fused aromatic ring system provides enhanced exciplex emission as compared to one having a single aromatic ring. Thus, in the case of pyrene as the acceptor, the 2-(N'-methyl-N'-naphthalen-1"ylamino)ethylamino (DMN) group as the donor partner will provide enhanced exciplex emission as compared to the 4-(N,N-dimethylamino)phenyl (DMA) group due to the fused ring system of the former. With regard to condition (ii) the 2-(N'-methyl-N'-naphthalen-1"ylamino) ethylamino (DMN) group provides enhanced exciplex emission as compared to the 2-(N'-naphthalen-1"ylamino)ethylamino (MMN) group.

Detection of the exciplex may be by means of wavelength detection. Exciplexes may also be detectable by other spectroscopic methods including circular dichroic spectral effects as has been described for excimer systems (see for example H. Mihara, Y. Tanaka, T Fujimoto, and N. Nishino J. Chem. Soc. Perkin Trans 2 (1995) p1133-1140. Several other methods may be used for detecting the exciplex including polarisation measurements or anisotropy. Exciplex formation may also by confirmed by lifetime measurements.

It is possible for the analysis to be such that more than one type of exciplex may be formed whereby the various types of exciplex are separately detectable to identify particular aspects of the system under investigation. Thus for example the method may involve formation of two or more exciplexes which are detectable in each others presence.

In the case where two or more exciplexes are formed, electromagnetic energy emitted from one exciplex may be transmitted by resonance energy transfer to effect formation and/or detection of another type of exciplex or other fluorescent quencher. Conversely, resonance energy transfer from a flurophore partner may excite an exciplex signal.

The invention is most preferably applied (and this represents a third aspect of the invention) to a method of analysing a sample to determine the presence or otherwise therein of a target polynucleotide sequence, the method comprising (a) treating the sample under hybridising conditions with
  i) a first polynucleotide probe labelled (e.g. at or adjacent to its 5'-end) with a first exciplex partner moiety able on photoirradiation to form an exciplex with a second exciplex partner, and
  (ii) a second polynucleotide probe labelled (e.g. at or adjacent to its 3'-end) with the second exciplex partner moiety, said first and second probes being adapted to bind to mutually exclusive regions of said target sequence such that said moieties are able to form said exciplex which is detectably different from the first and second moieties,
(b) effecting photoirradiation to cause exciplex formation, and
(c) detecting for formation of the exciplex
characterised in that the sample when irradiated contains an organic solvent selected from 2,2,2-trifluoroethanol, ethylene glycol or ethylene glycol dimethyl ether.

The exciplex partner moieties for use in the third aspect (and other aspects) of the invention may be chromophoric moieties.

We have found somewhat surprisingly that the use of the exciplex enhancing solvent (i.e. 2,2 2,-trifluoroethanol, ethylene glycol or ethylene glycol dimethyl ether) in a method as defined in the previous paragraph strongly enhances exciplex formation without significant destabilisation of the nucleic acid duplexes that form as a result of the hybridisation since it is known that B-DNA duplexes in aqueous media are generally destabilised by the addition of a co-solvent. (Ivanov et al, J. Mol. Biol (1974) 87: 817-833; Malenkov et al, FEBS Letters (1975) 51: 38-42). We believe that the exciplex enhancing solvent serves to prevent, reduce or modulate hydrophobic interactions of the individual exciplex partner moieties with the bases and/or grooves or surfaces of either the probes or the target nucleic acid, which interactions seem (in the absence of the enhancing solvent) to "compromise" the mutual interactions required between the exciplex partner moieties to give rise to complex formation on irradiation.

The optimum percentage of the exciplex enhancing solvent will depend on the nature of the probes and the target strands. As discussed more fully below, the target strand may for example be DNA or RNA and the probes may be DNA, RNA, or an analogue or derivative of a nucleic acid (eg LNA or PNA). Thus, for example, combinations such as DNA probes with DNA targets, LNA probes with DNA targets, and DNA probes with RNA targets will have different optimal percentage amounts of the exciplex enhancing solvent. These optimal amounts may however easily be determined by persons skilled in the art. Generally however the concentration of the exciplex enhancing solvent in the hybridisation mixture will be at least 30% and generally at least 40% by volume. An amount of 40% by volume may, for example, be suitable in the case where at least one of the target and/or probe stands comprises LNA. Higher amounts of solvent may however be required in the case where the target and/or probes comprise DNA and/or RNA. Thus, for certain embodiments of the invention, the amount of the exciplex enhancing solvent in the hybridisation mixture will be at least 50%, more preferably at least 60% and even more preferably at least 70% by volume. For certain embodiments, the concentration will typically be 60% to 80% by volume, although amounts up to 99% can be used.

The exciplex enhancing solvent (e.g. 2,2,2-trifluoroethanol) can be added, pre-hybridisation, simultaneously with hybridisation, or post-hybridisation.

The method of the third aspect of the invention is conducted under hybridising conditions to ensure that the oligonucleotide probe would hybridise to the target nucleic acid (if present) to allow exciplex formation. Such hybridisation conditions are well known to those skilled in the art and generally require buffers, concentrations and/or temperature conditions appropriate to the length of the oligonucleotide probes and/or the particular bases present therein.

The target and probe strands may be free in solution but this is not essential. Thus, for example, at least one (but not all) of the target nucleic acid and/or at least one of the probes may be immobilised with there being also at least one of these moieties free in solution. Thus, for example, one of the probes may be immobilised and the target nucleic acid and the other probe may be free in solution. A further possibility is for the target nucleic acid to be immobilised and the probes to be free in solution. Immobilisation may, for example, be on a solid or liquid substrate. Immobilisation can be on a 'chip' (as used for nucleic acid hybridisation analysis), a micro array, a nanoparticle or other surface. Alternatively immobilisation may be on an oil drop.

If necessary, the sample may be heated or otherwise manipulated before the hybridisation so as to destroy any secondary structure.

The method of the third aspect of the invention may be conducted with additives (e.g. at a level of about 1% or more) sometimes employed in PCR reactions, e.g. betaines, sulfolanes, sulfones and sulfoxides, examples of which are shown below:

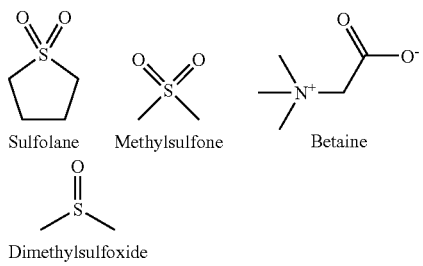

Sulfolane  Methylsulfone  Betaine

Dimethylsulfoxide (Chakrabarti, R.; and Schutt, C. Gene. 2001. 274: 293-298. Diakou, A.; Dovas, C. I. Analytical Biochemistry. 2001. 288: 195-200. Spiess, A. N.; Ivell, R. Analytical Biochemistry. 2002. 301: 168-174. Bachman, B. Luke, W.; Hunsman, G. Nucleic Acids Research. 1990. 18: 1309.)

We have found that such additives can be used in the exciplex systems described herein and can serve to enhance exciplex emission.

In an advantageous development of the third aspect of the invention we have ascertained that an enhancement in exciplex signal is obtained if the hybridisation is conducted at a first temperature, the hybridisation mixture is heated to a second higher temperature, the mixture is then cooled and is then photoirradiated for exciplex formation and detection. Thus for example after initial hybridisation the mixture may be heated to a temperature dependant on the length of duplex and probe oligos and their chemical nature but usually not exceeding 90° C., preferably not exceeding 80° C., preferably less than 70° C. and even more preferably less than 60° C. e.g. 40° C. and then cooled down (e.g. to 5° C., 10° C. or ambient temperature) for photo irradiation and exciplex detection.

In one embodiment of hybridisation assay (i.e. the method of the third aspect of the invention) the first exciplex partner moiety may be attached to the first oligonucleotide probe (e.g. the 5'-terminal end thereof) by means of a linker. Similarly the second exciplex partner moiety may be attached to the second oligonucleotide probe (e.g. to the 3'-terminal end thereof) by a suitable linker.

The linkers may, for example, be of the formula proposed for the linkers in EP-A-0 810 291, namely

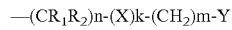

wherein X and Y are independently selected from the group consisting of CONH, NHCO, COO, OCO, O, S, NH and $(PO_3)S$, $R_1$ and $R_2$ are independently selected from hydrogen or a substituent group (eg an alkyl group such as a methyl or ethyl group) and n and m denote an integer of 0 to 5, and k denotes 0 or 1. Preferably at least one of $R_1$ and $R_2$ is hydrogen.

The linkers may for example be a —$CH_2$—CO—NH—$CH_2$—$CH_2$—N(Me)- or a —$CH_2$—CO—NH—$(CH_2)_2$—NH— group.

The linker may be bonded to a phosphate group (e.g. a terminal phosphate group) of the oligonucleotide.

In an alternative embodiment of the hybridisation assay, the first and second exciplex partner moieties may be such as to be nucleic acid base analogues in accordance with the disclosures of U.S. Pat. No. 6,218,018 and WO-A-0144220, both of which were published in the name of Research Corporation, Inc. and name E. T. Kool as inventor. More particularly, the chromophoric moieties (e.g. a polycyclic aromatic hydrocarbon) are each bonded by a carbon-carbon bond to a respective sugar moiety which in turn may be incorporated in (i.e. bonded to) the backbone of the polynucleotide probe.

Alternatively, the exciplex partner moieties may be bonded to a modified sugar or to elsewhere in the molecule (see EP-A-810 291 (Ebata)).

The length of the oligonucleotide probes should be such that there is sufficient "binding affinity" to the nucleic acid that the probes do not become denatured from the target strand as a result of interactions occurring during complex formation and that when both probes are annealed to the target in a contiguous manner a unique stretch of nucleic acid can be reasonably predicted to be sequestered e.g. in a preparation of the genome of a human cell or cells. Generally each oligonucleotide probe (typically a combination of two or more) will comprise at least 6 and preferably up to 9 or even more bases.

The method of the third aspect of the invention may be used qualitatively for detecting the presence of a particular nucleic acid in a sample and/or quantitatively for detecting the amount thereof. In the former case, the presence of a detectable signal demonstrates the macromolecule is present in the sample and in the latter case the level of the signal is representative of the amount of the nucleic acid present.

It is particularly preferred for the third aspect of the invention that the adjacent 3' and 5' ends of the oligonucleotide probes bind to the target nucleic acid with at least one (and preferably no more than three) bases of that target therebetween for the reasons described more fully in WO-A-0040751.

We have in fact found that the characteristics of the exciplex emission obtained in the hybridisation assay are dependent on (i) the number (if any) of base mismatches between, on the one hand, the target nucleic acid and, on the other hand, the probes for hybridisation thereto;

(ii) the nature of any mismatches as referred to in (i);

(iii) whether any mismatch as referred to in (i) is in the region of the 3-probe or 5'-probe;

(iv) the number of bases on the target strands between the adjacent 3' and 5' ends of the probe as hybridised to the target strand;
(v) the nature of the exciplex forming partners; and
(vi) the presence of any variant nucleotides such as RNA or LNA in the target and/or probe strands.

The above characteristics give rise to the feasibility of conducting an assay in which the nature (e.g. intensity) of the exciplex signal is at least indicative and may be determinant of the presence and nature of a mutation (e.g. a point mutation) in a target nucleic acid at a site investigated by the oligonucleotide probes. Put another way, if no mutation is present at the site of the target nucleic acid under investigation then a particular signal will be obtained when the probes are hybridised to the target. If however there is a mutation in the target at the site under investigation then a different signal will be obtained, the characteristic of which will be dependent on the position and nature of the mutation and of any gaps or insertions in the target relative to the 3' and 5' probe oligonucleotides or vice versa. As demonstrated by the data in Example 4 below, the manner in which exciplex emission is dependent on factors (i)-(iii) summarised above is different from excimers.

The method of the third aspect is applicable particularly to the detection of nucleic acids in single stranded form but is also applicable to the detection of nucleic acids in double stranded form of even higher order structure, e.g. triplexes.

The method may be applied to the analysis of nucleic acid having a phosphodiester link in the backbone. Thus the invention is applicable particularly to the analysis of DNA, RNA or a mixed RNA:DNA hybrid as the nucleic acid to be investigated. The method may be applied for the analysis of RNA using DNA oligonucleotide probes or vice versa. The method may be applied to the analysis of nucleic acids (e.g. DNA/RNA) in combination with other molecules such as proteins, and may also be applied to the detection of nucleic acids (e.g. DNA) in chromosomes, chromatin and higher (cellular) structures.

The invention is also applicable to analogues or derivatives of nucleic acids in which the phosphodiester link has been replaced by other species, e.g. phosphodiester link in backbone has been replaced by many things including:
(a) boron structures (see, for example, J S Summers and B R Shaw, Curr Med Chem (2001) 8, 1147-1155);
(b) polyamides, including PNAs (protein or peptide nucleic acid—see, for example, reviews by D A Dean Adv Drug Delivery Res (2000) 44, 81-95; A Ray & B Norden FASEB J (2000) 14, 1041-1060;E Uhlmann, A Peyman, G Breipohl, D W Will Angew. Chem. Int Ed (1998) 37, 2796-2823; H Uhlmann Biol. Chem. (1998) 379, 1045-1052; P E Nielsen Annu Rev Biophys Biomol Struct (1995) 24, 167-183);
(c) others (see, for example, M J J Blommers, U Pieles, A de Mesmaeker Nucl Acids Res (1994) 22, 4187-4194; Z A Shomstein, S Hillers Khim. Geterotsikl. Soedin. (1976), 27-42; D Atkins, M Miller, B de Bouvere, A van Aerschot, P Herdewijn Pharmazie (2000) 55, 615-617)

The invention is also applicable to nucleic acids with modified sugar units, including sugar-replaced "locked nucleic acids" or LNAs (see, for example, H Orum, M H Jakobsen, T Koch, J Vuust, M B Borre Clin Chem (1999) 45, 1898-1905; A A Koshkin, P. Nielsen, M Meldgaard, V K Rajwanshi, S K Singh, J Wengel J Amer Chem Soc (1998) 120, 13252-13253; L Kvaemo J Wengel Chem Commun (1999) 657-658).

We have in fact found that the use of LNAs does have certain characteristics as compared to the target nucleic acids and probes which are based on DNA and/or RNA. In particular, LNA provides a more intense florescence signal and generally does so with a different (lower) amount of exciplex enhancing solvent (e.g. TFE). Additionally, LNA can provide better discrimination in the case of mismatches between the target nucleic acid and the probes.

As applied to the analysis of nucleic acids, the method of invention may be used to detect the presence and/or amount of particular nucleic acid in a sample or may be used to test for the presence of a mutation in nucleic acid (e.g. the probes may be of a sequence such that at least one probe will only bind to the strand if the mutation is present so that no exciplex emission would be observed). The invention may, for example, be aimed at biological exploitation such as detecting specific diagnostic sequences, and with sufficiently sensitive detection, at single cell events such as the real-time formation of recombination sites in DNA, RNA or chromosomes.

Although the invention is particularly applicable to a nuclear hybridisation assay as described more fully above it may be applied to other analytical methods, e.g. a method in which an exciplex is used as a non-radioactive label in a nucleic acid sequencing method for example as disclosed in WO-A-0037674 (The Victoria University of Manchester). The invention may also be employed in the nucleic acid assay disclosed in U.S. Pat. No. 5,332,659 (Kidwell).

BRIEF DESCRIPTION OF THE DRAWINGS

The invention is illustrated by reference to the following Examples and accompanying drawings.

Figure 1A:
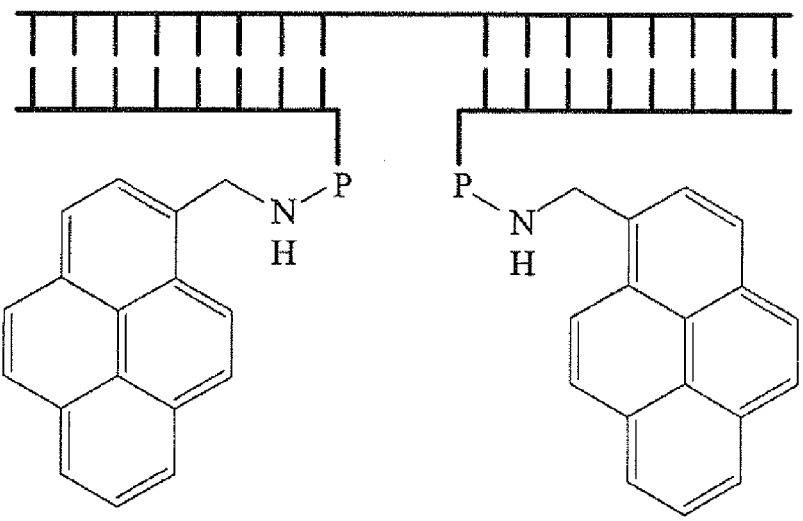
FIGS. 1A-1K illustrate the chemical structures of various hybridisation constructs as investigated in the following Examples. All of the constructs shown in FIG. 1 have the same nucleic acid sequences for the target and probes as set out in Example 1 for SP-1, SP-19 and SP-34.
Figure 1A:
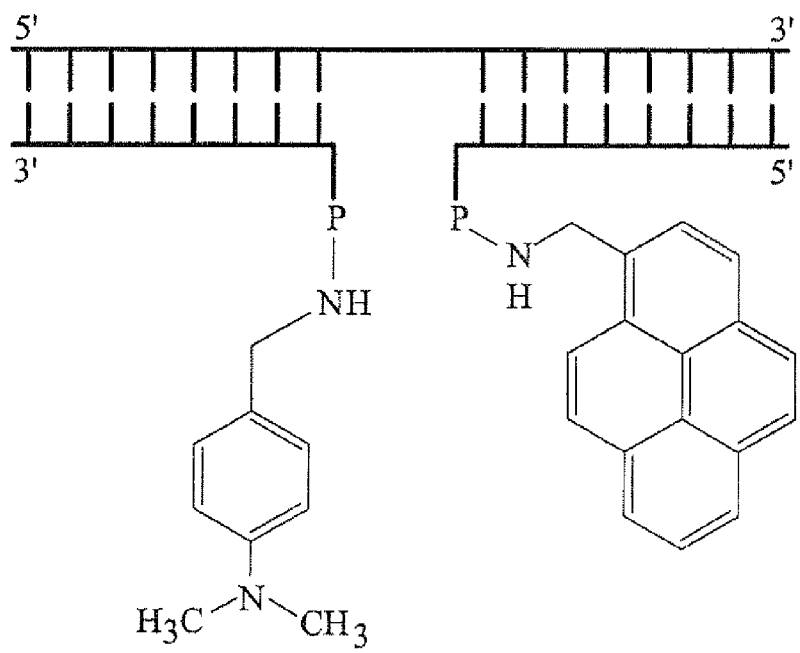
Figure 1B:
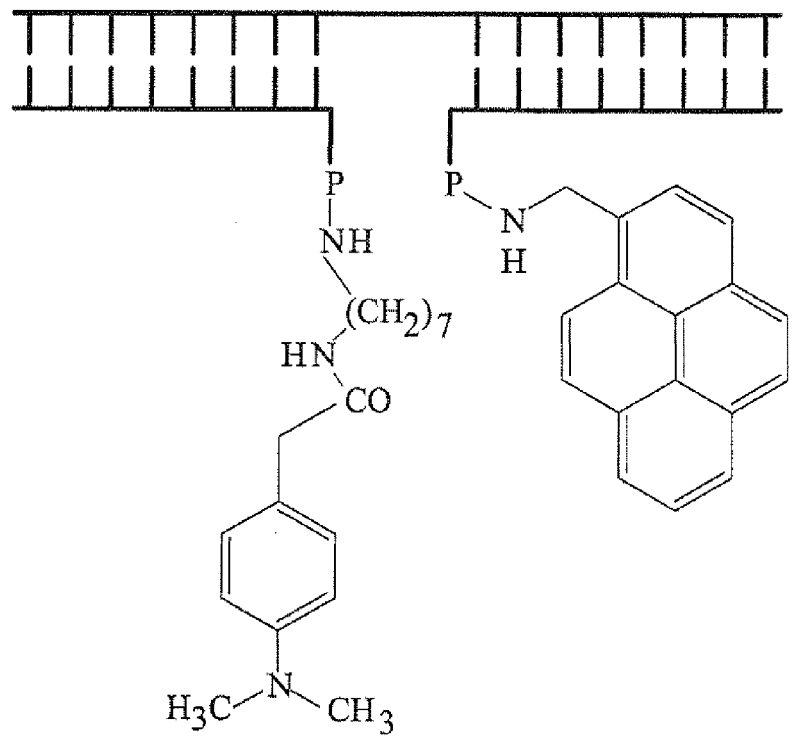
Figure 1B:
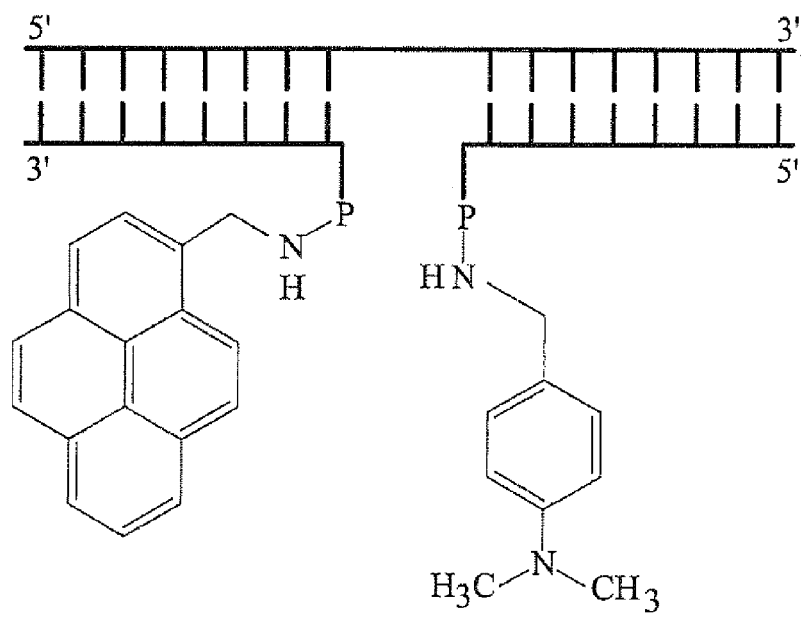
Figure 1C:
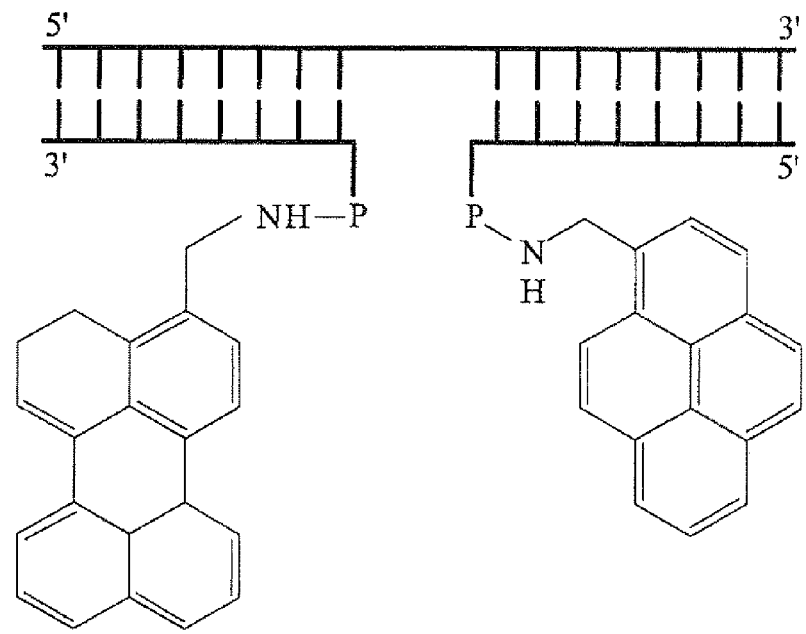
Figure 1C:
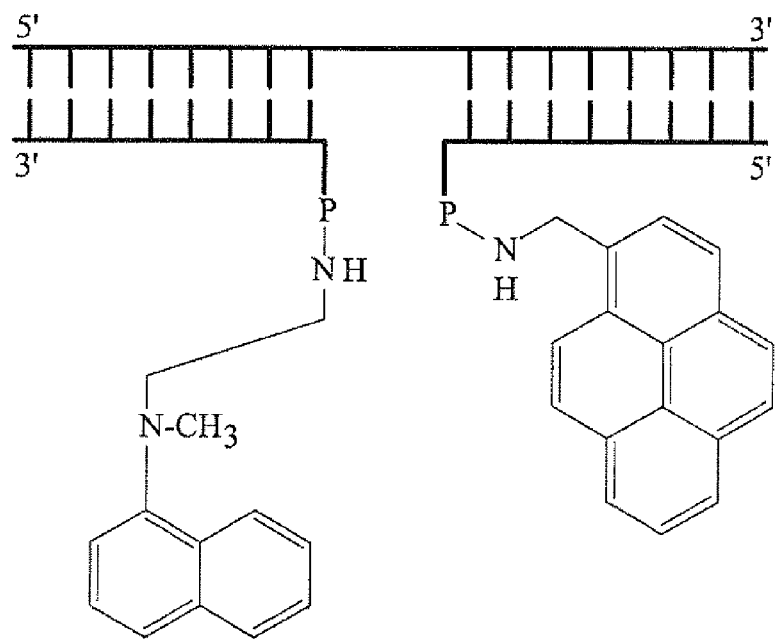
Figure 1D:
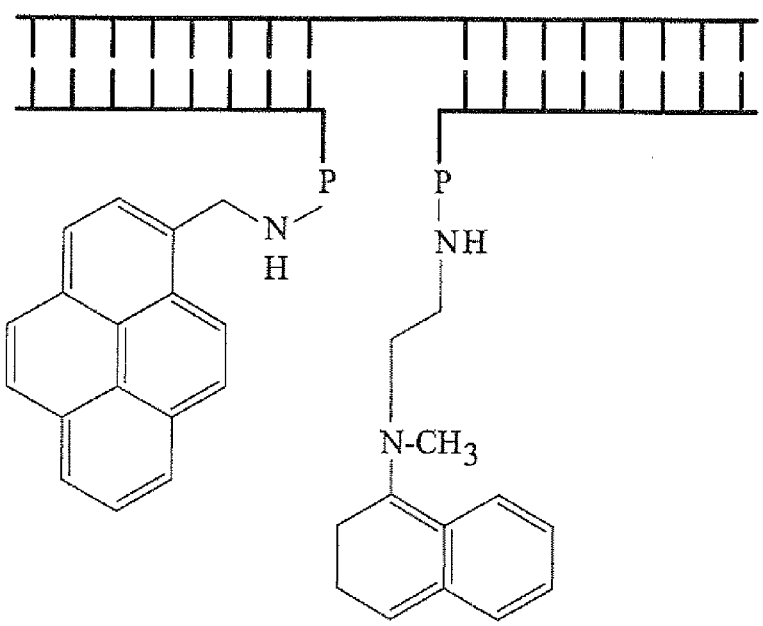
Figure 1D:
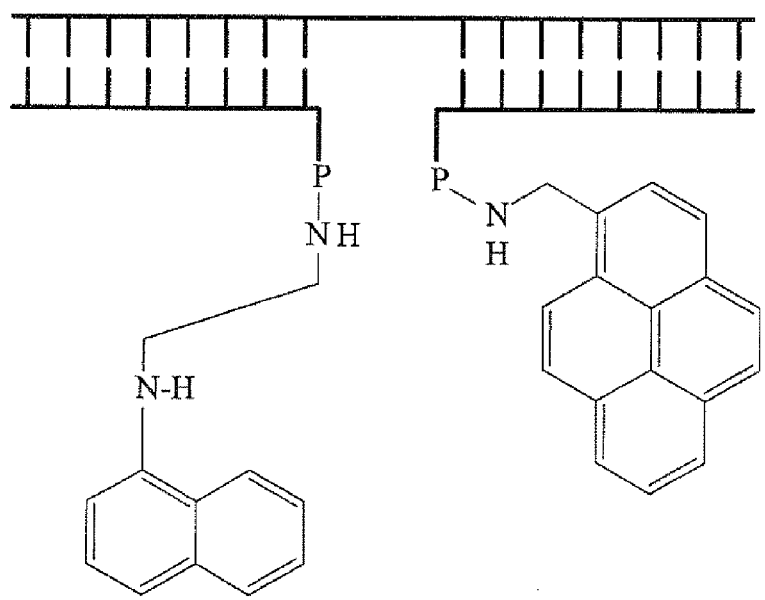
Figure 1E:
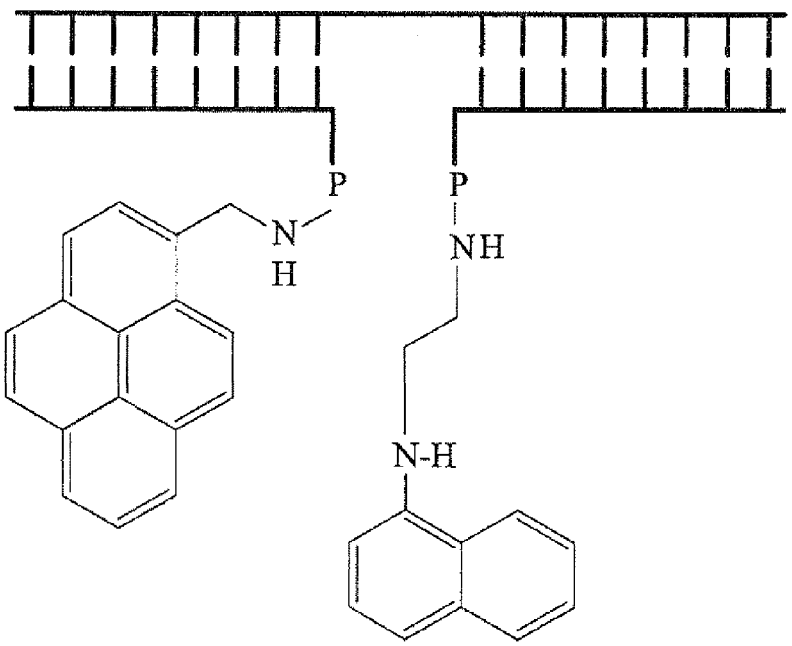
Figure 1E:
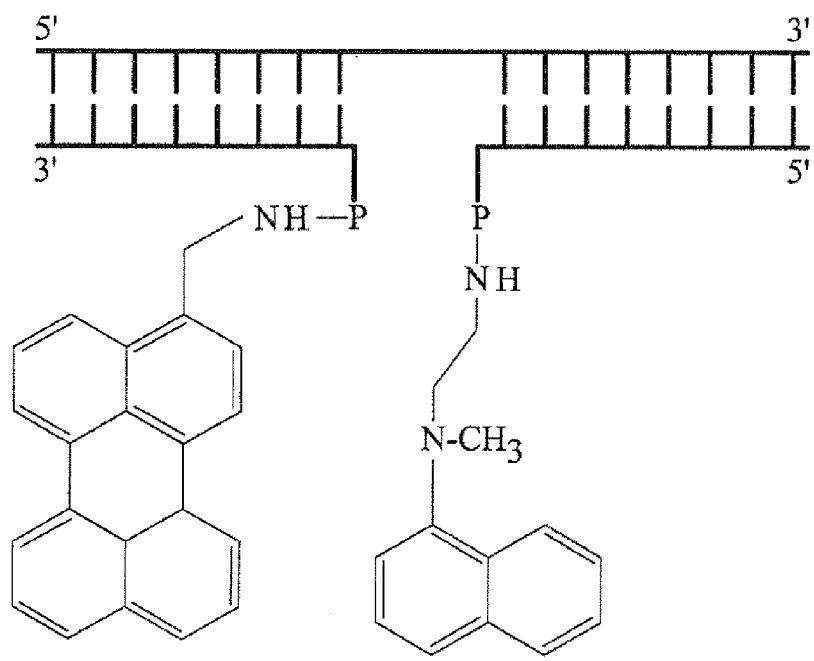
Figure 1F:
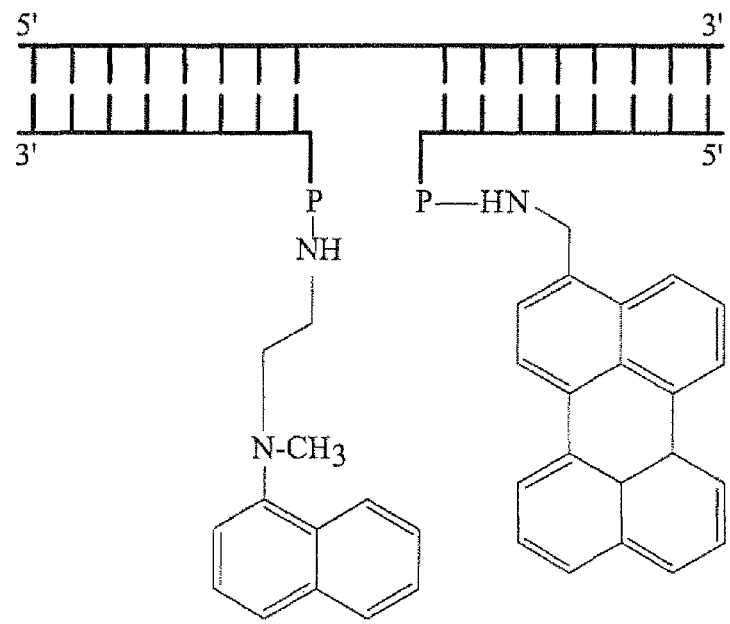
Figure 1F:
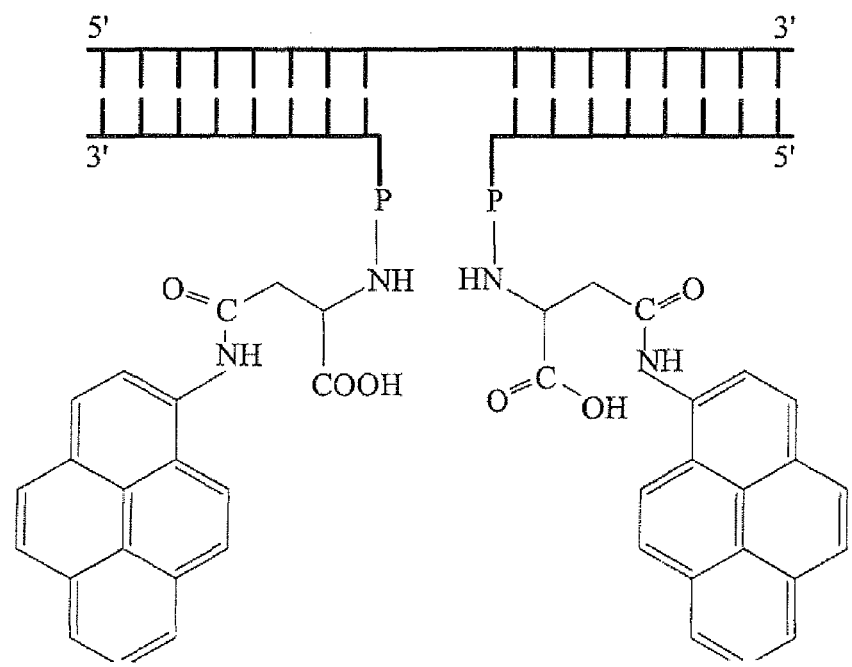
Figure 1G:
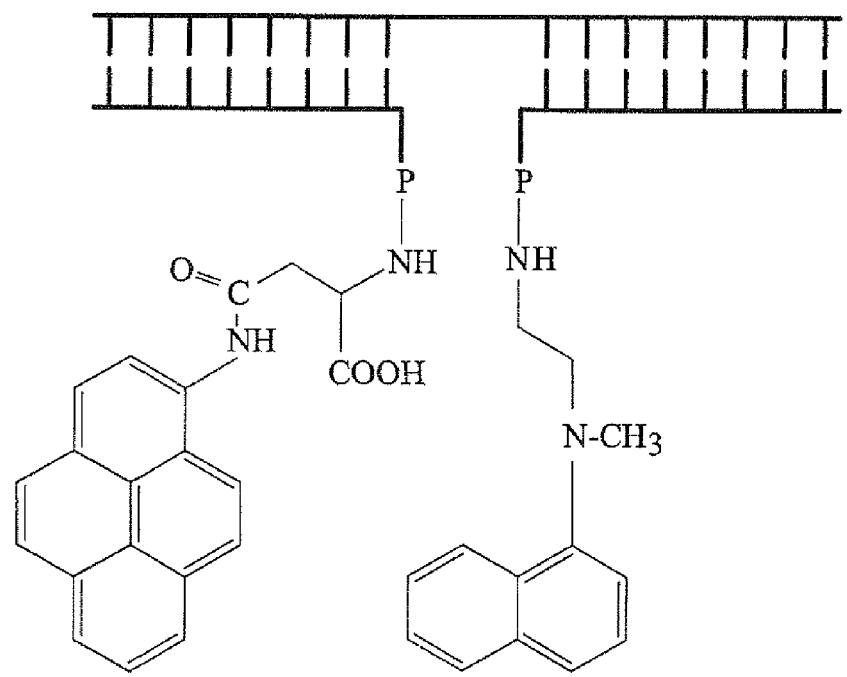
Figure 1G:
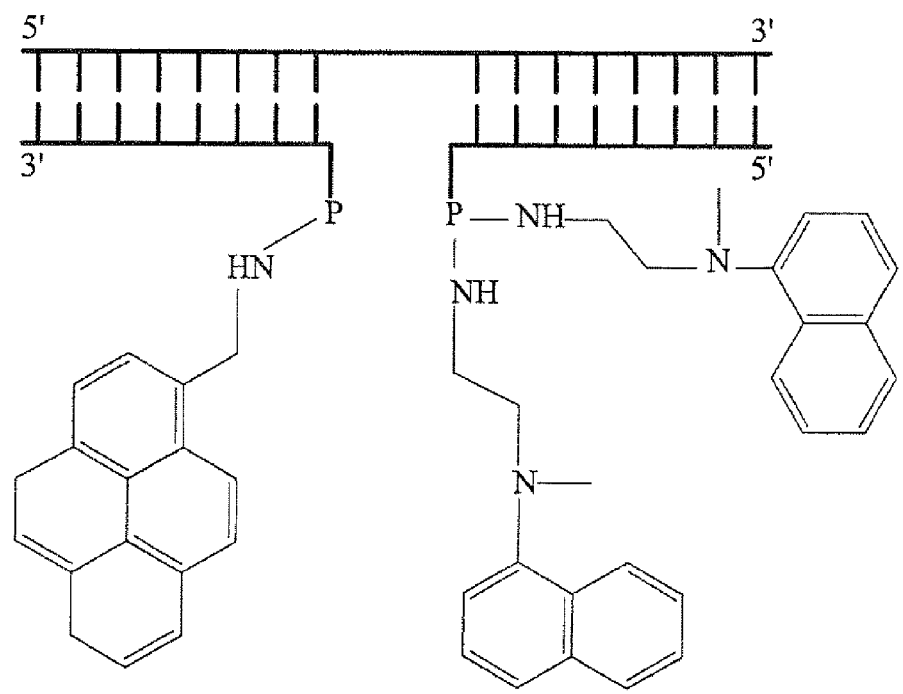
Figure 1H:
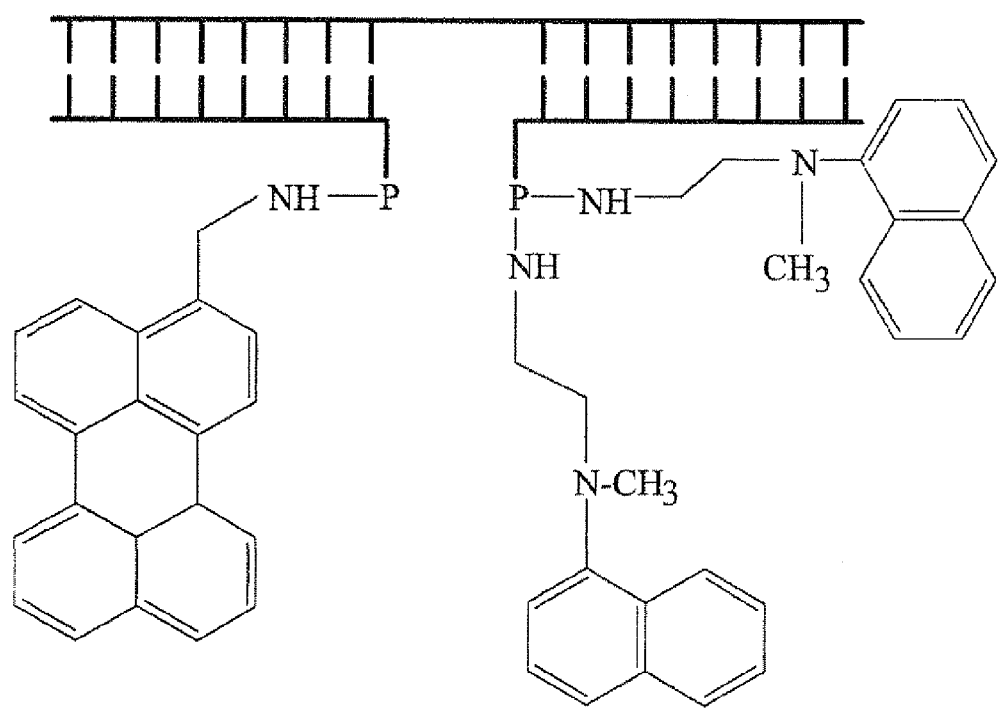
Figure 1I:
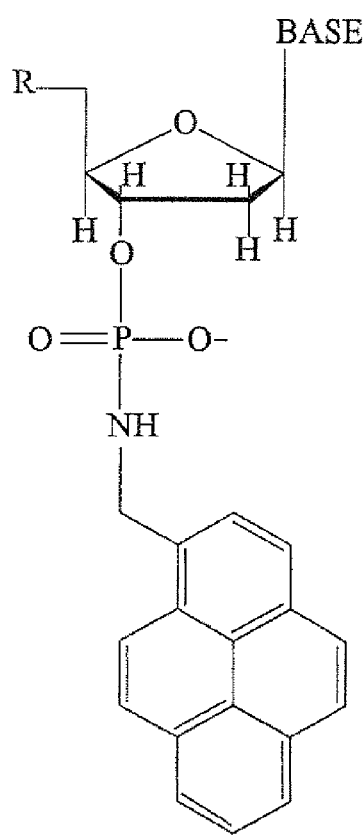
Figure 1I:
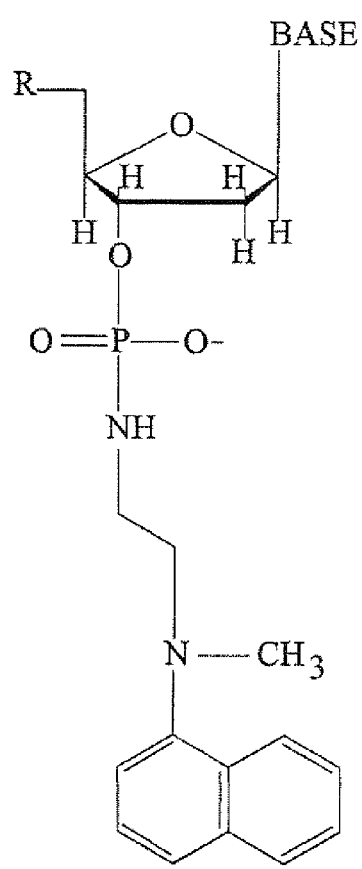
Figure 1J:
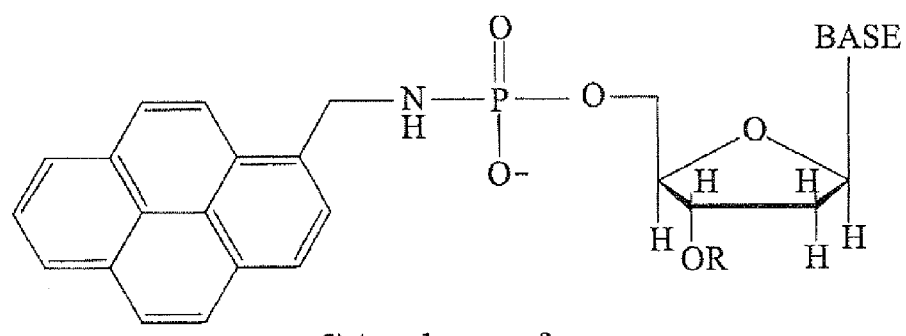
Figure 1J:
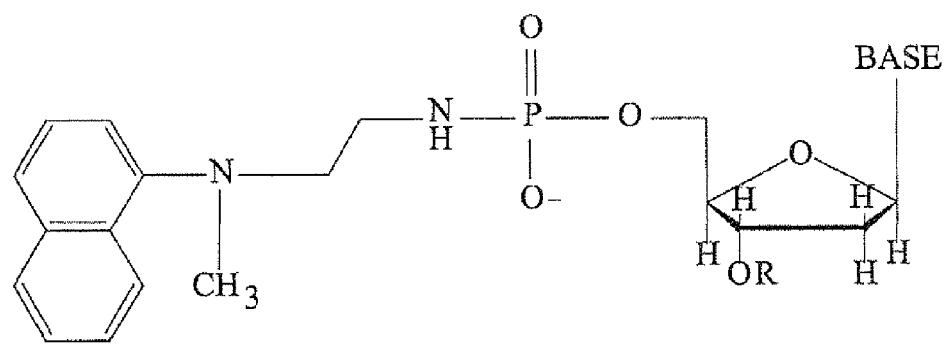
Figure 1K:
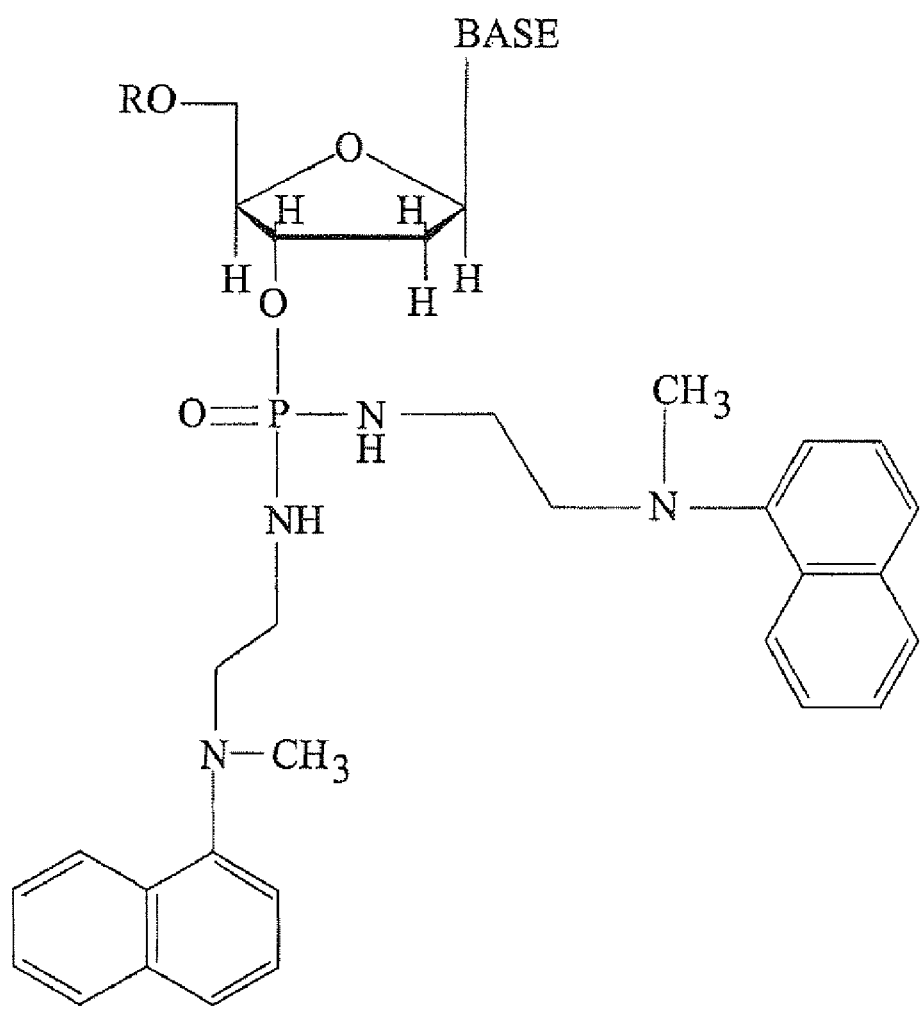

In the following Examples, the buffer containing N % TFE was prepared using 10-fold Tris buffer A (1M NaCl, 100 mM Tris, pH 8.4), the required amount of water and TFE. For instance, to prepare 100 ml of Tris buffer, containing 80% TFE, 10 ml of 10-fold Tris A buffer, 10 ml of TFE and 10 ml of water were mixed. The resulting buffer contained 0.1M NaCl, 10 mM Tris (pH 8.4) and 80% TFE. A similar procedure was used for buffers containing other co-solvents (e.g. ethylene glycol).

Furthermore, the oligonucleotide probes and target nucleic acids were prepared as $10^{-3}$M stock solutions in water. These solutions were added to the appropriate buffer to achieve a final concentration for each of the probes and target nucleic acids of 2.5 µM.

EXAMPLE 1

Solvent Effects on Excimer/Exciplex Formation.

The following three systems (SP-1, SP-19 and SP-34) were investigated in terms of their ability to form an exciplex in a variety of organic co-solvents.

Comparative) SP-1: (excimer split-probe system) (5'-3' sequence is SEQ ID NO:1)

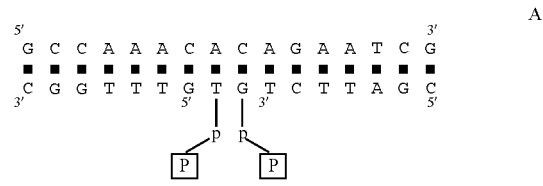

where: P is a Pyren-1-yl-methylamino group and p is a phosphate group connecting P to the backbone of the probe (see also the structural formula in FIG. 1).

SP-19 (exciplex split-probe system): (5'-3' sequence is SEQ ID NO:1)

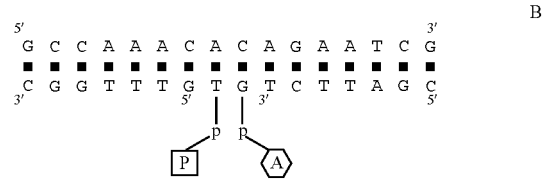

where: A is a 2-(N'-methyl-N'-naphth-1"ylamino) ethylamino group, P is a pyren-1-yl-methylamino group and p is a phosphate group connecting P or A to the backbone of the probe (see also the structural formula in FIG. 1).

SP-34 (exciplex split probe system): (5'-3' sequence is SEQ ID NO:1)

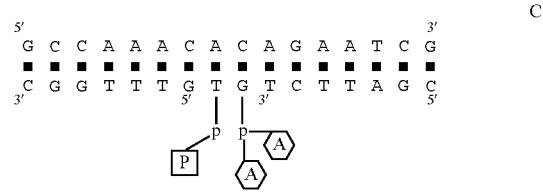

where: each A is a 2-(N'-methyl-N'-naphth-1'ylamino) ethylamino group, each attached to the 3'phosphate, P is pyren-1-yl-methylamino group and p is a phosphate group connecting P to the backbone of the probe.

The preparation of the labelled probes for use in the SP-1, SP-19 and SP-34 constructs is described in Appendix 1.

For convenience in the subsequent description, the 5' and 3' labelled probes are also referred to respectively as 5'-P-ON1 and ON2-3'-A/P.

baseline corrected and scaled to monomer exci-partner emission at 380 nm to facilitate comparison in excimer or exciplex emission.

The organic co-solvents employed and their concentrations in the "hybridisation mixture" are shown in the following Table 1 which includes the results obtained in terms of whether or not excimer or exciplex formation was detected.

TABLE 1

Summary of the influence of various tested organic solvent additives on excimer and exciplex emission of DNA-mounded exci-partners within DNA-split-probe systems in Tris Buffer (10 mM Tris, 0.1 M NaCl pH 8.5). Dielectric constant ($\epsilon$) and refractive index (n) at 25° C., and viscosity at 25° C.

| Solvent additives Tested | Viscosity Pa·s($10^{-3}$) 25 C. | $\epsilon$ | n 25 C. | Presence of excimer/exciplex formation | | | | |
|---|---|---|---|---|---|---|---|---|
| | | | | SP-1 50% | SP-1 70% | SP-19 50% | SP-19 70% | SP-34 80% |
| N-Methylformamide | 1.82 | 181.56 | 1.432 | X | X | X | X | X |
| Ethylene glycol | 21.95 | 40.245 | 1.432 | ✓ | ✓ | X | ✓ | X |
| Methanol | 0.59 | 32.613 | 1.328 | ✓ | ✓ | X | X | X |
| Trifluoroethanol | 2.04 | 26.726 | 1.291 | ✓ | ✓ | X | ✓ | ✓ |
| Ethanol | 1.21 | 24.852 | 1.361 | ✓ | ✓ | X | X | X |
| Acetone | 0.325 | 20.493 | 1.359 | ✓ | ✓ | X | X | X |
| Ethylene glycol dimethy | 0.52 | 7.200 | 1.380 | ✓ | ✓ | X | ✓ | ✓ |
| Hexafluoro-2-propanol | 1.62 | 16.75 | 1.275 | ✓ | ✓ | — | — | X |
| Tetrafluoro-1-propanol | 4.577 | — | 1.321 | ✓ | ✓ | X | X | X |
| 3-Chloro-1,2-propandiol | — | — | 1.480 | — | X | X | X | X |

The following procedure was adopted.
The order of components added was:
1. 5' labelled oligo. If necessary, heat the sample (~40° C. or even higher if necessary) to remove any background signal arising from pyrene interaction with oligo components);
2. 3'-labelled oligo;
3. Target oligo;

If emission of the naphthalene-containing or bis-naphthalene-containing oligo was sufficiently intensive (~426 nm) as measured in a separate experiment, this spectral component was recorded first, and then subtracted from the spectrum of the full tandem system. In more detail, the naphthalene-containing oligo-probes normally have emission at ~426 nm. The exciplex band is usually observed around 480 nm. Therefore, the naphthalene-partner may contribute to the emission at 480 nm. To avoid this, the emission spectrum of the naphthalene-containing monomer may be subtracted from the spectrum of the full tandem system so as to detect only the exciplex signal.

Excitation and emission spectra were recorded in thermostatted quartz cuvettes using a Shimadzu RF-5301PC spectrofluorophotometer, and implementing the "automatic shutter-on" facility to minimize photo-degradation of samples in the cuvette between measurements. Samples were not degassed before measurements. Spectra were recorded in 10 mM Tris buffer, 0.1 M NaCl, at pH 8.5 in the presence of the appropriate amount of a particular organic co-solvent (50%, 70% and/or 80%) at 10° C. The ratio of nucleic acid components used was 1:1:1 (16-mer target:5'-P-ON1: ON2-3'-A/P) each at a concentration of 2.5 µM, using excitation wavelengths of both 340 nm and 350 nm and slitwidths of 3 or 5 nm, as dictated by the intensity obtained.

With all components present, spectra were taken at 3-min intervals until excimer/exciplex emission was maximal. The system was then heated to 40° C., and allowed to slowly cool to 10° C. Again spectra were taken at 3-min intervals until excimer/exciplex emission was maximal. All spectra were It can be seen from the above Table 1 that excimer formation occurred at co-solvent concentrations of 50% and 70% for all but two of the solvents tested (i.e. N-methylformamide and 3-chloro-1,2-propandiol) which did not give excimer formation at either 50% or 70% concentration. In contrast, exciplex formation was much more dependent on the nature and concentration of the solvent. More particularly, no exciplex formation was detected for any solvent at a concentration of 50% but, in the case of SP-19, was detected for 3 solvents, (namely ethylene glycol, trifluorouethanol and ethylenegylcol dimethylether) at a concentration of 70% and, in the case of SP-34, was detected at a solvent concentration of 80% for trifluoroethanol and ethyleneglycol dimethylether.

By way of more detailed explanation of the results obtained, reference is made to FIGS. 2-7 of the accompanying drawings.

Figure 2:
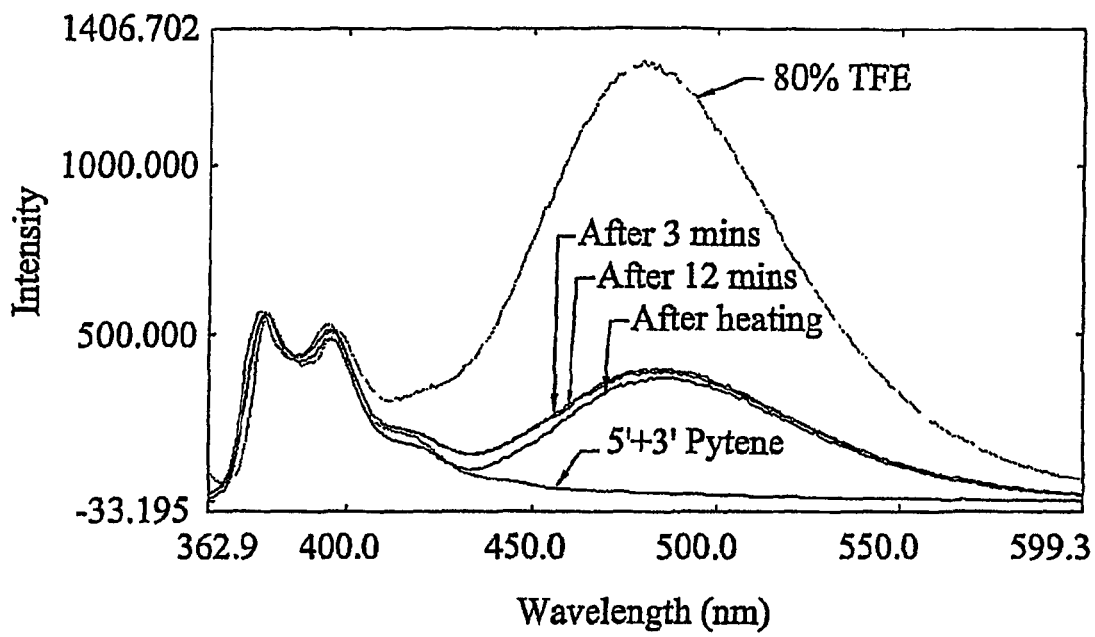
FIG. 2 illustrates the emission spectra of SP-1 in Tris buffer (10 mM TRIS, pH 8.5, 0.1 M NaCl) in the presence of hexafluoro-2-propanol additive (50%) compared with 80% TFE additive.

FIG. 2: illustrates the emission spectra of SP-1 in Tris buffer (10 mM TRIS, pH 8.5, 0.1 M NaCl) in the presence of hexafluoro-2-propanol additive (50%) compared with 80% TFE additive. The influence of time after addition of target strand and the heating-recooling cycle on excimer emission is shown. Excitation wavelength was 350 nm. Spectra are baseline-corrected corrected and scaled against the monomer emission band at 380 nm.

Figure 3:
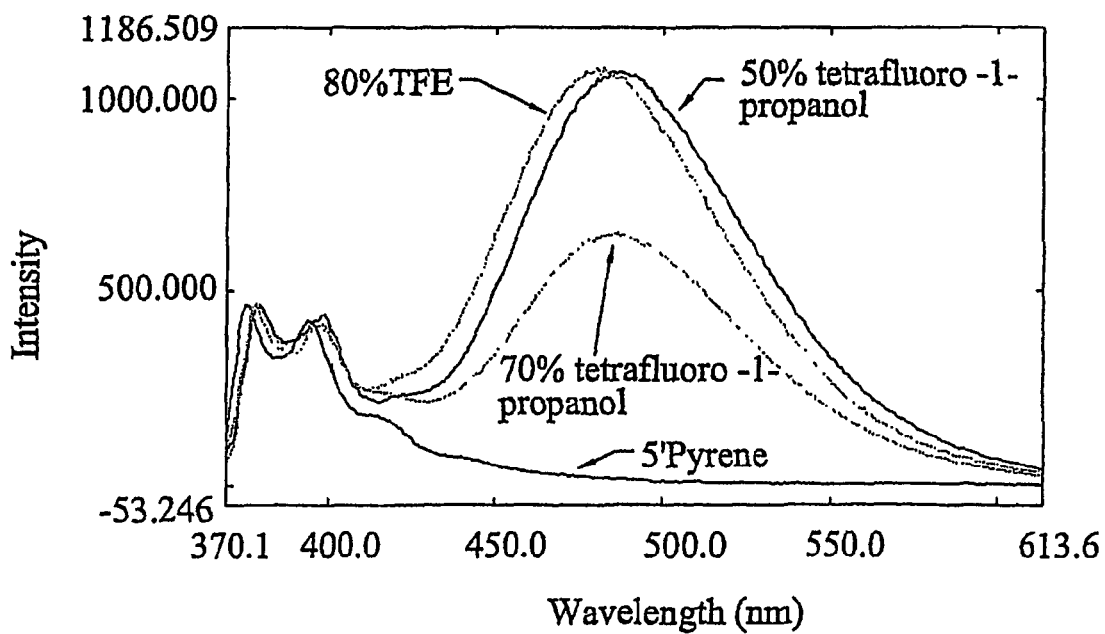
FIG. 3 illustrates the emission of spectra of SP-1 in Tris buffer (10 mM IRIS, pH 8.5, 0.1 M NaCl) in the presence of tetrafluoro-1-propanol additive (50% and 70%) compared with 80% TEE additive.

FIG. 3: illustrates the emission spectra of SP-1 in Tris buffer (10 mM TRIS, pH 8.5, 0.1 M NaCl) in the presence of tetrafluoro-1-propanol additive (50% and 70%) compared with 80% TFE additive. Excitation wavelength was 350 nm. Spectra are baseline corrected and scaled against monomer emission band at 380 nm.

The spectrum of SP-1 in the presence of 80% TFE additive is also shown for comparative purposes. It is interesting to note that 50% tetrafluoro-1-propanol is capable of inducing the same level of excimer emission as that of an 80% TFE additive (FIG. 3). However, hexafluoro-2-propanol additive was found to be less effective than TFE or tetrafluoro-1-propanol in their ability to induce excimer formation (FIG. 2).

Excimer formation within the SP-1 split-probe system also was observed in the presence of 50%, and especially, 70% ethylene glycol (FIG. 4), although the maximum of excimer emission was much less than that seen for 80% TFE. The excimer band fluorescence was developed over time to a maximum, presumably due to the increased viscosity of the solution.

Figure 4:
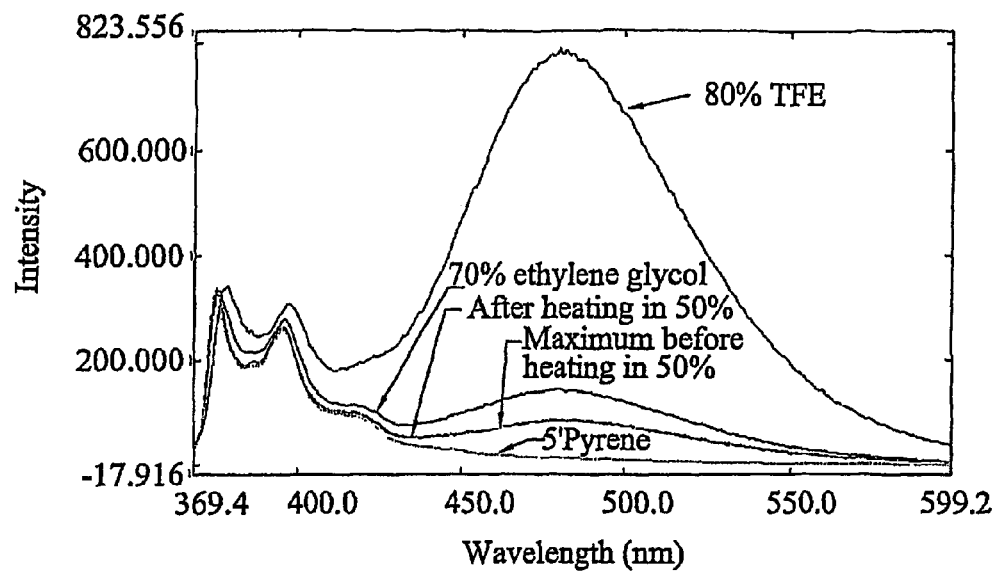
FIG. 4 illustrates the emission spectra of SP-1 in Tris buffer (10 mM TRIS, pH 8.5, 0.1 M NaCl) in the presence of ethylene glycol (50% and 70%) compared with 80% TFE additive.

FIG. 4: Emission spectra of SP-1 in Tris buffer (10 mM TRIS, pH 8.5, 0.1 M NaCl) in the presence of ethylene glycol (50% and 70%) compared with 80% TFE additive. Excitation wavelength was 350 nm. Spectra are baseline-corrected and scaled against monomer emission band at 380 nm.

Figure 5:
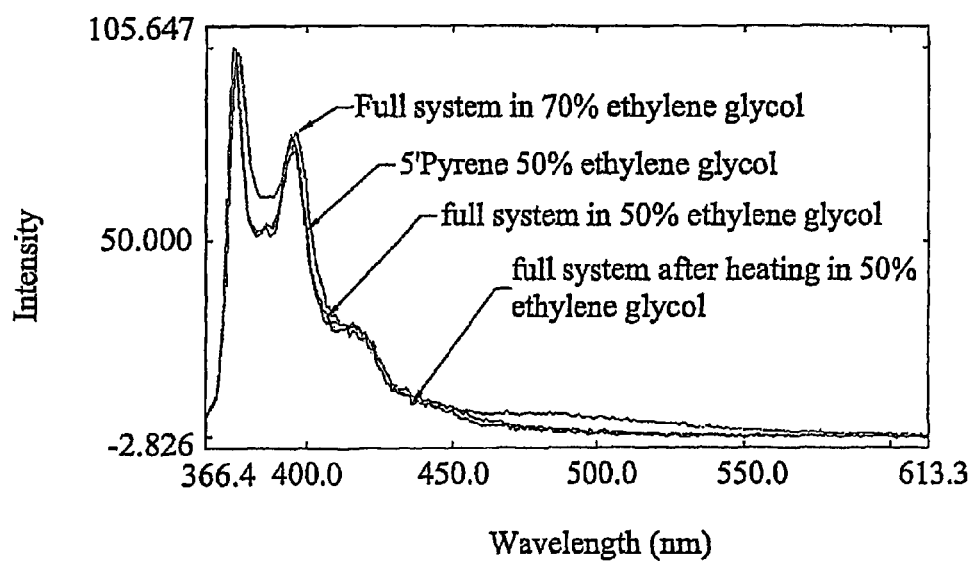
FIG. 5 illustrates the emission spectra of SP-19 in Tris buffer (10 mM TRIS, pH 8.5, 0.1 M NaCl) in the presence of ethylene glycol additive (50% and 70%).

FIG. 5: Emission spectra of SP-19 in Tris buffer (10 mM TRIS, pH 8.5, 0.1 M NaCl) in the presence of ethylene glycol additive (50% and 70%). Excitation wavelength was 350 nm. Spectra are baseline-corrected and scaled against monomer emission band at 380 nm.

Figure 6:
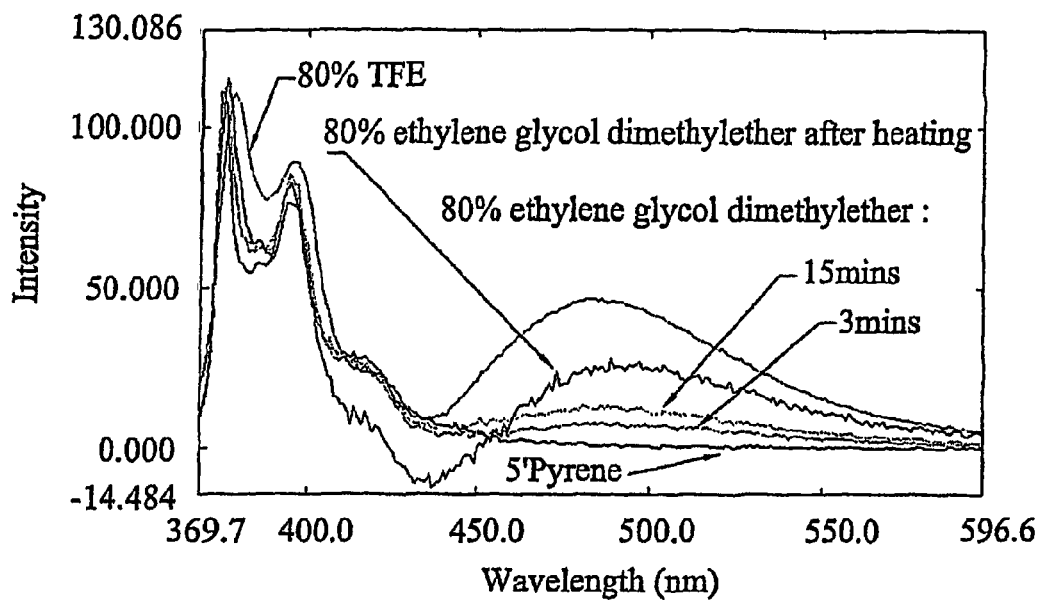
FIG. 6 illustrates the emission spectra of SP-34 in Tris buffer (10 mM TRIS, pH 8.5, 0.1 M NaCl) in the presence of ethylene glycol dimethyl ether additive (80%) compared with 80% TFE additive.

FIG. 6: Emission spectra of SP-34 in Tris buffer (10 mM TRIS, pH 8.5, 0.1 M NaCl) in the presence of ethylene glycol dimethyl ether additive (80%) compared with 80% TFE additive. Excitation wavelength was 350 nm. Spectra are baseline-corrected and scaled against monomer emission band at 380 nm.

Figure 7:
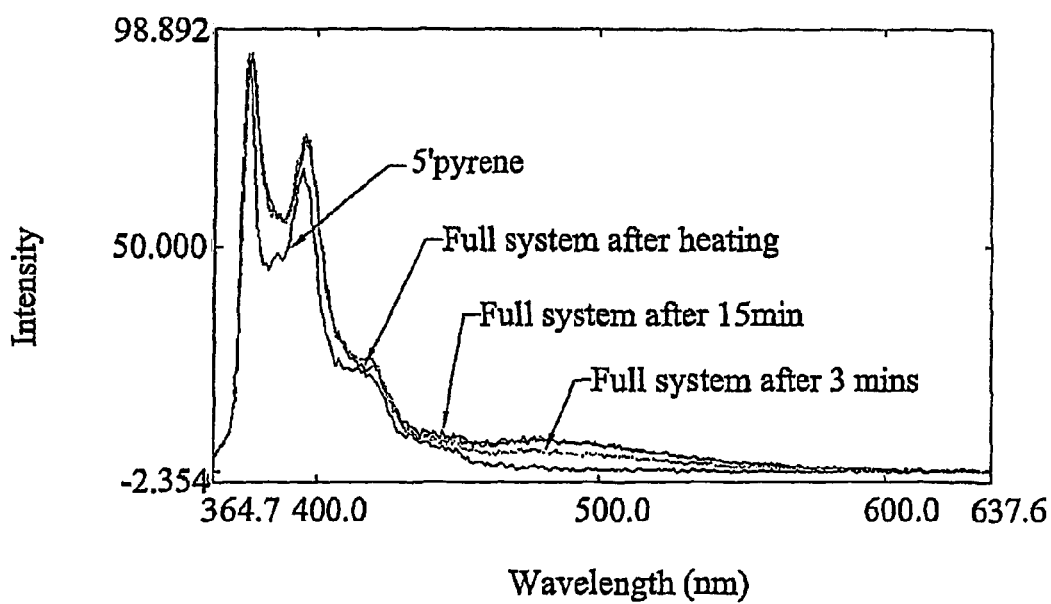
FIG. 7 illustrates the emission spectra of SP-34 in Tris buffer (10 mM TRIS, pH 8.5, 0.1 M NaCl)in the presence of ethylene glycol dimethylether additive (80%).

FIG. 7: Emission spectra of SP-34 in Tris buffer (10 mM TRIS, pH 8.5, 0.1 M NaCl) in the presence of ethylene glycol dimethylether additive (80%). Excitation wavelength was 350 nm. Spectra are baseline corrected and scaled against monomer emission band at 380 nm.

EXAMPLE 2

Effect of Partners on Exciplex Formation

This Example is based on hybridisation of 8-mer oligonucleotide (ON) probes labelled with exciplex partner moieties to a 16-mer nucleic acid target (close to the minimal size of about 18-mer that would be needed uniquely to locate a piece of DNA within the full genome of a human cell). The nucleotide sequence for the 16-mer target and the 8-mer oligonucleotide probes are shown below in Scheme 1 in which A and D represent exciplex partner moieties, p represents a phosphate group and L and L are linker moieties by which A/D is bonded to the oligonucleotide probe. For an excimer, A and D are identical and in the case of an exciplex represent acceptor and donor, respectively. Two alternative configurations for acceptor and donor moieties are represented by the two drawings (i) and (ii).

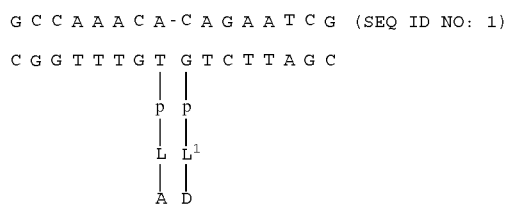

(i)

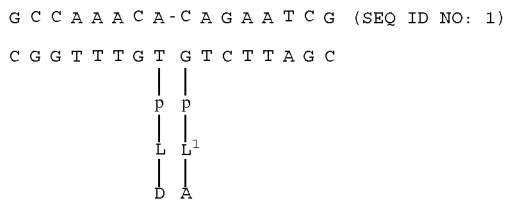

(ii)

In this particular case, the nucleotide sequence for the 16-mer target and the two 8-mer oligonucleotides was selected to avoid the formation of hairpins (and other elements of secondary structure) and to minimise the formation of any non-perfect duplex structures.

FIG. 1 identifies a number of duplexes of the type illustrated in Scheme 1 above that were studied for the purposes of this Example. For convenience, the duplexes illustrated in FIG. 1 are identified below as SP-1, SP-2 . . . etc. in accordance with the labelling shown on FIG. 1.

Hybridisation assays were carried out using the procedure described in Example 1.

Figure 9:
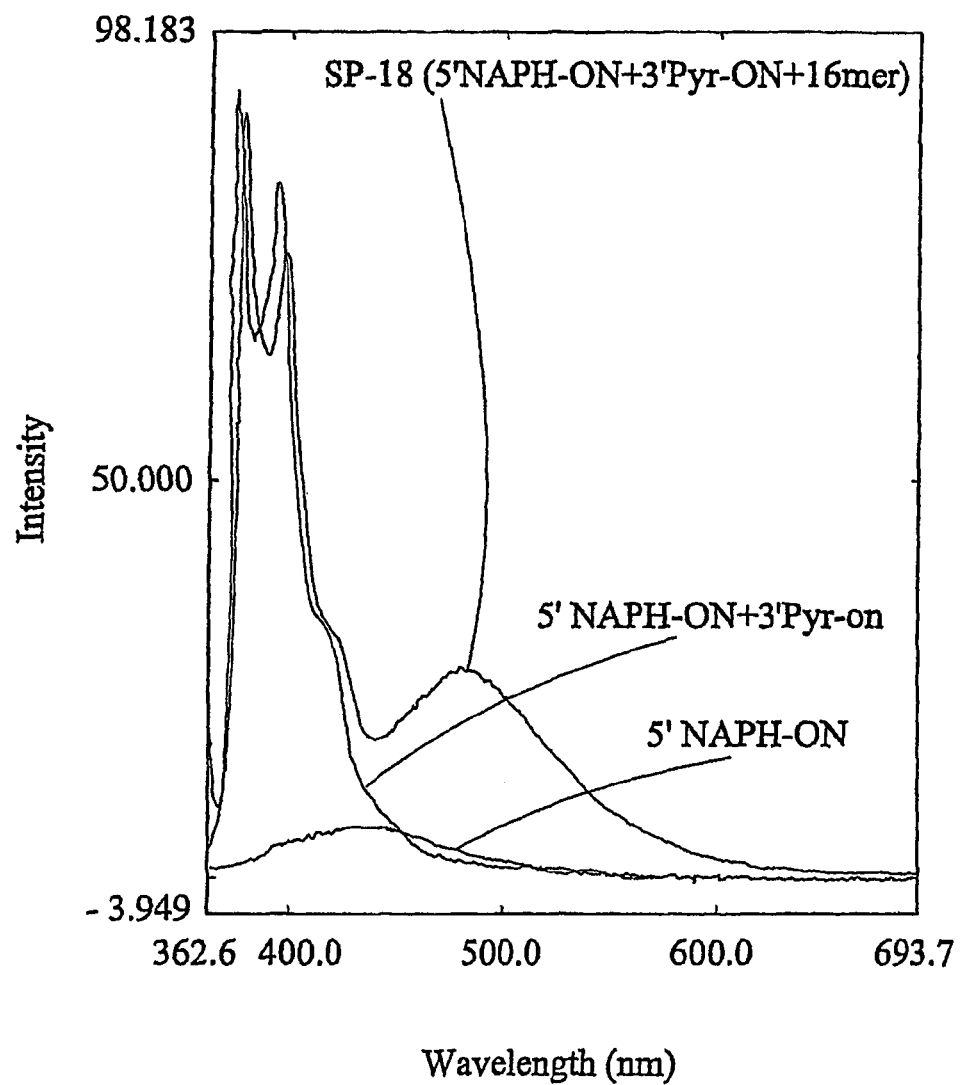
FIG. 9 illustrates the emission of spectra of SP-18 in Tris buffer in the presence of 80% TFE additive.
Figure 10:
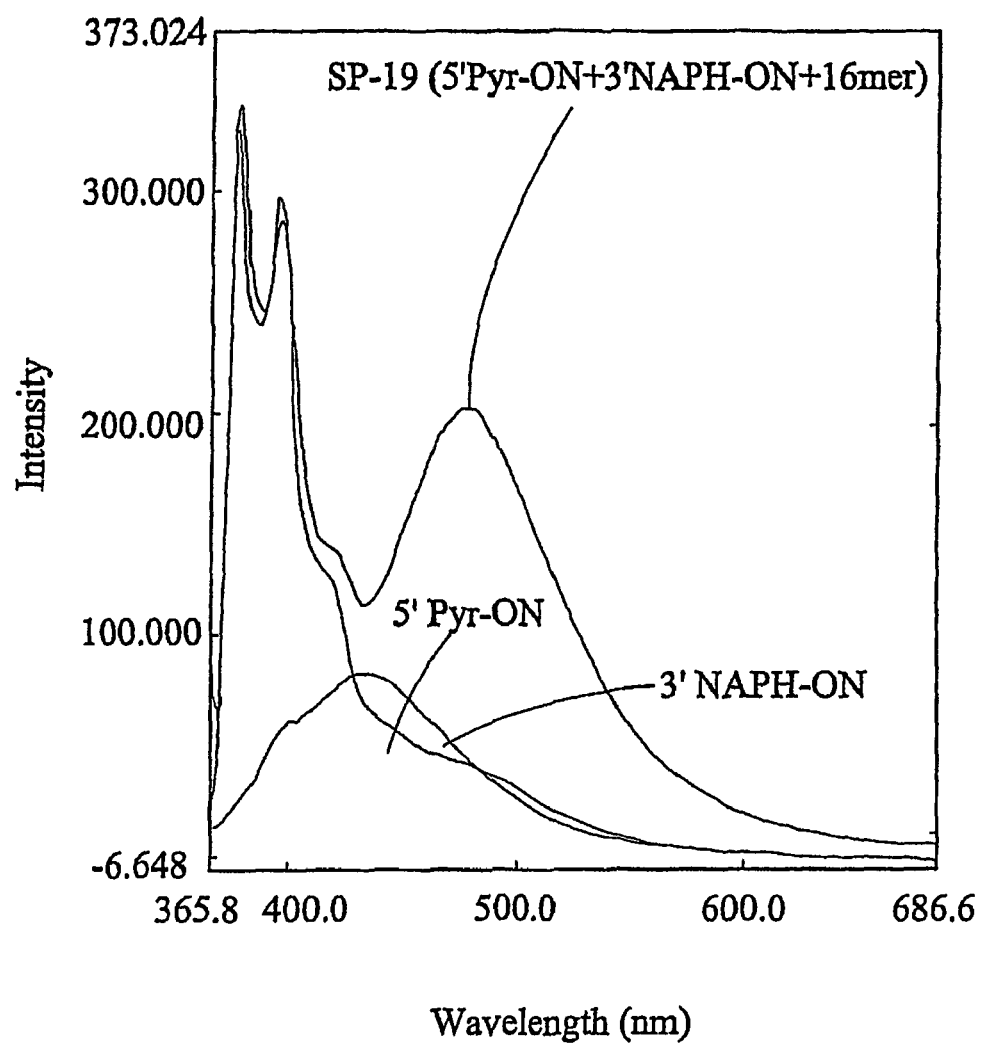
FIG. 10 illustrates the emission of spectra of SP-19 in Tris buffer in the presence of 80% TFE additive.
Figure 20:
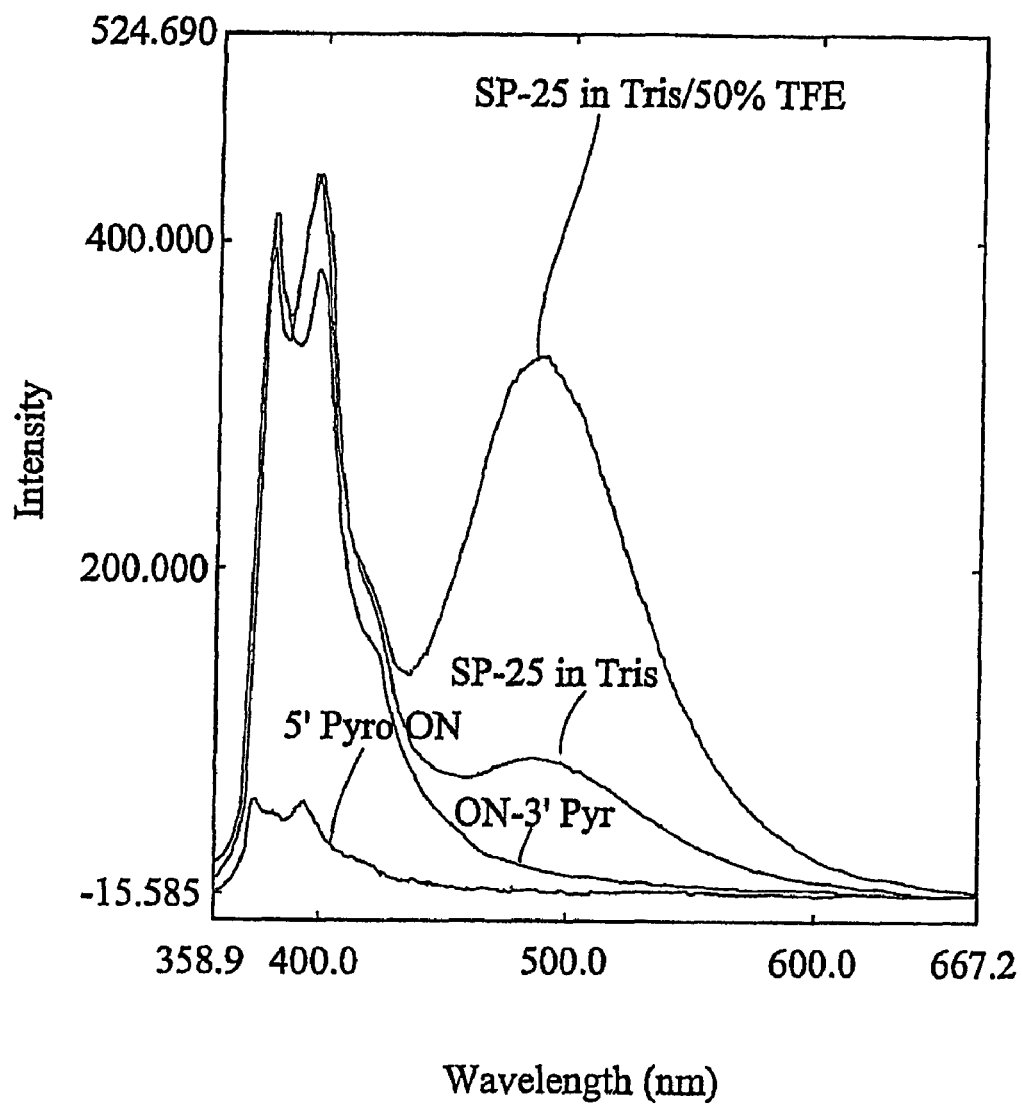
FIG. 20 illustrates the emission of spectra of SP-25 in Tris buffer in the presence of 80% TFE additive and in the absence of TFE additive.
Figure 21:
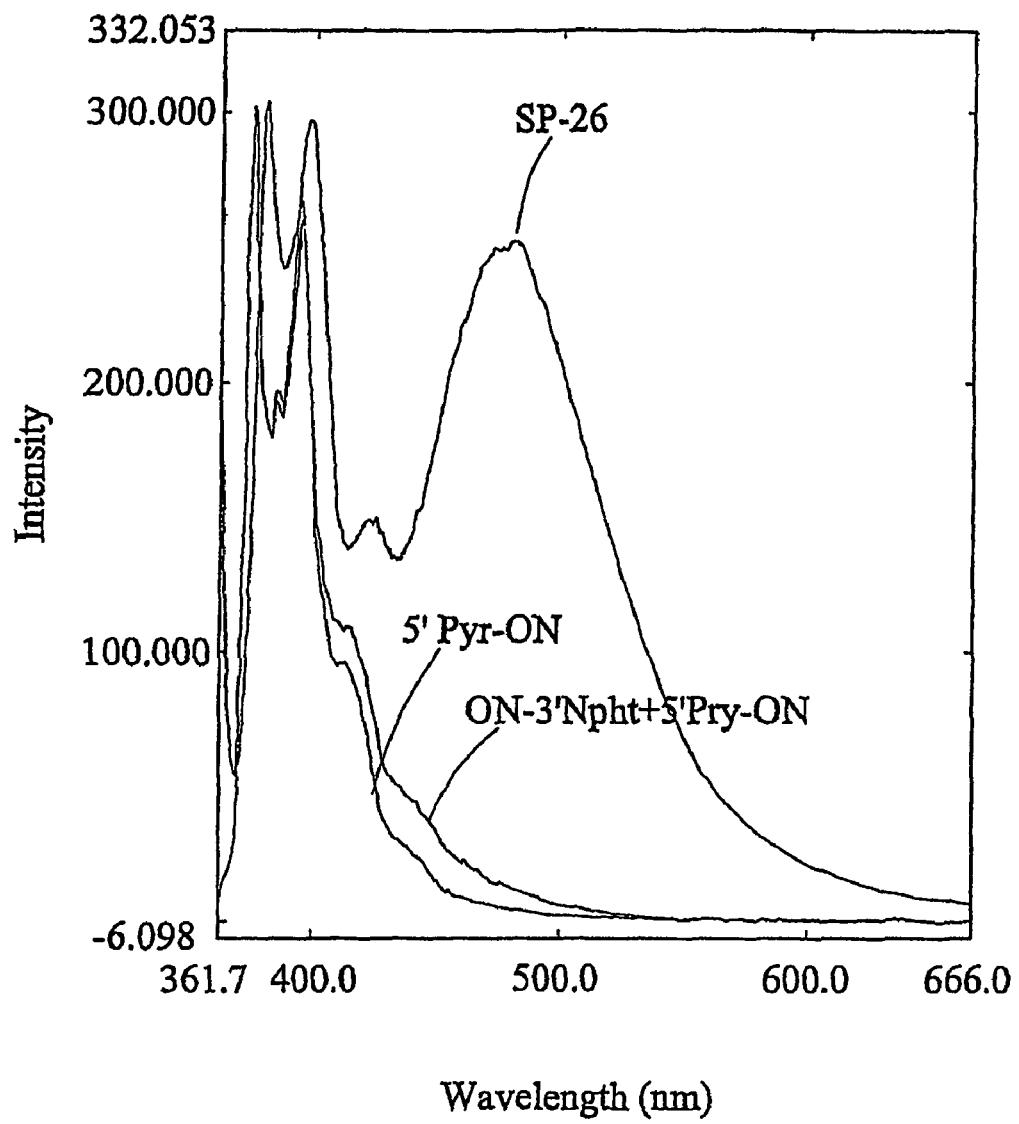
FIG. 21 illustrates the emission of spectra of SP-26 in Tris buffer in the presence of 80% TFE additive.

The systems SP-17 to SP-20, SP-25 and SP-26 did not show any exciplex emission in fully aqueous medium (i.e. without addition of TFE) (data not shown). However, when the aqueous medium included 80% by volume TFE, exciplex emission was observed at about 480 nm in the case of SP-17 (FIG. 8), SP-18 (FIG. 9), SP-19 (FIG. 10), SP-4 (FIG. 13), SP-20 (FIG. 14), SP-25 (FIG. 20) and SP-26 (FIG. 21)

Figure 11:
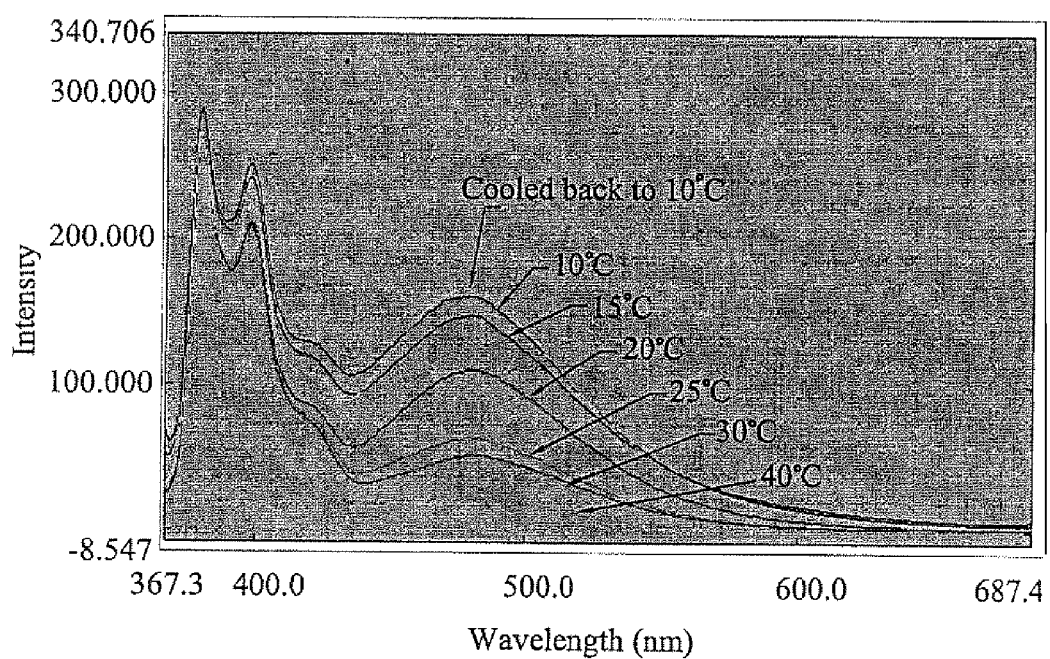
FIG. 11 illustrates a study of the exciplex emission of SP-19 in 80% TFE at temperatures of 15° C., 20° C., 25° C., 40° C. with cooling back to 10° C.

In the case of SP-19, a study of the exciplex emission in 80% TFE was made for the systems at temperatures of 15° C., 20° C., 25° C., 40° C. and cooled back to 10° C. The results are shown in FIG. 11 from which it can be seen that at 40° C. the hydrogen bonds maintaining the duplex structure are destroyed and the duplex "melts". This results in the release of the 8-mer oligonucleotides from the duplex structure accompanied by the separation of the exciplex partners. As a result, the exciplex emission decreases as the temperature increases showing an S-like sigmoidal melting curve as typically seen for thermal denaturation of double-stranded DNA. On cooling back to 10° C., the chains re-anneal, the full SP-19 tandem system reassembles and the duplex re-forms with concomitant assembly of the exciplex so that emission is again obtained.

Comparison of SP Systems

Figure 12:
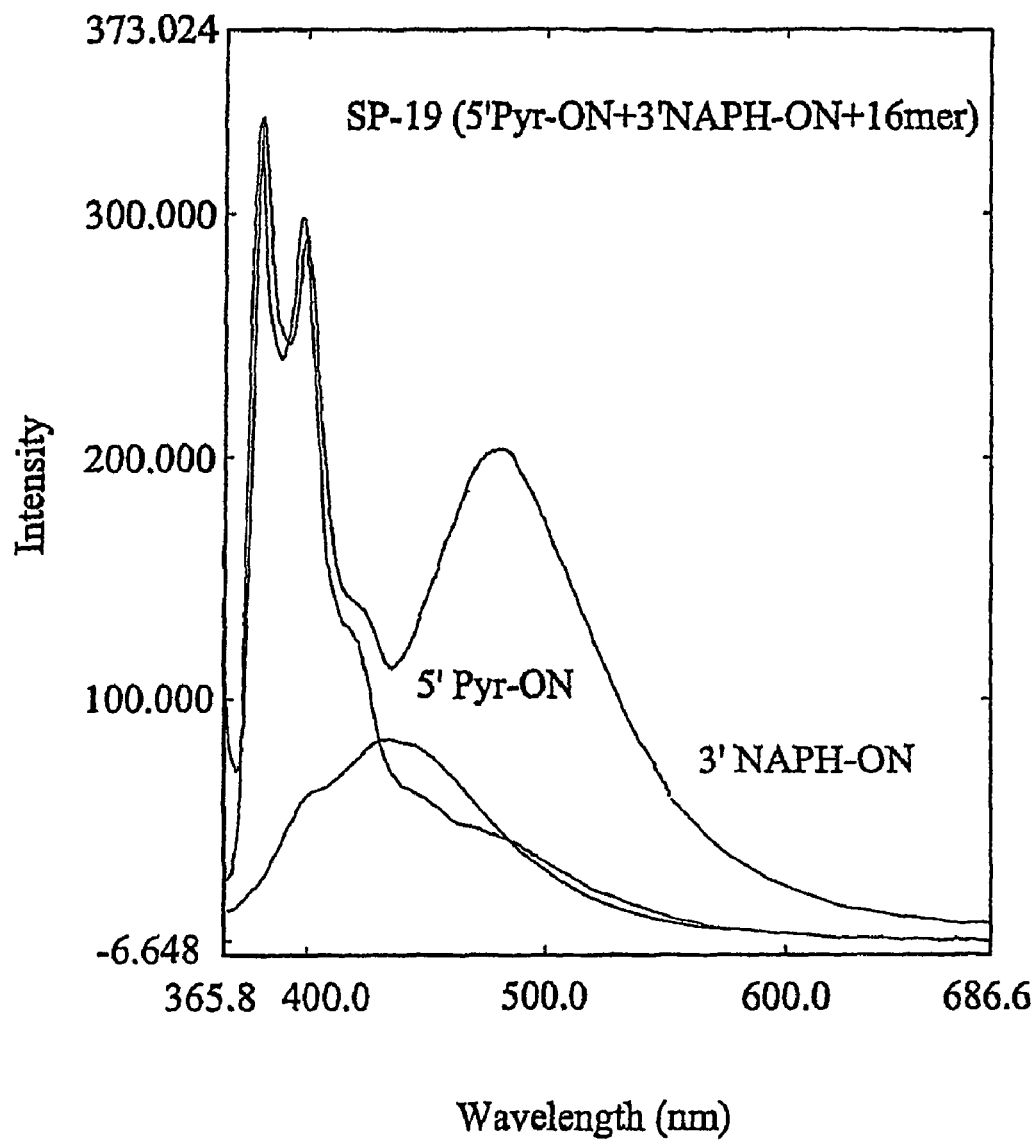
FIG. 12A illustrates the emission spectra of SP-19 and
FIG. 12B displays the emission spectra of SP-23 both recorded in Tris buffer containing 80% v/v TFE so as to provide a comparison of the relative effectiveness of perylene and pyrene as the acceptor partner for an exciplex with the same donor partner.
Figure 12B:
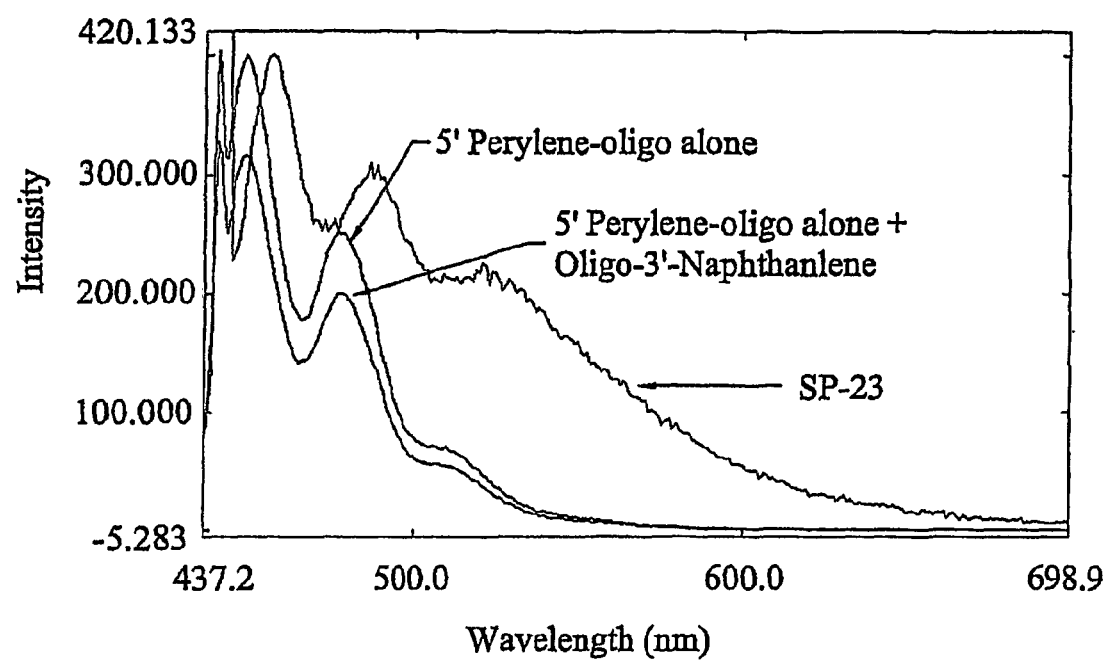

FIG. 12 (A and B) provides a comparison of the relative effectiveness of perylene and pyrene as the acceptor partner for an exciplex with the same donor partner. More particularly, FIG. 12A displays the emission spectra of SP-19 and FIG. 12B displays that of SP-23 which have 5'-pyrene and 5'-perylene acceptor groups, respectively (both having the 3'-DMN donor group (where DMN is the 2-(N'-methyl-N'-naphthalen-1"ylamino)ethylamino group)).

The spectra were recorded in Tris buffer, (10 mM Tris, 0.1 M NaCl, pH 8.3), 80 v/v TFE.

For SP-19 (pyrene/DMN) a well-resolved exciplex band (in the region of 480 nm) with a Stokes shift of around 150 nm was observed. In the case of SP-23 (perylene/DMN) the exciplex band had a lower relative integral intensity and was partially overlapped by the monomer band.

The results of FIG. 12 (A & B) demonstrate that, for a given donor, pyrene is preferred as an acceptor over perylene on the basis of the Stokes' shifts.

Figure 8:
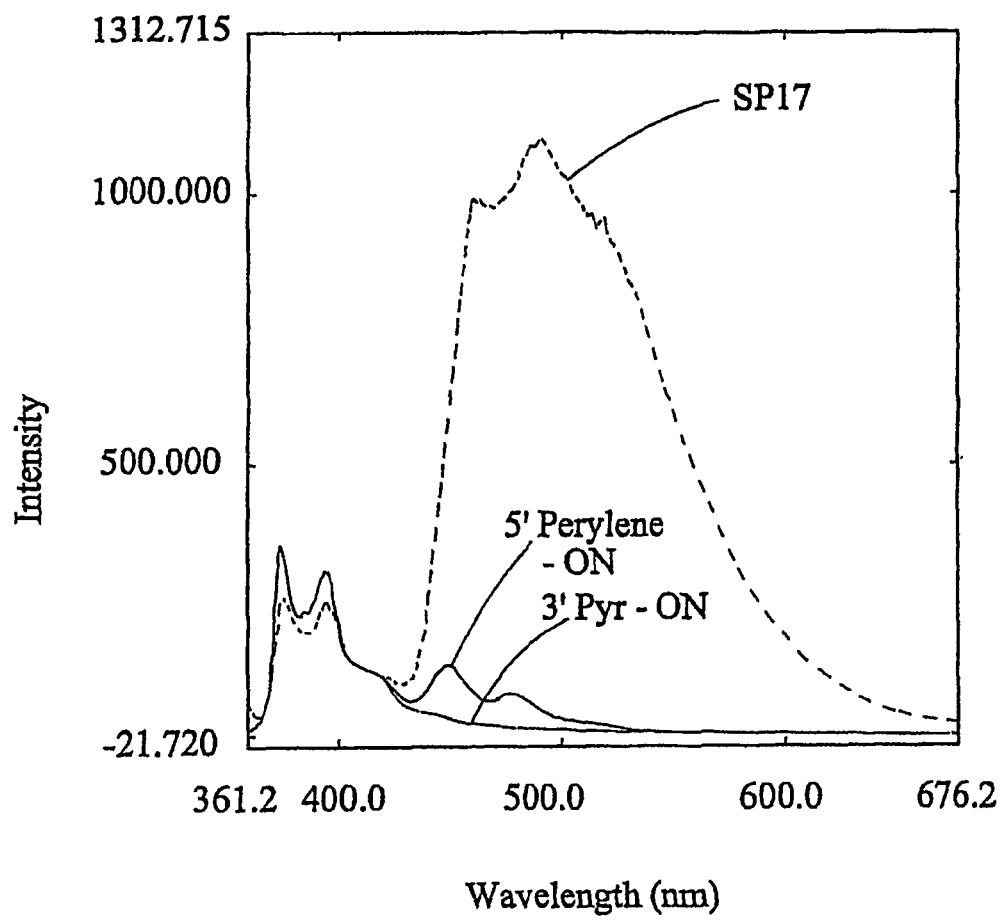
FIG. 8 illustrates the emission of spectra of SP-17 in Tris buffer in the presence of 80% TFE additive.

However as shown in FIG. 8 (see above) perylene can successfully form an exciplex with a pyrene partner if the latter partner is excited at 350 nm. As shown in FIG. 8, a very intense band was detected in the case of SP-17 from the exciplex formed between 5'-pyrene and 3'-perylene after excitation of the pyrene group at 350 nm.

Figure 13:
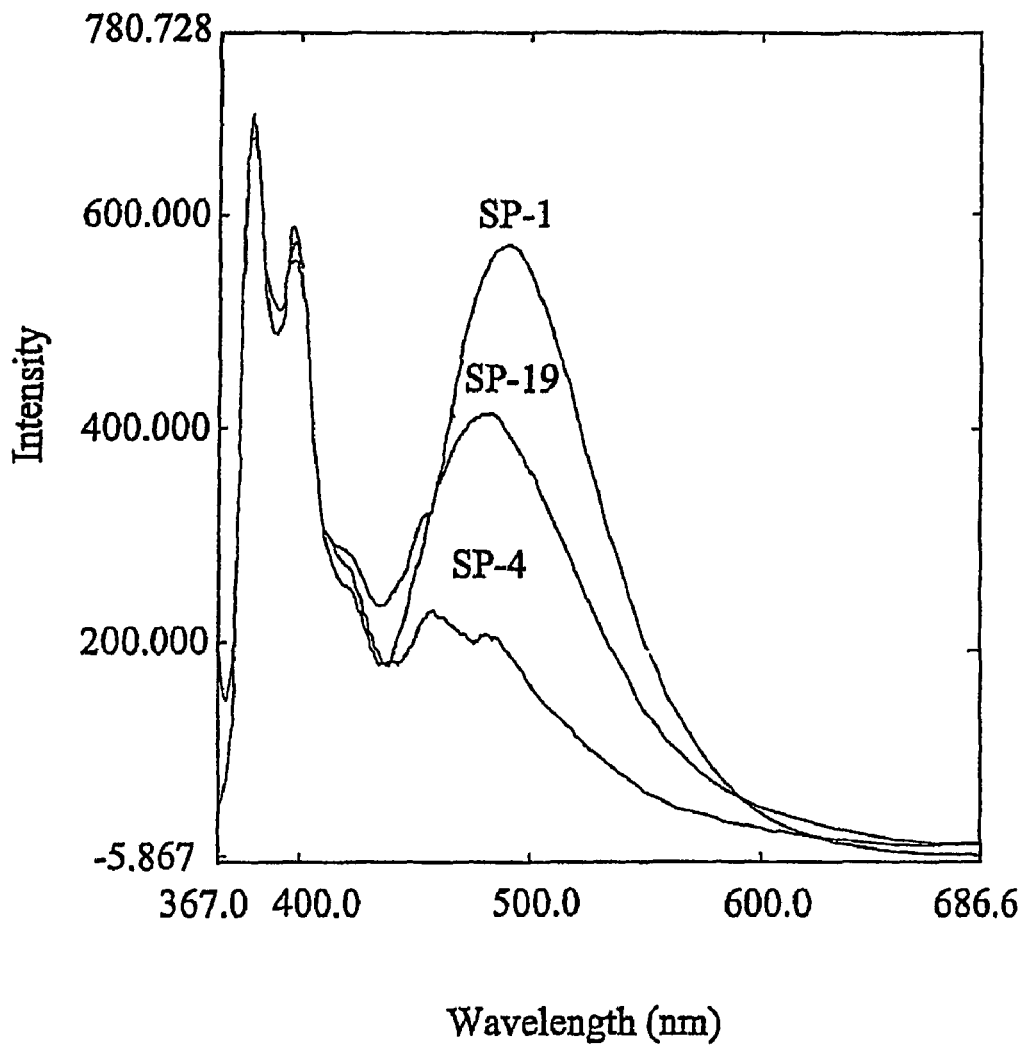
FIG. 13 illustrates the emission of spectra of SP-1, SP-4 and SP-19 in Tris buffer in the presence of 80% TEE additive.

FIG. 13 illustrates, for a pyrene acceptor, the effect of hydrophobicity of the donor on excimer/exciplex formation. More particularly, FIG. 13 shows the relative emission intensities of the exciplexes for the SP-4 and SP-19 systems and the excimer of the SP-1 system (recorded in 10 mM Tris, pH 8.3, 0.1 M NaCl in 80% TFE (spectra are scaled using the monomer emission band at 380 nm as a reference). It can be seen that the relative integral intensity of the excited-state complex is highest for SP-1 which has another pyrene as a donor group. The substitution of the 3' pyrene by the 3'-DMN group (SP-19) results in a decrease of relative integral intensity of exciplex emission as compared to SP-1. Replacement of the donor by 3'-DMA (MNN-4-(N,N-dimethylamino)phenyl) to give SP-4 results in a further decrease in the relative intensity of the exciplex band.

From these data, it can be seen that for a given acceptor (pyrene) the ability to form a complex in the presence of TFE diminishes in the following order of donor partners:

Pyrene>DMN>DMA

The above order also represents the relative orders of hydrophobicity of the donors. It probably also reflects the difference in energy between interacting molecular orbitals of donor and acceptor. Thus for a given acceptor the donor should be as hydrophobic as possible all other things being equal.

Figure 14:
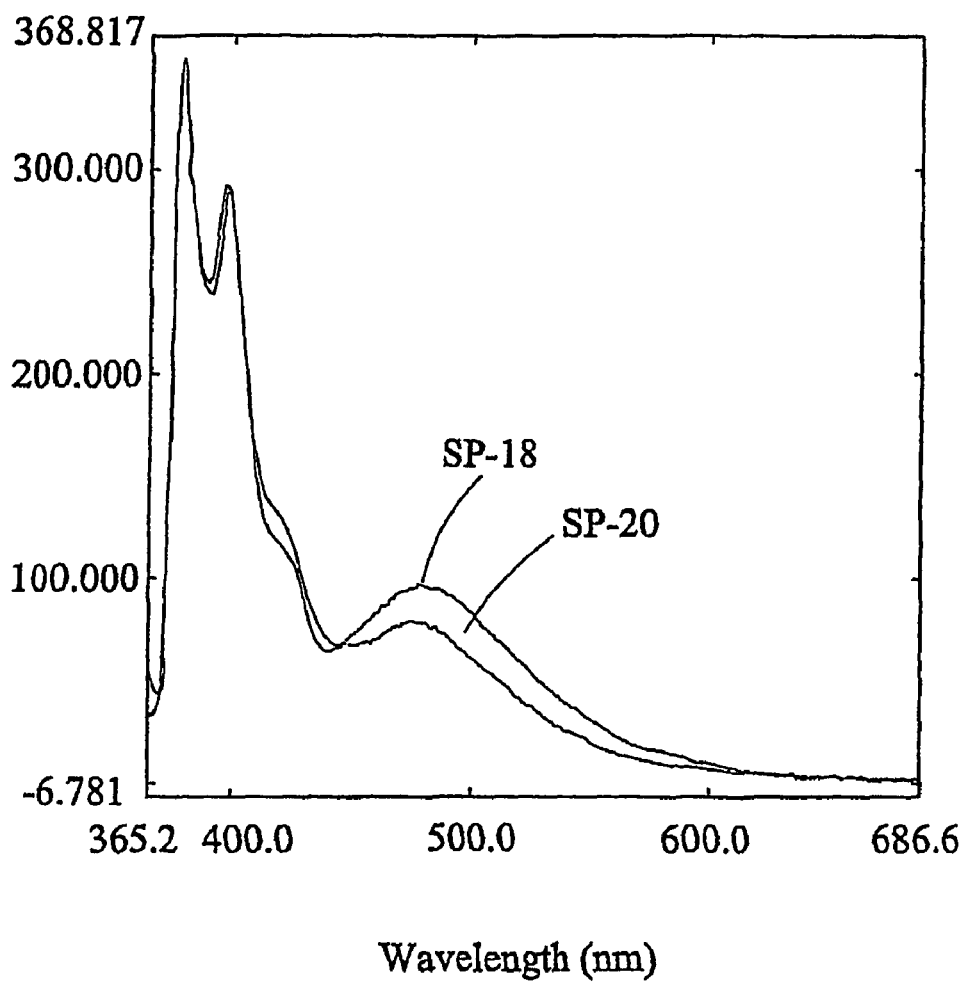
FIG. 14 illustrates the emission of spectra of SP-18 and SP-20 in Tris buffer in the presence of 80% TFE additive.

FIG. 14 illustrates the effects of the electron-donor properties of the donor partner. More particularly, FIG. 14 shows the emission spectra of SP-18 and SP-20 both of which have pyrene as the acceptor partner of the exciplex but which have a DMN partner and a MMN (i.e. the 2-(N'-naphthalen-1''lamino)ethylamino (MMN) group) partner respectively as the donor. The relative integral intensity of the exciplex band is slightly higher for SP-18 than SP-20.

EXAMPLE 3

This Example illustrates RNA target detection by exciplex formation in a split-probe system using DNA-based short probe oligos bearing exciplex forming partners ("exci-partners").

Two 8-mer probes were used to complement a 16-mer parent RNA sequence (SEQ ID NO:2) as shown below, the sequences being chosen so that they were not self complementary, only bound to the parent RNA sequence in the way required, and were not able to overlap.

```
G-C-C-A-A-A-C-A-C-A-G-A-A-U-C-G   RNA target strand
C-G-G-T-T-T-G-T G-A-C-T-T-A-G-C
     A              B
```

In the above formula, A=5'P and B=3'Np where P represents a pyrene attached by a linker to the phosphate site on the oligo-probe and Np represents a 4-(N,N-dimethylamino) naphthalene nucleus. (The probes are in effect the same as those used in SP-19, Example 1). For convenience, the left hand DNA probe is identified in the following description as 5'P-ON1 and the right hand probe is identified as 3'Np-ON2. For convenience, the assembled construct composed of the 16-mer parent RNA sequence and probes 5'P-ON1 and 3'Np-ON2 hybridised thereto is also referred to herein as RNASP-19 or RNA-BASED SP19.

Spectra were recorded in 10 mM TRIS buffer, 0.1M NaCl, at pH 8.5 in the presence of the 72% TFE at 10° C. The ratio of components used was 1:1:1 (RNA 16mer Target:5'P-ON1: 3'Np-ON2), each at a concentration of 2.5 µM using excitation wavelengths of both 340 nm and 350 nm and slitwidths of 3 or 5 nm, as dictated by the intensity obtained.

The system components were added individually from stock solutions in the order: 3'-Np-ON2, then 5'P-ON1, then RNA target. When all components were present, the system was left to equilibrate for 10 minutes and a spectrum taken.

In all examples of spectra a baseline correction was performed by subtracting the emission spectrum of the buffer and naphthalene. Spectra were scaled to corresponding monomer emission for each series of experiments to enable comparison in change of exciplex emission.

Similar experiments were conducted with the SP-19 system (DNA).

Emission Spectra for the RNA-Based Exciplex SP-19 System.

Figure 15A:
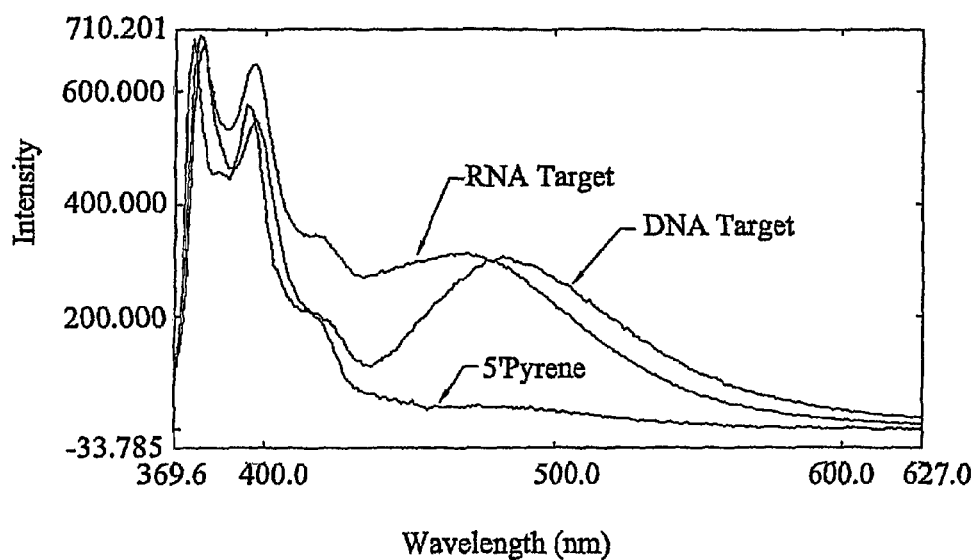
FIG. 15A illustrates the emission spectra for the RNA-based SP-19 exciplex system comparing the RNA target to the equivalent DNA target system (SP-19).

FIG. 15a shows the emission spectra for the RNA-BASED SP-19 exciplex system comparing the RNA target to the equivalent DNA target system (SP-19). For the system with the RNA target (RNA-BASED SP-19) in 80% TFE/Tris (pH 8.5), exciplex emission was observed, with a $\lambda_{max}$ value of 469 nm (compare the DNA-DNA system with $\lambda_{max}$ 480 nm). The value of $I_E/I_M$ in the presence of either target (DNA or RNA) was similar, being 0.45 for DNA and 0.41 for RNA. ($I_E/I_M$ is the ratio between the intensity of the exciplex emission band at 480 nm ($I_E$) and the intensity of the monomer band at 379 nm ($I_M$).

Figure 15B:
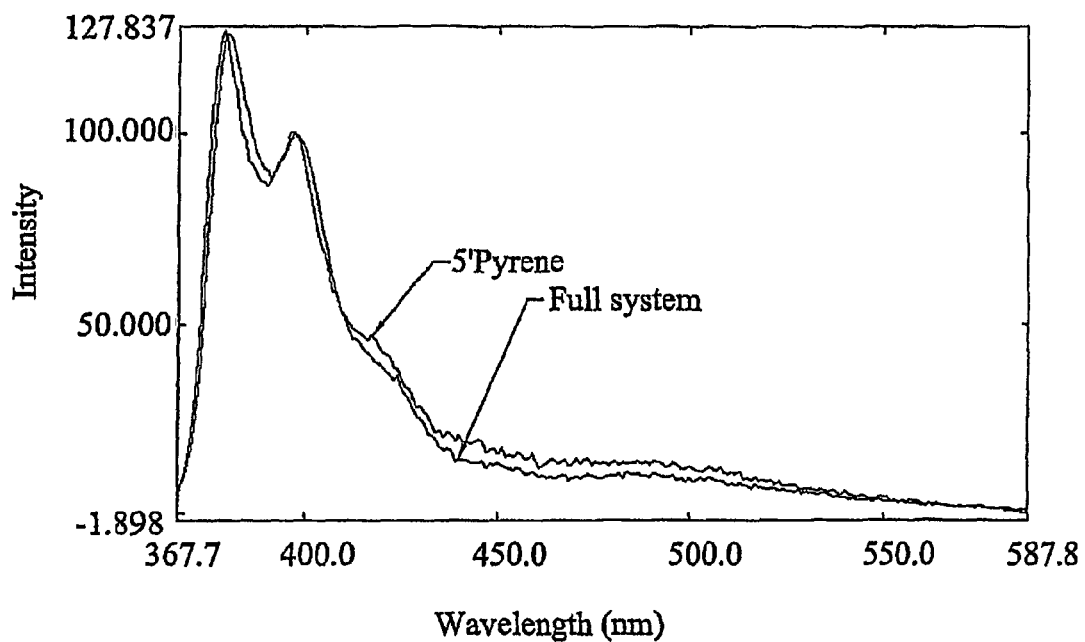
FIG. 15B illustrates the emission spectra of 5-pyrene-bearing oligo (ON1-5'pyrene) and the full RNA-BASED SP-19 system in Tris buffer at 10° C.
Figure 15C:
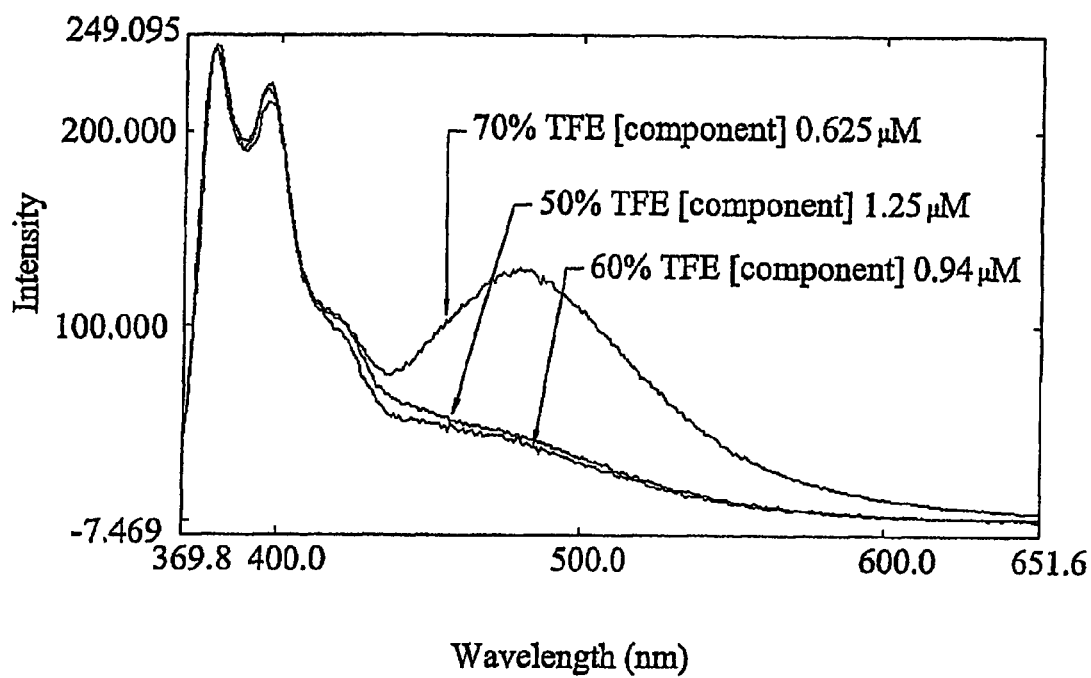
FIG. 15C illustrates emission spectra of RNA-based SP-19 IN Tris buffer at various TFE concentrations.

In the absence of TFE no exciplex emission was seen for the RNA-BASED SP-19 system, the small emission around 480 nm being also present for 5'-pyrene-bearing probe (FIG. 15b). This was due to background emission caused by pyrene forming an exciplex with the aromatic rings of the nucleotide bases. Exciplex emission resulting from the desired exci-partners was not seen at TFE concentrations lower than 70% (see FIG. 15c). However, at 70% TFE (component concentration 0.625 µM) a relatively large exciplex emission band was observed with $\lambda_{max}$ 480 nm.

Figure 15D:
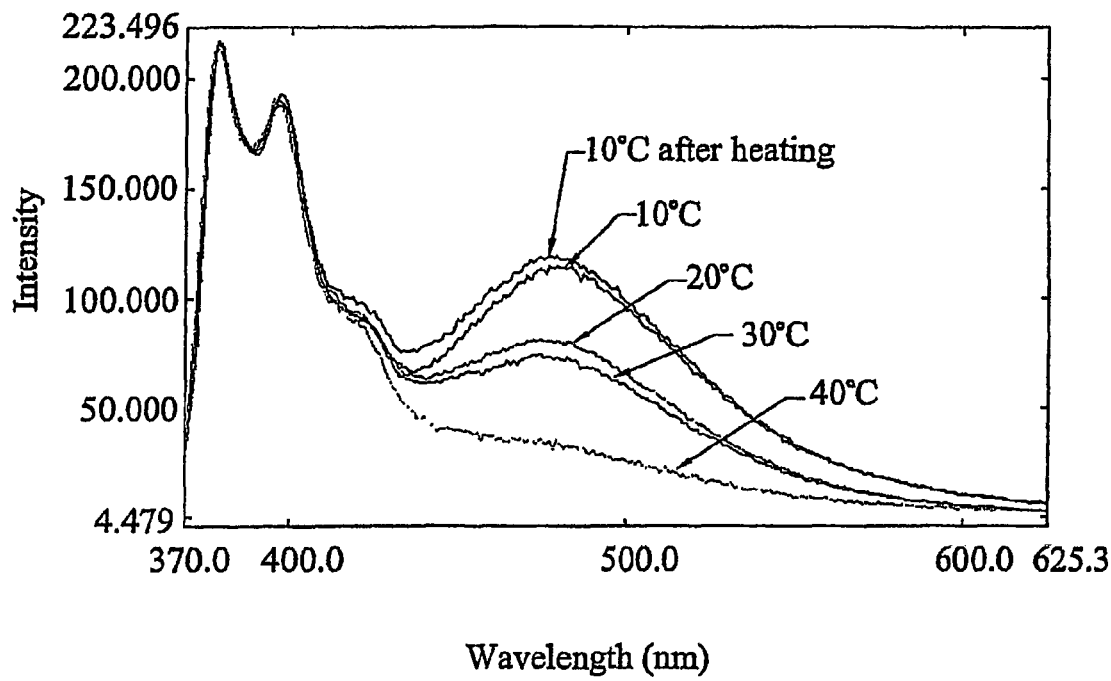
FIG. 15D illustrates the emission spectra of the RNA-BASED SP-19 system in 70% TFE/Tris buffer.
Figure 16:
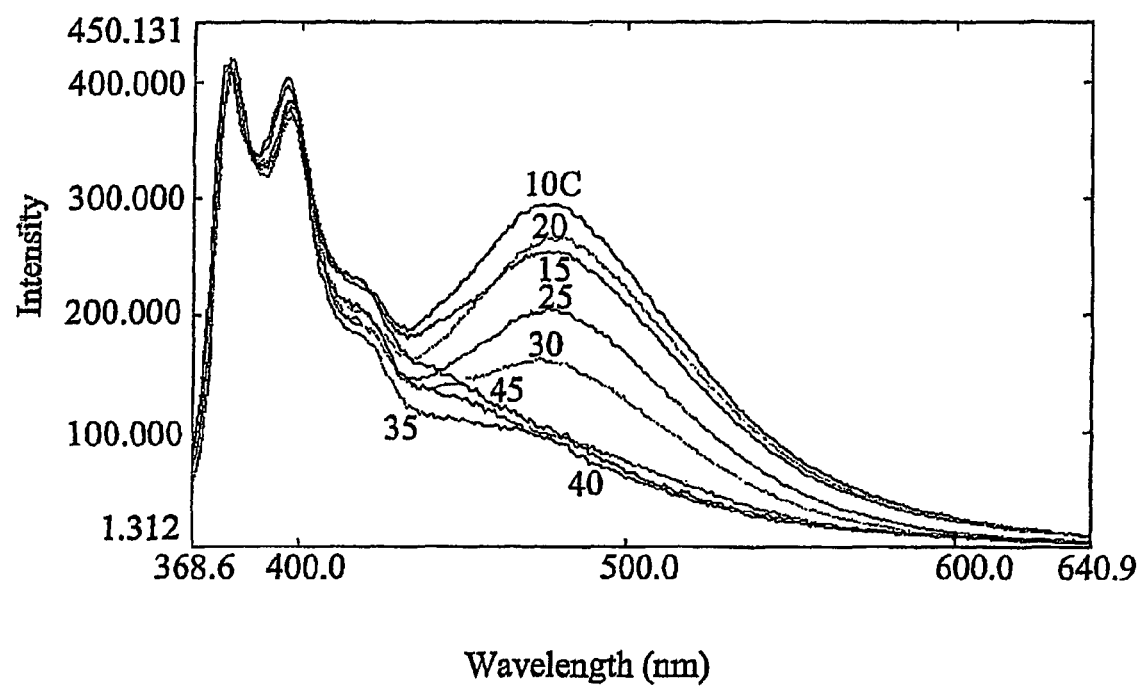
FIG. 16 illustrates melting curves for RNA-based SP-19 in 72% TFE/Tris buffer.

Heating the RNA-BASED SP-19 exciplex system to 40° C. over 30 minutes caused a decrease of the exciplex emission intensity due to melting of the duplex (FIG. 15d). On cooling the system in 80% TFE/Tris (pH 8.5 component concentration 2.5 µM) back to 10° C., the exciplex emission only reappeared on standing for approximately 30 minutes. This part of the study demonstrates the proof-of-principle that split-probe exciplex and excimer detection can be applied to RNA targets as well as to DNA.

EXAMPLE 4

This Example demonstrates variations in exciplex formation dependent on the position and/or number of mismatched or unpaired base pairs between, on the one hand, a 16-mer target DNA sequence and, on the other hand, two 8-mer probes for hybridisation thereto. A series of variants of a 16-mer parent target sequence was used to test the effects of changes at various positions. The parent and variants are shown below, along with nomenclature used for the various constructs. They included a single and a double insertion, each of which would form a gap between the two probes, thereby separating the exci-partners, as well as various single and double mismatches. The 8-mer sequences were chosen so that they were not self-complementary, only bound to the parent in the way required, and were not able to overlap.

The systems tested (i.e. parent and probes) were as follows:

```
Nomenclature        Target sequence

Parent (SP19)       G C C A A A C A-C A G A A T C G
(upper sequence     C G G T T T G T G T C T T A G C
is SEQ ID NO: 1)                  A B Insertion 1         G C C A A A C A G C A G A A T C G
(upper sequence     C G G T T T G T   G T C T T A G C
is SEQ ID NO: 3)                  A   B Insertion 2         G C C A A A C A G T C A G A A T C G
upper sequence      C G G T T T G T     G T C T T A G C
is SEQ ID NO: 4)                  A     B 3' mismatch 1       G C C A A A C A-C A G A A T A G
(upper sequence     C G G T T T G T G T C T T A G C
is SEQ ID NO: 5)                  A B 3' mismatch 2       G C C A A A C A-C A G G A T C G
(upper sequence     C G G T T T G T G T C T T A G C
is SEQ ID NO: 6)                  A B 3' mismatch 3       G C C A A A C A-A G A A T C G
(upper sequence     C G G T T T G T G T C T T A G C
is SEQ ID NO: 7)                  A B 3'-double           G C C A A A C A-C A G G A T G G
mismatch            C G G T T T G T G T C T T A G C
(upper sequence                   A B
is SEQ ID NO: 8)

5'-mismatch 1       G A C A A A C A-C A G A A T C G
(upper sequence     C G G T T T G T G T C T T A G C
is SEQ ID NO: 9)                  A B
5'-mismatch 2       G C C A G A C A-C A G A A T C G
(upper sequence     C G G T T T G T G T C T T A G C
is SEQ ID NO:                     A B
10)
5'-mismatch 3       G C C A A A C T-C A G A A T C G
(upper sequence     C G G T T T G T G T C T T A G C
is SEQ ID NO:                     A B
11)
5'-double           G A C A G A C A-C A G A A T C G
mismatch            C G G T T T G T G T C T T A G C
(upper sequence                   A B
is SEQ ID NO:
12)
```

In the above formulae the exciplex-forming partners are represented by A and B where A=5'P (i.e. pyrene linked to the oligo through the 5' phosphate) and B=3'Np (i.e. a DMN linked to oligo through the 3' phosphate).

Experimental Methods.

Excitation and emission spectra were recorded in the thermostatted cuvette compartment of a Shimadzu RF-5301PC spectrofluorimeter. Spectra were recorded in the "automatic shutter-on" mode to minimize photo-degradation of samples in the cuvette between measurements. Samples were not degassed before measurements.

Spectra were recorded in 10 mM Tris buffer, 0.1 M NaCl, at pH 8.5 in the presence of the appropriate amount of a particular organic co-solvent at 10° C. The ratio of components used was 1:1:1 (Target:5'A:3'B), each at a concentration of 2.5 µM using excitation wavelengths of both 340 nm and 350 nm and slitwidths of 3 or 5 nm, as dictated by the intensity obtained.

Base-line spectra of buffer were taken, and the system components then added individually from stock solutions in the order: 5'-A, then 3'-B, then target (3'-B, 5'-A, target for SP-19). When all components were present, spectra were taken at 3-minute intervals until exciplex emission was maximal. The system was then heated to 40° C. for 2 minutes, and allowed to slowly cool to 10° C. Again spectra were taken at 3-minute intervals until exciplex emission was maximal.

The corresponding buffer base-line spectrum was subtracted from the spectra of the components. Spectra were scaled to monomer pyrene emission at 380 nm to facilitate comparison in excimer or exciplex emission.

If emission of the naphthalene-containing or bis-naphthalene/-containing oligo was sufficiently intensive (~426 nm), this spectral component was recorded first, and then subtracted from the spectrum of the full tandem system. In more detail, the naphthalene-containing oligo-probes normally have emission at ~426 nm. The exciplex band is usually observed around 480 nm. Therefore, the naphthalene-partner may contribute to the emission around 480 nm. To avoid this, the emission spectrum of the naphthalene-containing monomer may be subtracted from the spectrum of the full tandem system in so as to detect only the exciplex signal.

In the case of systems showing only weak exciplex emission, the relative contribution (background) of monomer emission is greater, as there is a tail of emission extending from the 430 nm monomer emission into the region of the exciplex band. For this reason data were quantitated by using only the portion of the exciplex emission above 480 nm. Background can be further lowered, in practice, by using a more stringent (higher) cut-off wavelength with relatively little loss in total detected signal as the band is so broad. Thus, data are presented also with 490 and 500 nm cut-offs to indicate the improvement in signal-to-background thus obtained, and scaled against parent sequence for the 480 nm cut-off to indicate the concomitant sacrifice that must be made in total detected signal.

Figure 17:
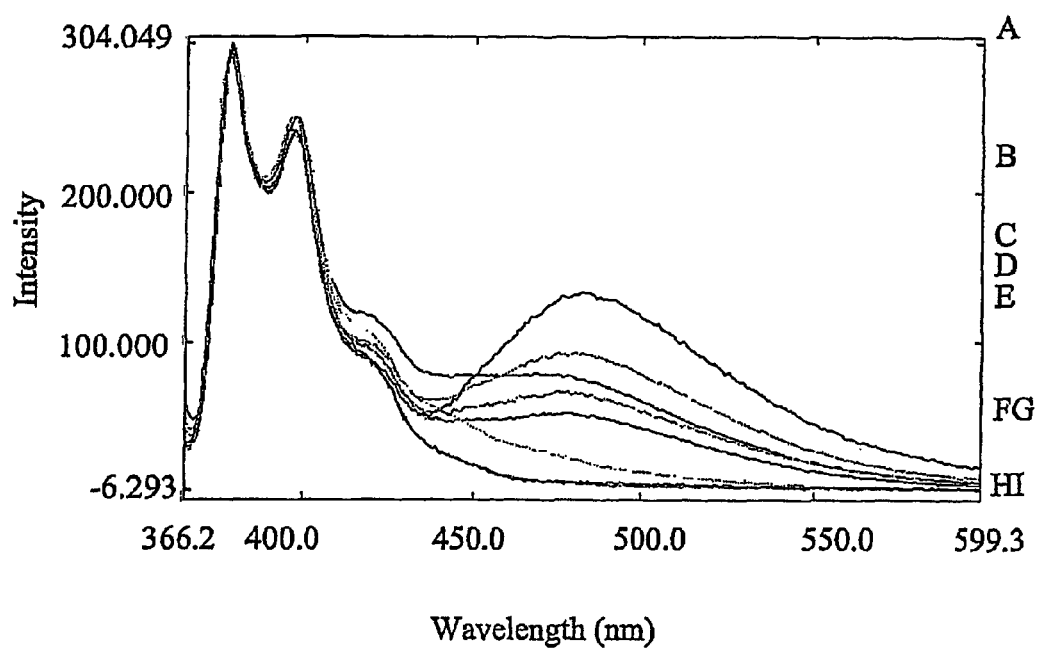
FIG. 17 illustrates emission spectra for the SP-19 exciplex system with mismatch targets before heating.
Figure 18:
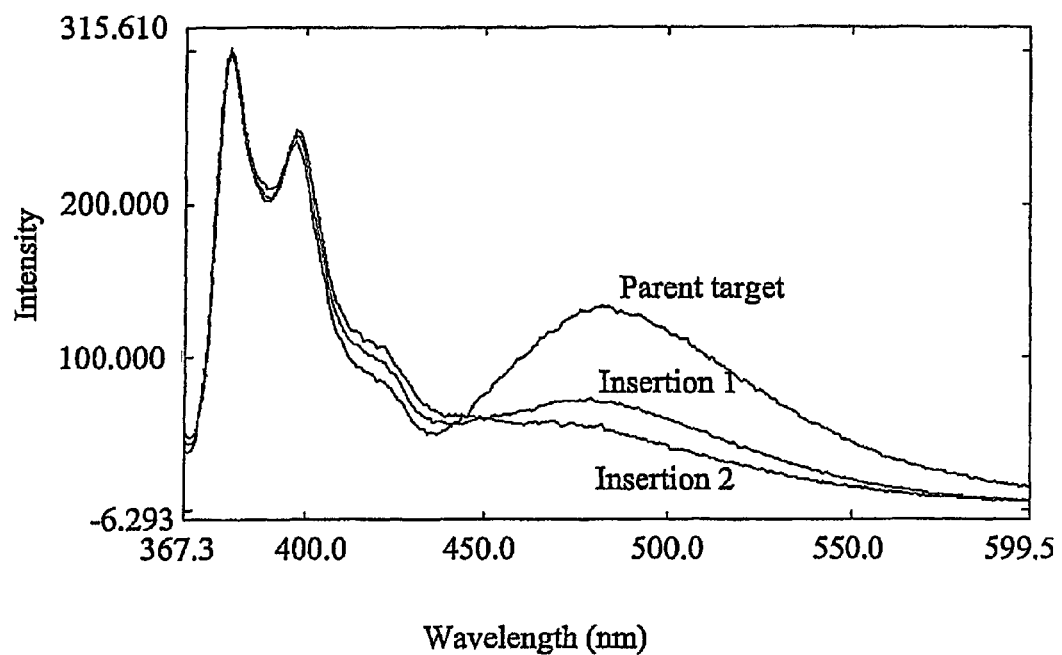
FIG. 18 illustrates emission spectra for SP-19 exciplex system with insertion targets before heating.

The results are shown in FIGS. 17 and 18 which show overlaid emission spectra for the mismatch and insertion targets, respectively, before the heating-cooling protocol.

The data for SP19 were analysed in terms of the emission peak areas with cut-offs of 480, 490 and 500 nm and are shown in Table 2 (before the heating-cooling cycle).

TABLE 2

Areas under emission curves for parent and insertion/mismatch sequences for split-probe exciplex system I (SP19) with detection windows of 480-600, 490-600 and 500-600 nm. The mutant/parent ratios given are scaled against the data for the parent sequence using 480-600 nm detection window.

|  | Area before heating. | | | Mutant/parent(480-600) | | |
| --- | --- | --- | --- | --- | --- | --- |
|  | 480-600 nm | 490-600 nm | 500-600 nm | 480-600 | 490-600 | 500-600 |
| Parent | 7879 | 6585 | 5326 | 1.00 | 0.83 | 0.68 |
| Insertion 1 | 2752 | 2245 | 1800 | 0.35 | 0.28 | 0.23 |
| Insertion 2 | 3775 | 3087 | 2459 | 0.48 | 0.39 | 0.31 |
| 3'mismatch 1 | 3762 | 3033 | 2386 | 0.48 | 0.38 | 0.30 |

TABLE 2-continued

Areas under emission curves for parent and insertion/mismatch sequences for split-probe exciplex system I (SP19) with detection windows of 480-600, 490-600 and 500-600 nm. The mutant/parent ratios given are scaled against the data for the parent sequence using 480-600 nm detection window.

| | Area before heating. | | | Mutant/parent(480-600) | | |
|---|---|---|---|---|---|---|
| | 480-600 nm | 490-600 nm | 500-600 nm | 480-600 | 490-600 | 500-600 |
| 3'mismatch 2 | 2500 | 2027 | 1599 | 0.32 | 0.26 | 0.20 |
| 3'mismatch 3 | 5035 | 4128 | 3298 | 0.64 | 0.52 | 0.42 |
| 3'double mismatch | 247 | 204 | 174 | 0.03 | 0.03 | 0.02 |
| 5'mismatch 1 | 736 | 555 | 418 | 0.09 | 0.07 | 0.05 |
| 5'mismatch 2 | 686 | 549 | 437 | 0.09 | 0.07 | 0.06 |
| 5'mismatch 3 | 3471 | 2839 | 2266 | 0.44 | 0.36 | 0.29 |
| 5'double mismatch | 330 | 277 | 233 | 0.04 | 0.04 | 0.03 |

Considering the parent sequence, it is clear from both procedures that there is a loss of sensitivity of 17% on using the 490 nm cut-off and of 32-33% using the 500 nm cut-off. The use of the higher wavelength cut-offs does not alter the qualitative evaluation of whether a detectable signal arises for a particular mismatch/insertion. From the spectra (FIGS. 17 and 18) there are no significant exciplex emissions for 3' double mismatch, 5' mismatch1, 5' mismatch2 or 5' double mismatch. The conclusion that these 4 systems give no detectable signal in the exciplex band region is independent of the detection window. No other mismatch/insertion systems are close to the borderline of undetectable signal. Thus, the use of higher wavelength cut-offs does not bring any increased discrimination to the system in this particular case.

By way of comparison, the excimer forming analogues based on SP-1 of the above parent/insertion/mismatch systems were produced. The above procedures were then repeated for these excimer systems and the results are shown in Table 3 below.

TABLE 3

Areas under the excimer emission curves (480-600 nm) and ratios of mutant: parent curves and corresponding insertion/mismatch systems.

| | Area before heating. | Mutant/parent |
|---|---|---|
| Parent | 10933 | 1.00 |
| insertion 1 | 2975 | 0.27 |
| insertion 2 | 2353 | 0.22 |
| 3'mismatch 1 | 3926 | 0.36 |
| 3'mismatch 2 | 3857 | 0.35 |
| 3'mismatch 3 | 7053 | 0.65 |
| 3'double mismatch | 235 | 0.02 |
| 5'mismatch 1 | 440 | 0.04 |
| 5'mismatch 2 | 4355 | 0.40 |
| 5'mismatch 3 | 7857 | 0.72 |
| 5'double mismatch | 350 | 0.03 |

Figure 19A:
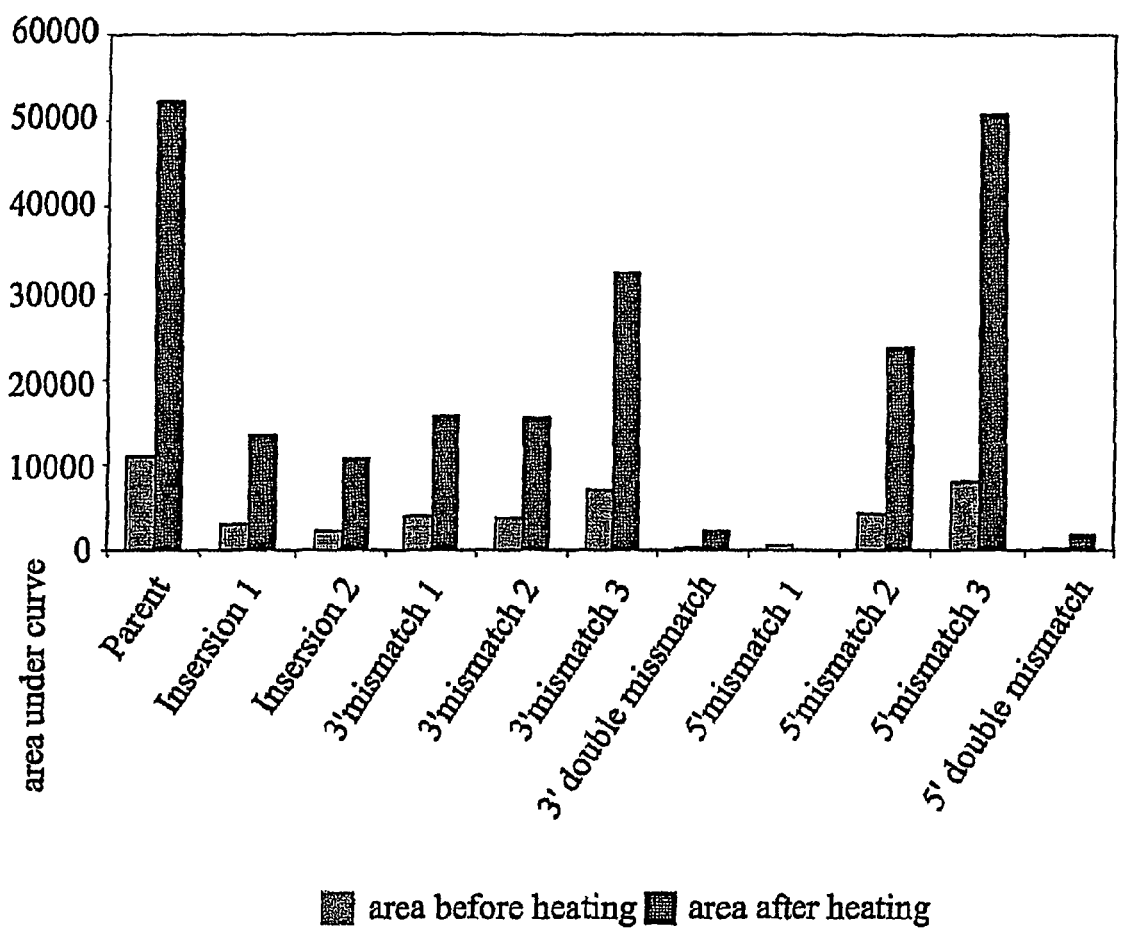
FIGS. 19A and 19B provide a graphical comparison of the data shown in Tables 2 and 3, respectively.
Figure 19B:
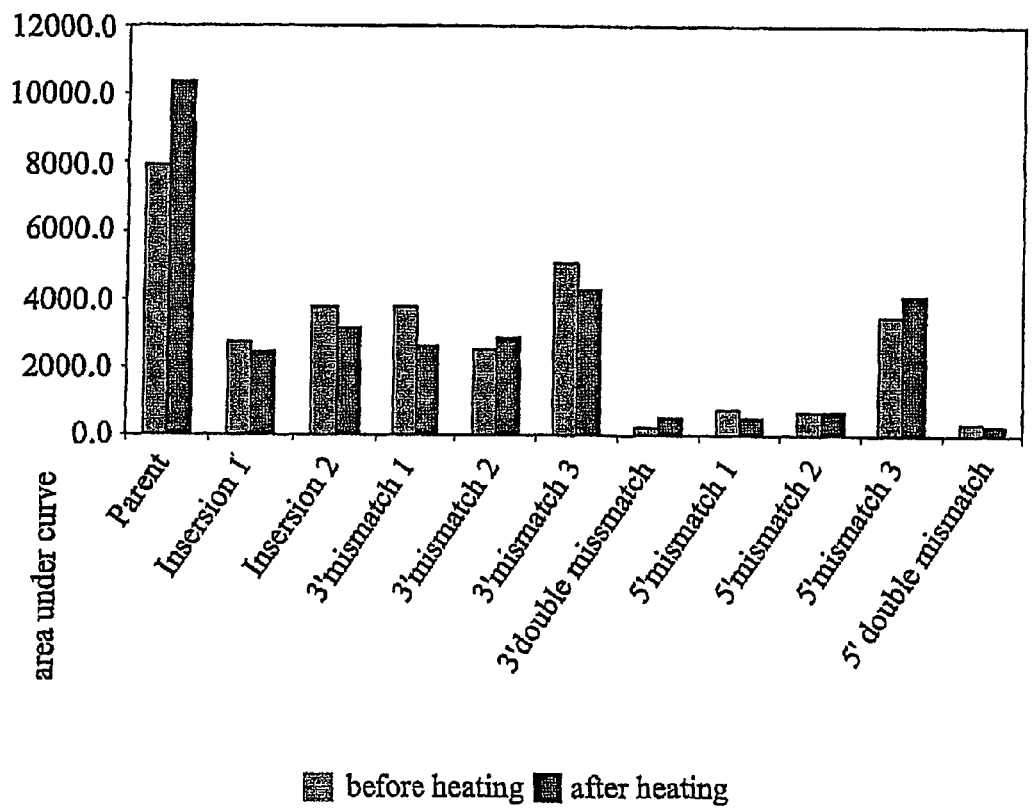

A graphical comparison of the data shown in Tables 2 and 3 is presented in FIGS. 19A and 19B respectively of the accompanying drawings. FIGS. 19A and 19B additionally incorporate data obtained after heating the system evaluated to 40° C. and slowly cooling to 10° C.

In comparison to the excimer system (Table 3), the exciplex system is surprising in that it detects the presence of a single mismatch for 5'mismatch 1 and 5'mismatch 2, whereas the excimer system only detected 5'mismatch 1. Both excimer and exciplex system I detected the double mismatch targets (3' and 5'). Neither system detected single mismatches in the 3'-probe region.

Comparison with Published Information for Excimer-Based Split-Probe Systems

Split-probe systems based on excimer fluorescence have been described by Ebata et al in:

Ebata, K.; Masuko, M.; Ohtani, H.; Kashiwasake-Jibu, M. *Photochem. Photobiol.* 1995, 62, 836-839.

Ebata, K.; Masuko, M.; Ohtani, H.; Kashiwasake-Jibu, M. *Nucleic Acid Symp. Ser.* 1995, 34, 187-188.

Masuko, M.; Ohtani, H.; Ebata, K.; Shimadzu, A. *Nucleic Acids Res.* 1998, 26, 5409-5416.

Ebata attached pyrene to the 5'-terminus of one oligo probe and to the 3'-terminus of the other. The probes bound to contiguous regions of the target, bringing the pyrene molecules into close proximity.

Hybridisation was carried out in phosphate buffer containing 20% v/v DMF. As target concentration increased excimer fluorescence increased and monomer fluorescence decreased. The opposite effect was seen on heating. If one probe lacking a pyrene group was used no excimer fluorescence was seen. From this evidence it was concluded that the effect on the fluorescence spectrum was due to excimer formation between the two pyrene groups, and not due to intercalation or base stacking interactions between pyrene and the nucleobases. Melting curve experiments and CD spectral evidence also supported the fact that pyrene did not interact with the duplex. Intercalation would stabilise the duplex, raising the $T_m$. However, the $T_m$ value was not appreciably affected and the CD spectrum showed that pyrene was not in a chiral environment, suggesting no interaction with the helix. For targets containing one or two extra nucleotides in the centre of the target, which separated the two probes, excimer emission decreased suggesting that the pyrene molecules need to be close. In fact, the distances between bases in a B-DNA helix is ~3.4 Å, which corresponds to the interplanar distance of pyrene dimers in crystals. Excimer emission was affected by the percentage DMF, showing a maximum emission at 30-40% v/v DMF. It was thought that the organic solvent could increase quantum efficiency due to pyrene-solvent dipole-dipole interactions or, by preventing intercalation into the helix. Sodium ion concentration was also seen to affect excimer intensity, which peaked at 0.1 M NaCl. Sodium ions exert their effect indirectly by affecting duplex formation. The length of the linkers also affected excimer intensity, which was greatest when a shorter linker was used.

A similar excimer split-probe system using two contiguously binding probe oligos was employed by Paris et al. (Paris, P. L.; Langenhari, J. M.; Kool, E. T. *Nucleic Acids Res.* 1998, 26, 3789-3793), who attached pyrene directly to the ribose sugar, replacing the natural DNA bases. Five different probe pairs were studied, each having different spacing between the pyrene groups. This was achieved by inserting or removing nucleotide residues in the probe sequences, as below. For all the probe systems tested, addition of the target caused quenching of monomer emission, and the appearance of an exciplex band around 490 nm. The N-2 spacing was found to give the best excimer: monomer ratio (intensity of excimer fluorescence at 490 nm: intensity of monomer emission at 398 nm). In this study excimer emission was detected in PIPES buffer without organic solvent. The system was also able to distinguish between a perfectly matched target and one possessing a mismatch along the binding site of one probe, with mismatched targets giving no excimer emission.

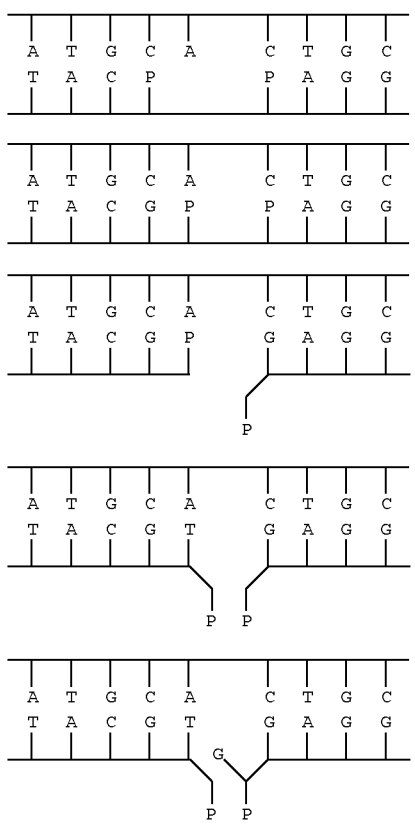

EXAMPLE 5

Effects of Some PCR Additives on Exciplex Emission.

The effect of several PCR additives (sulfolane, methyl sulfone, betaine and DMSO—see formula below on exciplex emission was investigated using the SP-19 system (ON1-5'P+ON2-3'Np+DNA target strand) in Tris buffer (10 mM Tris, 0.1 M NaCl, pH 8.5) in the absence of TFE and in 80% TFE/Tris buffer at pH 8.5.

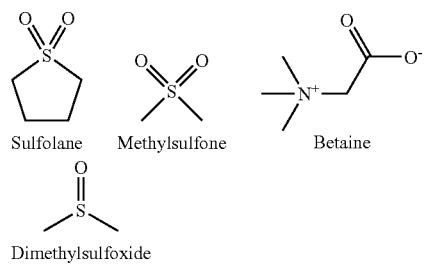

For the experiments in TFE/Tris buffer the system was formed first in 80% TFE/Tris buffer in the absence of additive, then after spectra had been taken the PCR additive was added from a stock solution and spectra taken. Having the additive present before the formation of the system gave similar results to those obtained when the system was formed in 80% TFE/Tris buffer followed by additive addition, therefore, these data have not been shown. All experiments were preformed at 10° C.

Tris Buffer

Figure 22:
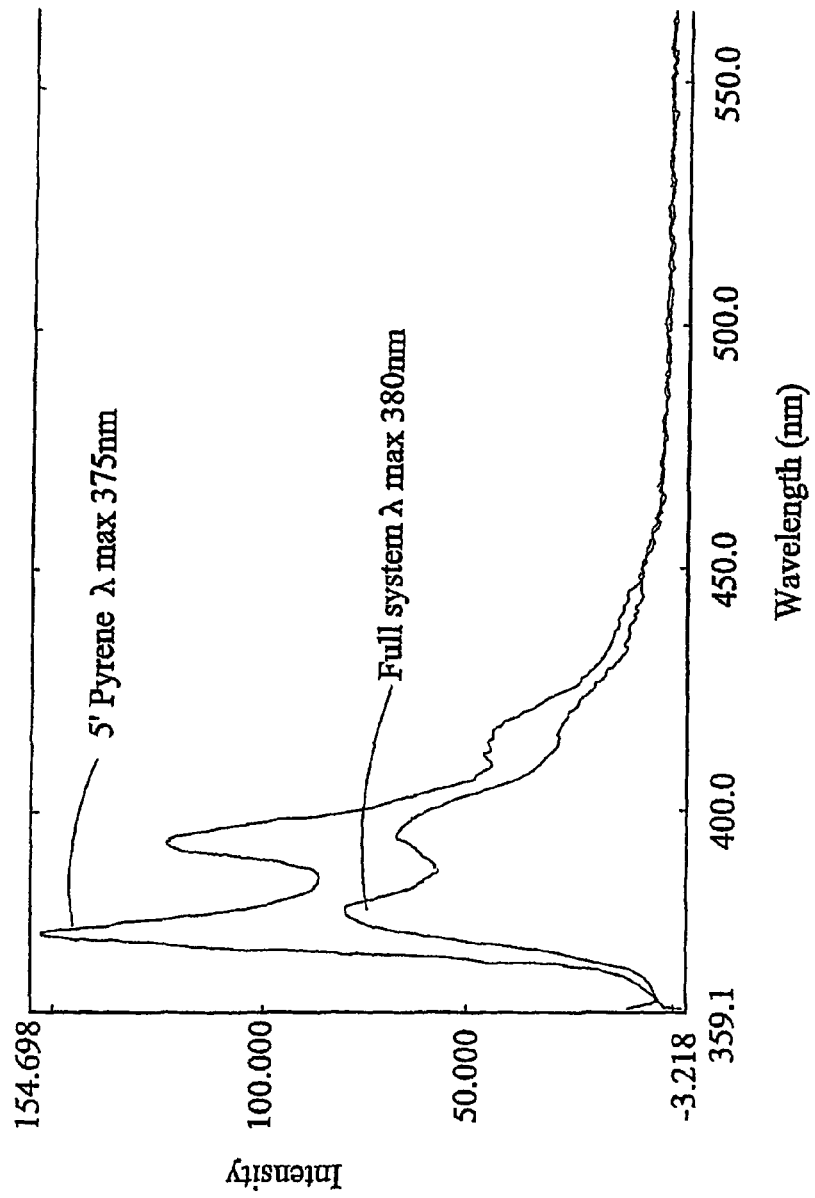
FIG. 22 illustrates the emission spectra of ON1-5' pyrene and ON2-3' Naphthalene in the presence of target strand in Iris buffer and in the presence of sulfolane.

Irrespective of the additive and concentration used, the emission spectra of ON1-5'T+ON-2-3N'P (naphthalene signal subtracted) showed a $\lambda_{max}$ of 375 nm. On addition of the DNA target strand to the two probe components the emission maximum was red-shifted by a few nanometers, accompanied by a drop in emission intensity indicating that duplex formation had occurred. No exciplex emission was seen for this system in the presence of any of the additives tested in Tris buffer, see FIG. 22. The magnitude of the shift in $\lambda_{max}$ and the decrease in intensity on addition of the target, shown in Table 4, depended on the additive used and its concentration. On average a 45% drop in intensity was seen. Generally, the larger the drop in intensity, the larger the shift in $\lambda_{max}$. In addition the higher the concentration of a particular additive the smaller the drop and the shift in $\lambda_{max}$.

TABLE 4

Values of $\lambda_{max}$ and percentage drop in intensity on addition of the target strand to ON1-5'P and ON-2-3N'P in Tris buffer (10 mM Tris, 0.1 M NaCl, pH 8.5 at 10° C.) in the presence of various PCR additives. Excitation wavelength 350 nm, slit width 5 nm.

| Additive and concentration | $\lambda_{max}$(nm) ON1-5'P + ON-2-3N'P | $\lambda_{max}$(nm) ON1-5'P + ON-2-3N'P | Percentage drop in intensity on binding |
|---|---|---|---|
| 10% DMSO | 375 | 376 | 40.9 |
| 1 M Betaine | 375 | 377 | 52.2 |
| 2 M Betaine | 375 | 376 | 34.0 |
| 0.6 M Methylsulfone | 375 | 379 | 51.6 |
| 1.1 M Methylsulfone | 375 | 377 | 44.9 |
| 0.15 M Sulfolane | 375 | 380 | 48.4 |
| 0.5 M Sulfolane | 375 | 378 | 42.4 |

Effect on Split-Probe Fluorescence of PCR Additives in 80% TFE/Tris Buffer (10 mM Tris, 0.1 M NaCl, pH 8.5).

Betaine

Figure 23:
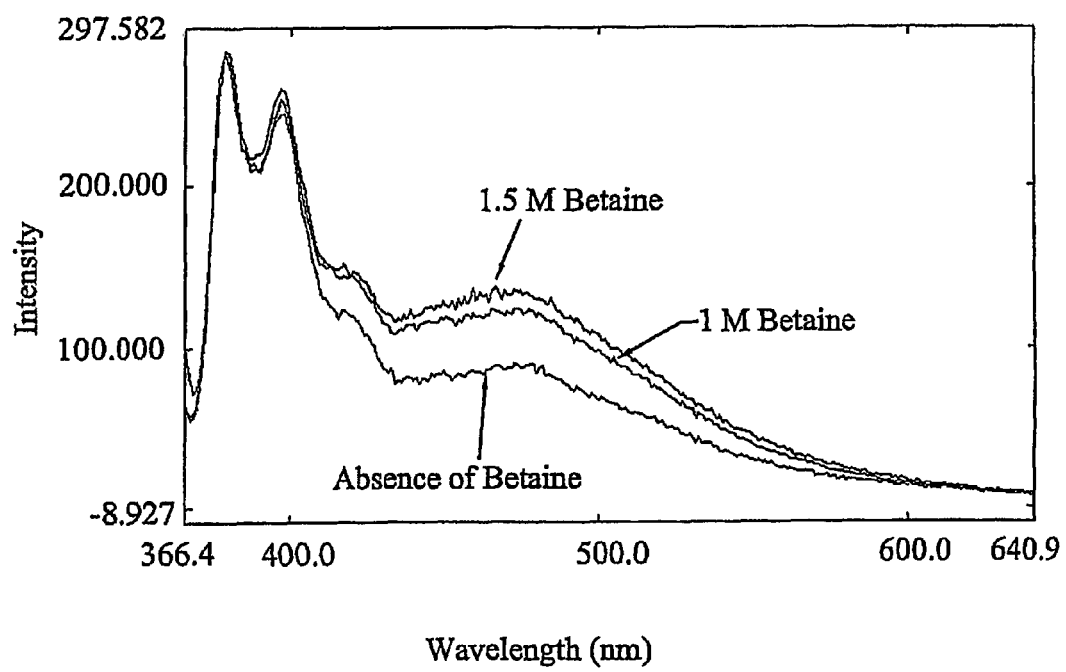
FIG. 23 illustrates the emission spectra for the SP-19 system in 80% TFE/Tris buffer in the presence of 0.1 and 1.5 M betaine and in the absence thereof.

FIG. 23 shows the emission spectra for SP-19 in 80% TFE/Tris buffer (10 mM Tris, 0.1 M NaCl, pH 8.5) at 10° C. in the presence of 0.1 and 1.5 M betaine. In the absence of betaine in 80% TFE/Tris buffer the exciplex signal observed on formation of the full split-probe system, increased to a maximum over 10 minutes to give an $I_E/I_M$ of 0.33. On addition of betaine from stock solution (200 μl stock solution to 2 ml 80% TFE/Tris buffer containing SP-19 system) at this point to give a concentration of 1 M betaine the exciplex signal was seen to increase by a further 33% ($I_E/I_M$ 0.44). Further addition of betaine from the stock solution (100 µl to the cuvette, to give 1.5 M betaine) resulted in an even further increase in the exciplex: monomer ratio to give an $I_E/I_M$ of 0.48 (46% increase.). In all cases the $\lambda_{max}$ value of emissions for the monomer and exciplex were unaffected by betaine: the monomer band showed a $\lambda_{max}$ value of 379 nm and the exciplex band had $\lambda_{max}$ 474 nm. Heating the system to 40° C. and re-cooling to 10° C. gave no appreciable change in $I_E/I_M$.

Sulfolane

Figure 24:
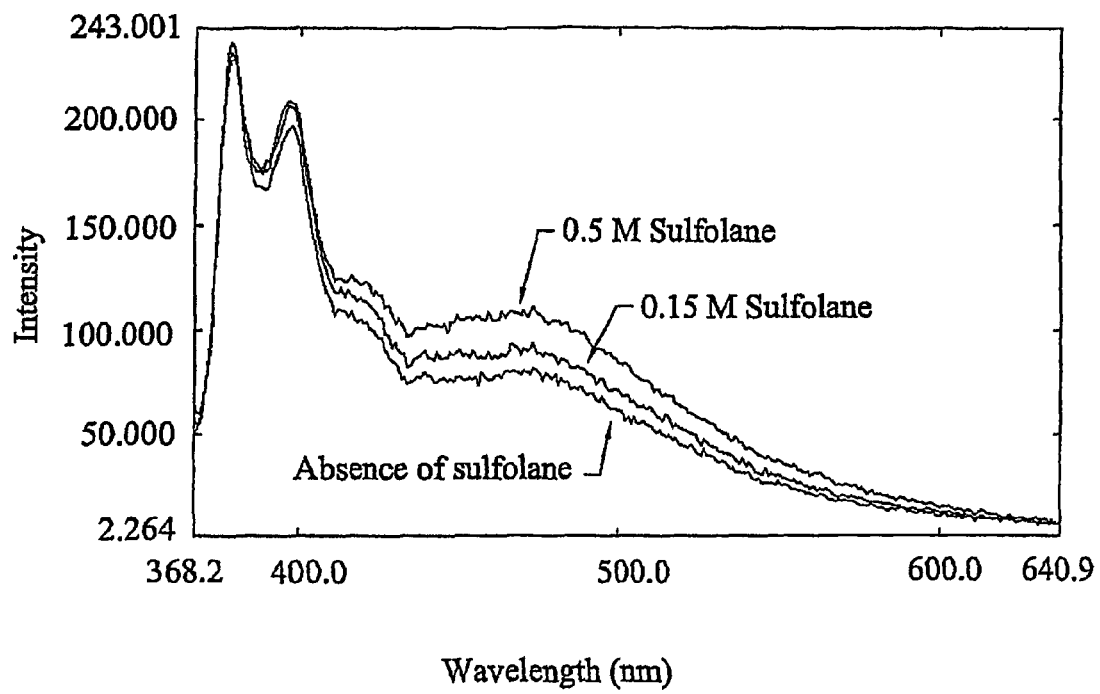
FIG. 24 illustrates the emission spectra for the SP-19 system in 80% TFE/Tris buffer in the presence of 0.15 and 0.5 M sulfolane and in the absence thereof.

On formation of the SP-19 system in 80% TFE/Tris buffer (10 mM Tris, 0.1 M NaCl, pH 8.5) the exciplex signal had a $\lambda_{max}$ value of 473 nm, the monomer signal had an emission maximum at 376 nm and the $I_E/I_M$ value was 0.34. On addition of sulfolane (30 µl added to the cuvette from a stock solution to give 0.15 M), the exciplex signal increased by approximately 20% ($I_E/I_M$ 0.40) (see FIG. 24). Further addition of sulfolane (a further 70 µl added to the cuvette from the stock solution to give 0.5 M) resulted in a further increase in exciplex emission intensity (FIG. 24) to give an $I_E/I_M$ of 0.46 (about a 35% increase relative to the signal in the absence of sulfolane). The emission maxima of monomer and exciplex bands were not affected by the addition or concentration of sulfolane, remaining at 379 nm and 473 nm, respectively. Heating the system to 40° C. and cooling back to 10° C. did not greatly affect the value of $I_E/I_M$.

Methylsulfone.

Figure 25:
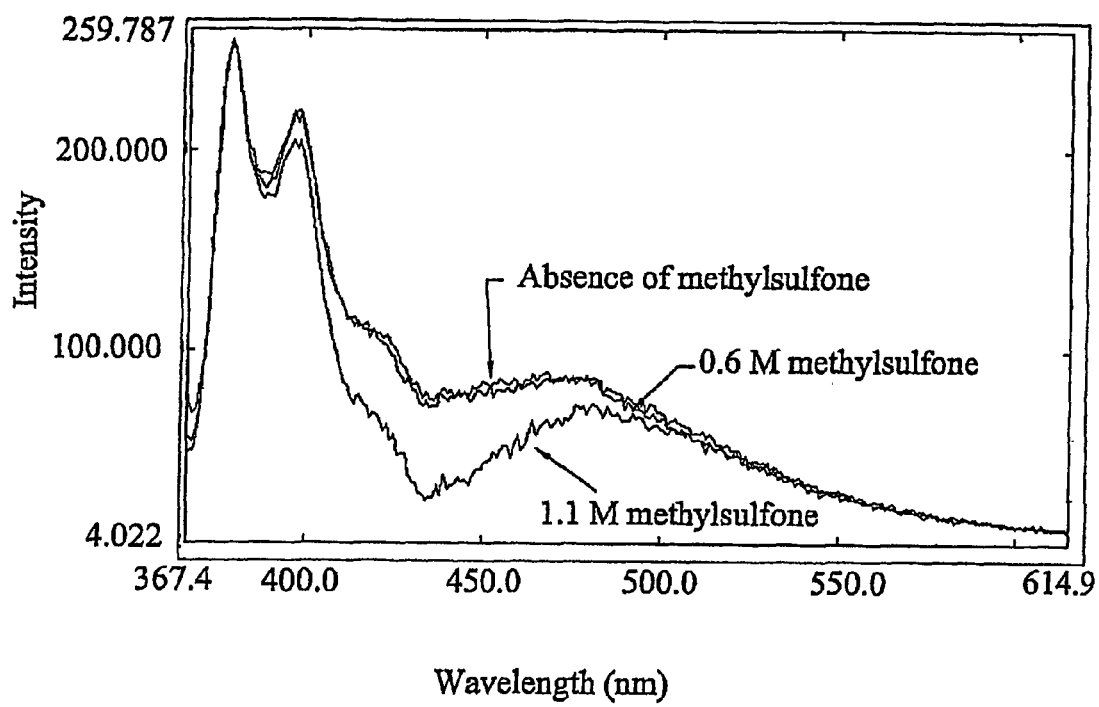
FIG. 25 illustrates the emission spectra for the SP-19 system in 80% TFE/Tris buffer in the presence of 0.6 and 1.1 M Methylsulfone and in the absence thereof.

Addition of methylsulfone to the full SP-19 system actually reduced the value of $I_E/I_M$. On formation of the full system in 80% TFE/Tris buffer (10 mM Tris, 0.1 M NaCl, pH 8.5) at 10° C. the exciplex band ($I_E/I_M$) of 0.34 was observed on irradiation at 350 nm. The emission spectra (FIG. 25) showed $\lambda_{max}$ 379 nm for the monomer band and 472 nm for the exciplex band. On addition of methylsulfone, (240 µl was added to the cuvette to give a 0.6 M), the spectrum appeared unchanged in intensity and emission maxima. Further addition of sulfolane to 1.1 M (a further 200 µl stock solution was added to the cuvette) caused the exciplex emission band intensity to decrease relative to the monomer band ($I_E/I_M$ 0.28). A shift in the $\lambda_{max}$ value of the exciplex band from 472 to 479 nm was also observed, with $\lambda_{max}$ for the monomer band remaining unchanged (see FIG. 25).

Dimethylsulfoxide.

Figure 26:
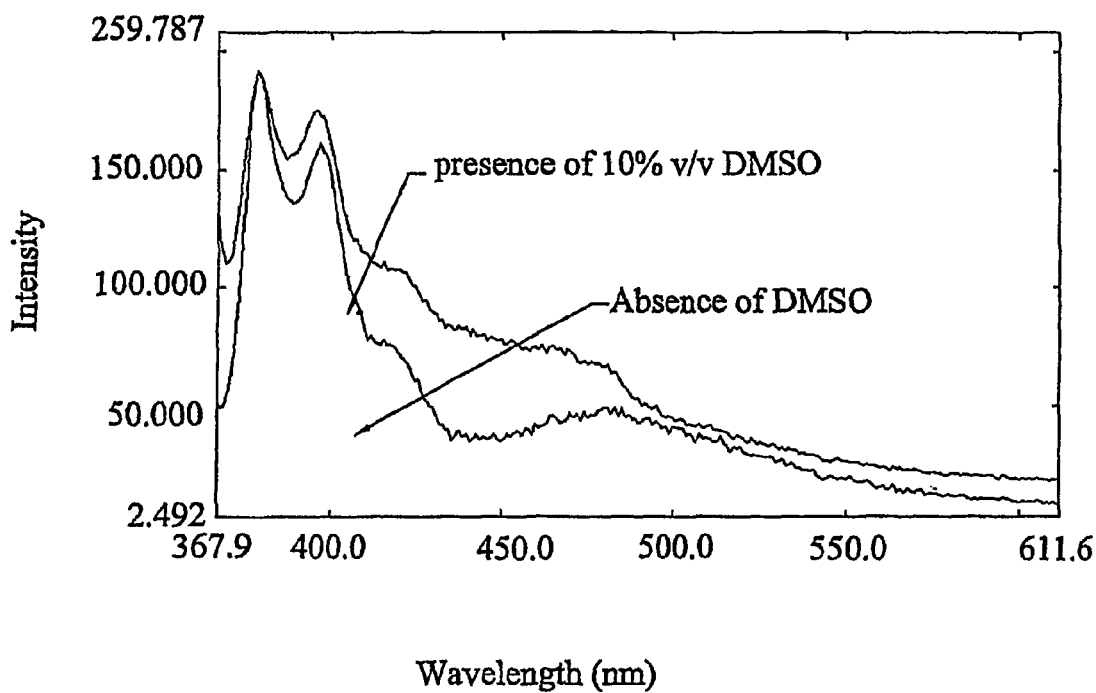
FIG. 26 illustrates the emission spectra for the SP-19 system in 80% TFE/Tris buffer in the presence of 1.41M DMSO and in the absence thereof.

The addition of DMSO to a level of 10% (1.41 M), to the SP-19 system did not improve the exciplex signal, see FIG. 26. On initial formation of the system in 80% TFE/Tris buffer (10 mM Tris, 0.1 M NaCl, pH 8.5) at 10° C. the exciplex band was observed with $\lambda_{max}$ 480 nm and $I_E/I_M$ of 0.26. However on addition of DMSO (10%) the exciplex band altered to appear as a shoulder poorly resolved from the monomer band, the emission maximum of which remained unchanged (379 nm). Heating the system to 40° C. and subsequent cooling back to 10° C. failed to resolve the exciplex signal.

Of the additives tested betaine and sulfolane were found to actually increase exciplex emission relative to monomer emission in 80% TFE/Tris buffer methylsulfolane and DMSO did not give any desirable effects, methylsulfolane decreased the emission intensity and DMSO decreased the resolution of the exciplex band. In all cases heating and reannealing of the system did not give a marked effect on the emission spectra and therefore these data have not been shown along with the pre-heating data.

EXAMPLE 6

This Example provide a study of the SP-3, and SP-38 systems.

SP-3 Split-Probe System in Tris Buffer/80% TFE at 10° C.

Figure 29:
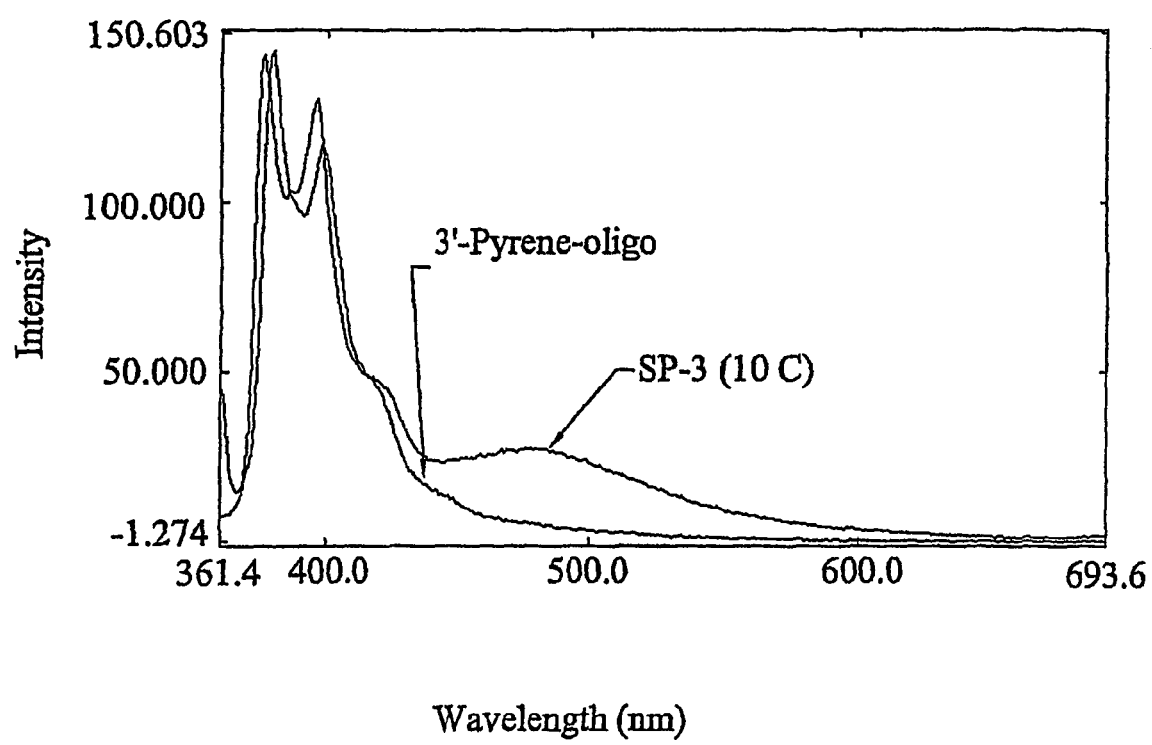
FIG. 29 illustrates the emission spectra of the SP-3 split-probe system in 80% TFE/Tris butter.

Tris buffer contained 0.1M NaCl, 0.01M Tris, pH 8.4 Excitation wavelength was 340 nm for the ON2-3'Pyrene and 350 nm for the SP-3. Spectra were baseline corrected and scaled against the monomer signal. Concentration of oligonucleotide components was 2.5 µM. The results are shown in FIG. 29.

Emission Spectra of SP-38 Split-Probe System and its Components Recorded in Tris Buffer/80% TFE at 10° C.

Tris buffer contained 0.1M NaCl, 0.01M Tris, pH 8.4. Excitation wavelength was 440 nm (slit 1.5) for ON1-5'Perylene and 464 nm (slit 3) for the complexes. Spectra were baseline corrected and scaled against the monomer signal. Concentration of oligonucleotide components was 2.5 µM.

Figure 30:
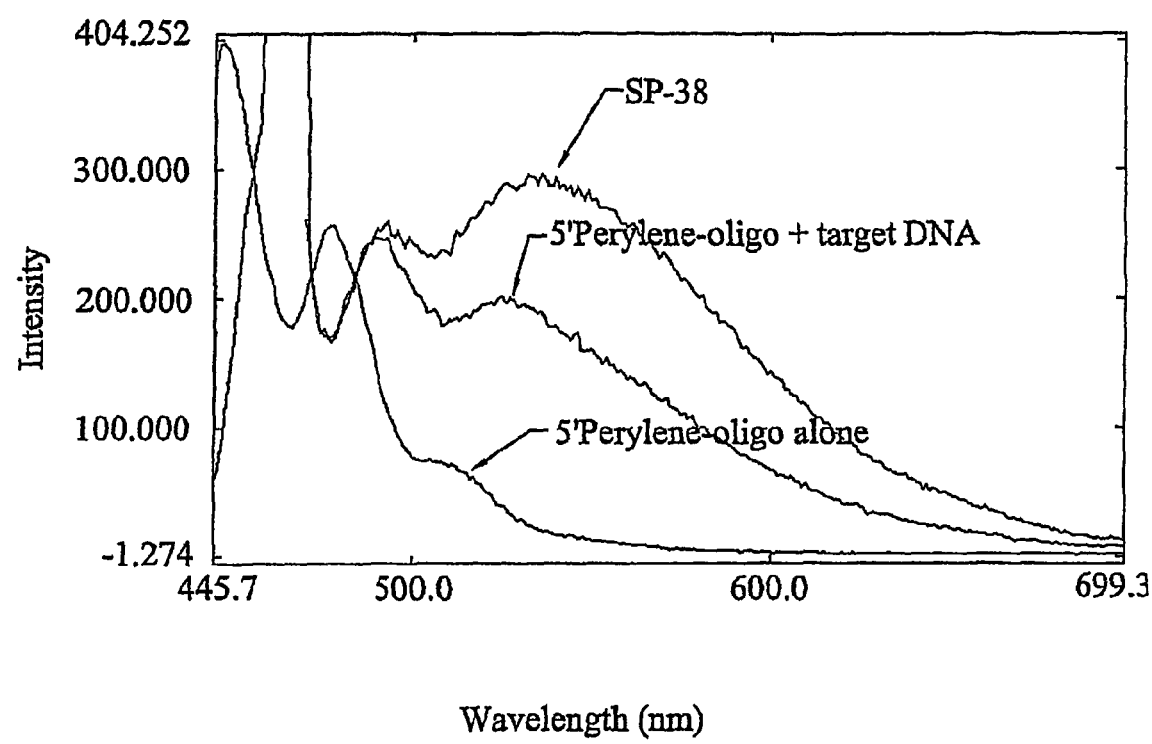
FIG. 30 illustrates the emission spectra of the SP-38 split-probe system compared with those for the 5' Pryene oligo and 5'Pryene oligo+target DNA, the spectra being recorded in 80% TFE/Tris buffer.

The results are shown in FIG. 30.

FIG. 30 shows that hybridization of ON1-5'Perylene derivative with the target DNA results in 10 nm red-shift of excitation and emission maximums indicating the interaction between chromophore and DNA duplex. Also, the background signal resulted from perylene-DNA exciplex formation was observed (black curve). The addition of second partner, containing bis-naphthalene derivative, induces further increase of exciplex signal.

EXAMPLE 7

The SP-2 system was investigated using techniques as described above and the results compared with those for the ON2-3'Pyrene. The spectra were recorded in Tris Buffer/80% TFE at 10° C. The excitation wavelength was 340 nm for the ON2-3'Pyrene and 350 nm for the SP-2; slit 3 was used. Tris buffer contained 0.1M NaCl, 10 mM Tris, pH 8.4. Concentration of oligonucleotide components was 2.5 µM. Spectra were baseline corrected and scaled against the monomer signal.

The spectra of SP-2 after heating to 40° C. and cooling back to 10° C. was also recorded.

Figure 31:
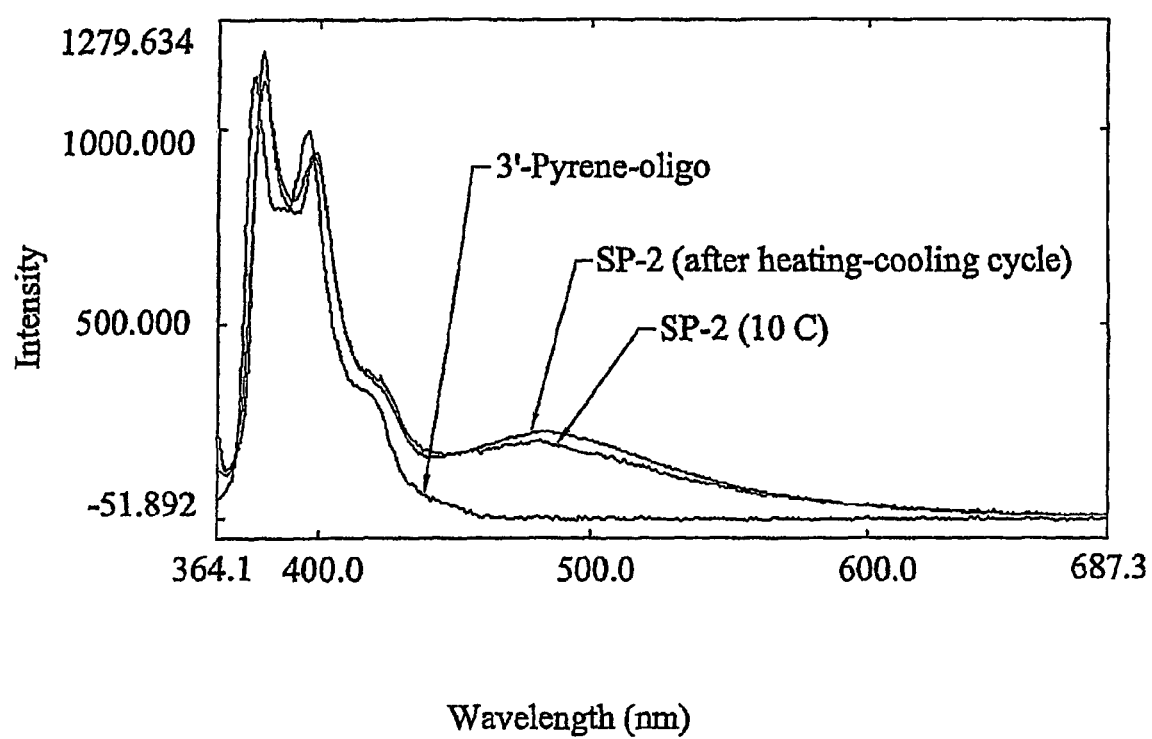
FIG. 31 illustrates the emission spectra of the SP-2 split-probe system compared with those for the ON2-3' Pryene oligo, the spectra being recorded in 80% TFE/Tris buffer.

The results are shown in FIG. 31. Once again, an Exciplex signal was observed for SP-2, the signal being enhance after heating and subsequent cooling.

EXAMPLE 8

This Example investigates hybridisation for a construct in which one of the probes contains 3 LNA residues.

The construct investigated was based on the SP-19 system but in which the probes were as follows:

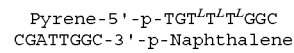

Spectra were recorded in Tris Buffer/80% TFE at 10° C. The Tris Buffer contained 0.1M NaCl, 10 mM Tris, pH 8.3. Concentration of oligonucleotide components was 2.5 µM for all oligonucleotides.

Figure 32:
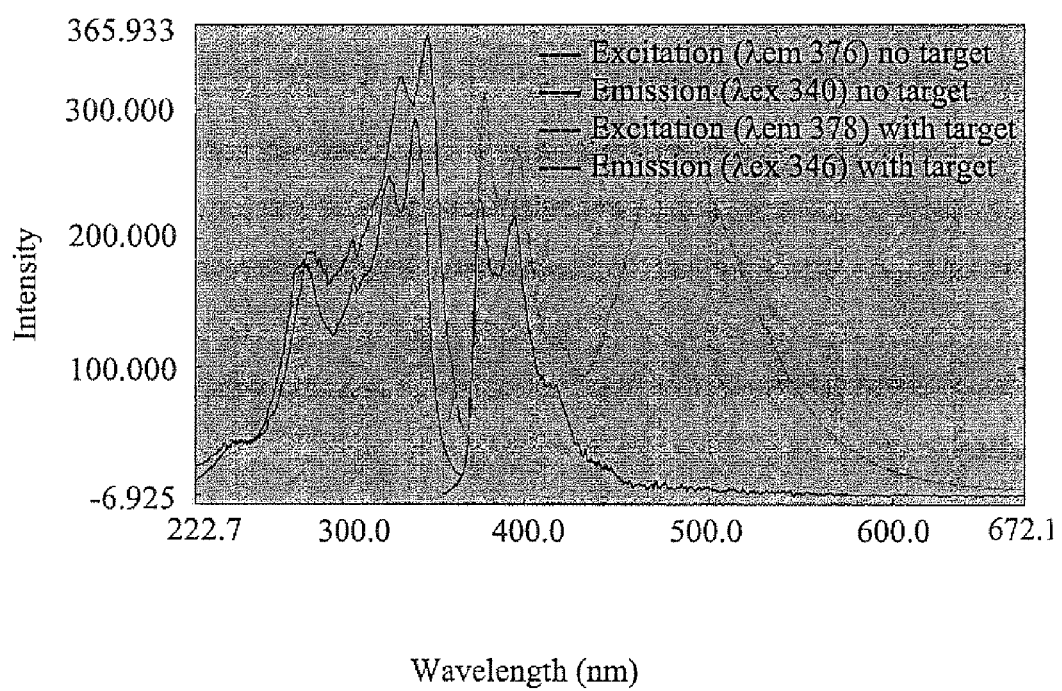
FIG. 32 illustrates the emissions spectra for a construct based on the SP-19 system but in which one of the probes contained 3 LNE residues, the spectra being recorded in 80% TFE/Tris buffer.

The results are shown in FIG. 32.

This figure shows the strong exciplex fluorescence at approx 490 nm from the perfect complement of the target used for SP-19 in the DNA studies described in Example 1 above (the probe oligos here had 3 LNA residues as indicated in the pyrene-bearing probe oligo, shown as $T^L$). In comparison with use of a fully DNA-based probe oligo the exciplex fluorescence intensity is greater for this $SL^3$19 LNA-based oligo probe.

The above procedure was repeated but by introducing a mismatch into the oligo probe containing LNA. The probes used for this investigation are shown below:

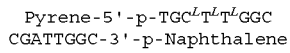

Figure 33:
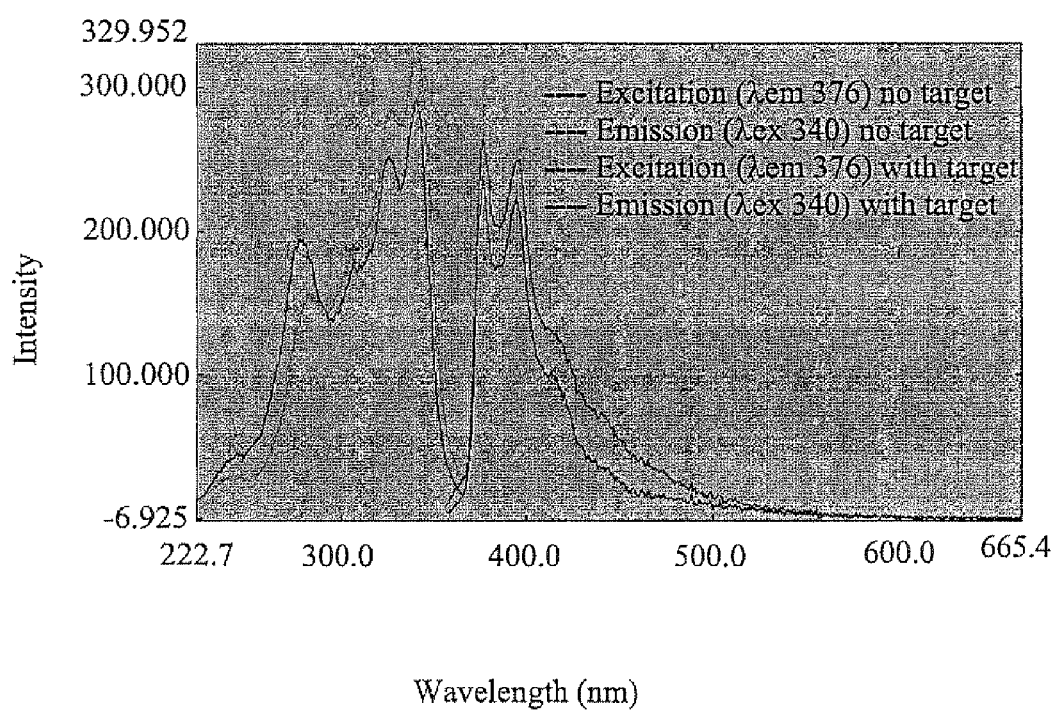
FIG. 33 illustrates the emission spectra for a construct based on the SP-19 system but in which one of the probes contained 3 LNE residues and had a mismatch for the target, the spectra being recorded in 80% TFE/Tris buffer.

The results of this investigation are shown in FIG. 33 which shows that the difference in signal between wild-type (the perfect compliment) is much greater than is the case of SP-19 itself, which is an all DNA-based system.

Appendix 1

Attachment of 1-pyrenemethylamine to oligonucleotide probes

Figure 27:
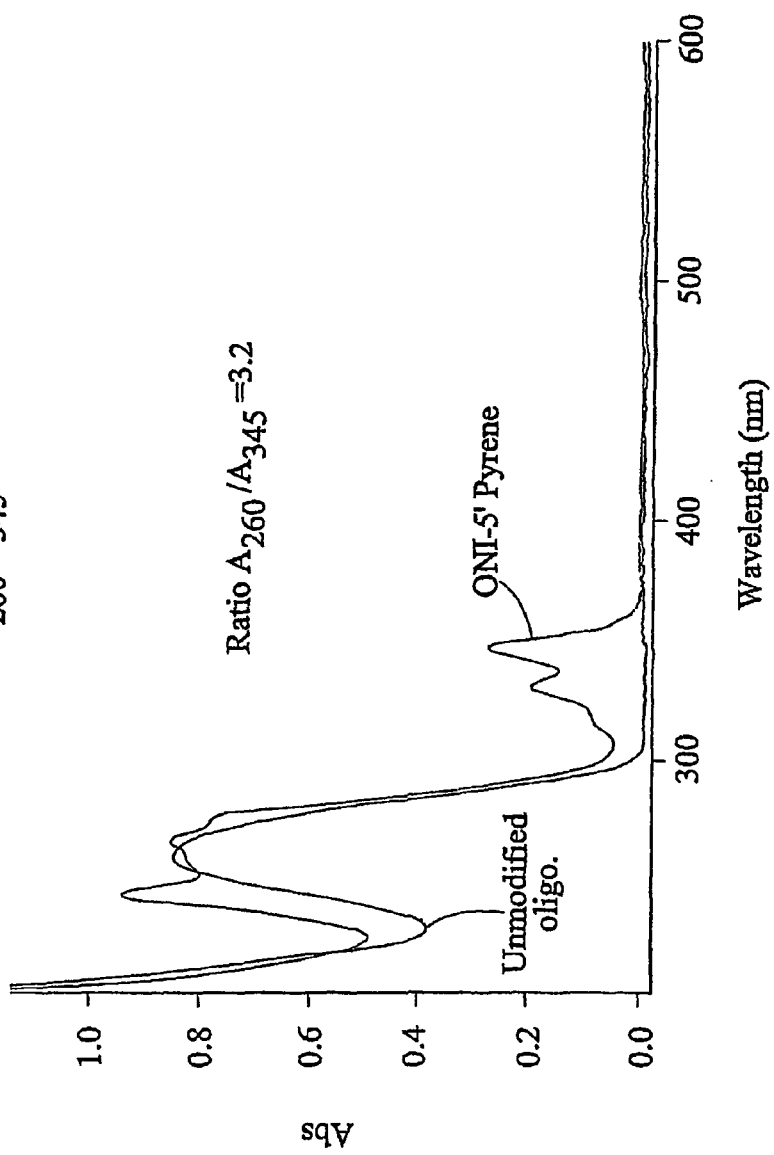
FIG. 27 illustrates the UV/visible absorption spectra of unmodified ON1 (5'pTGTTTGGC) and ON1-5'pyrene in 50% v/vacetonitrile.

1-Pyrenemethylamine was attached via a phosphoramidate link to the terminal 5'-phosphate of ON1 (5'pT-GTTTGGC) or to the 3'-phosphate of ON2 (CGATTCTG3'p). In order to do this the cetyltrimethylammonium salt of the oligonucleotides (2 mg for ON1 and 2.4 mg for ON2, 1 μmol) was prepared by addition of 4% aqueous cetyltrimethylammonium bromide (100 μl, 10 μl×10) to a solution of the lithium salt of the oligonucleotide (1 μmol) in 200 μl of water, with centrifugation on each addition, until no more precipitation was observed. The supernatant was removed and the precipitate dried in vacuo overnight. The cetyltrimethylammonium salt of the oligonucleotide (~1 μmol) was dissolved in DMF (200 μl), triphenylphosphine (12 mg, 50 μmol) and 2',2'-dipyridyl disulfide (11 mg, 50 μmol) added, and the reaction mixtures incubated at 37° C. for 10 min. 4-N',N'-Dimethylaminopyridine (6 mg, 50 μmol) was added and the reaction mixture incubated for a further 10 minutes at 37° C. To the oligonucleotide reaction mixture 1-pyrenemethylamine hydrochloride (4 mg dissolved in 100 μl of DMF and 3 μl triethylamine) was added and the reaction mixtures were incubated at 37° C. for 6 hours. After this time the reaction mixture was split into 2 tubes and the oligonucleotide were precipitated by 2% LiClO$_4$ in acetone (2 ml). After centrifugation the supernatant was carefully removed and the precipitate redissolved in water (180 μl) and centrifuged to remove any activating agents still present the supernatant was removed and the modified oligo reprecipitated in 2% LiClO$_4$ in acetone. The oligonucleotide conjugate was then separated from unreacted precursors by reversed-phase HPLC (eluted by an aqueous solution of 0.05 M LiClO$_4$ with an increasing gradient of acetonitrile from 0 to 40%). Products were characterised initially by UV/visible spectroscopy. Yields were typically around 80%. The absorbance spectra of unmodified ON1 and ON1-5'Pyrene are shown in FIG. 27. The absorbance around 345 nm is due to the presence of pyrene, which also alters the absorbance band at 260 nm. The ratio between the absorption bands at 260 and 345 nm is around 3.5, typical of mono-pyrene-substituted 8-mer oligos (if bis-pyrenylation occurs the $A_{260}$:$A_{345}$ ratio is typically 2. Appropriate fractions were combined and lyophilised and the oligos were characterised by $^1$H NMR spectroscopy in $D_2O$.

Figure 28:
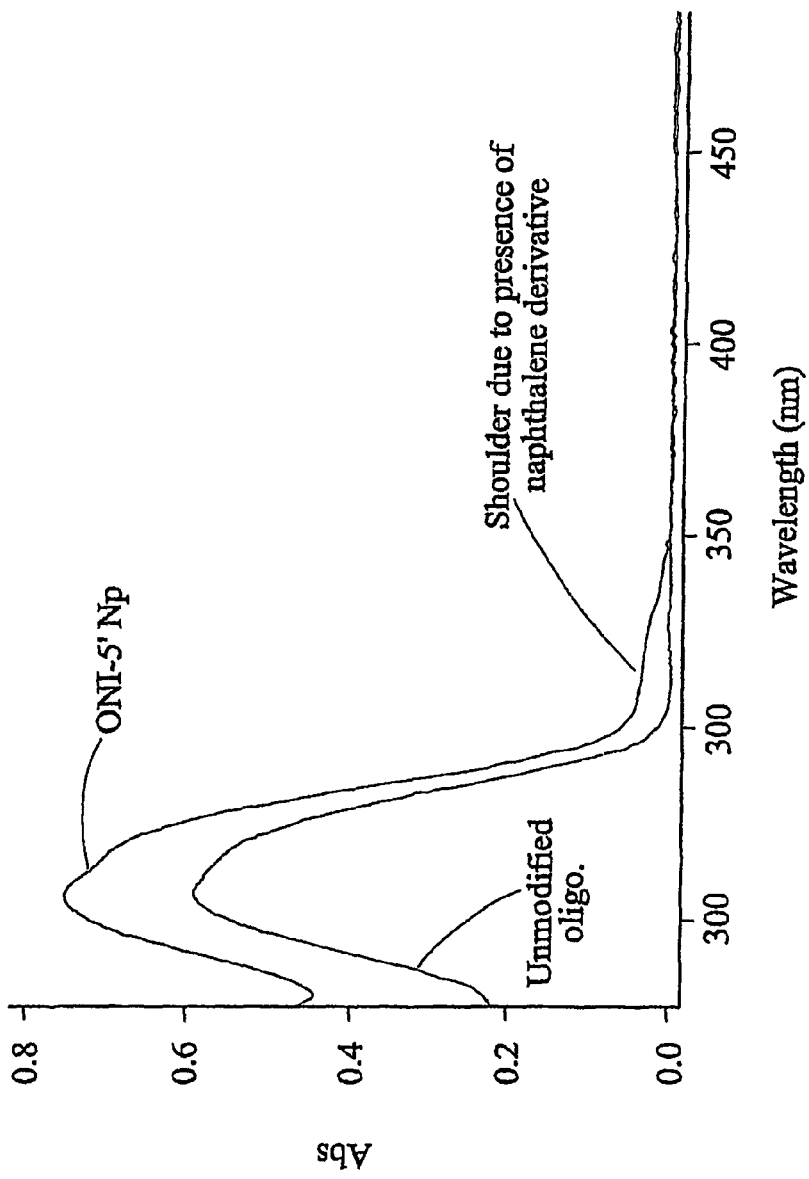
FIG. 28 illustrates the UV/visible absorption spectra of unmodified ON1 (5'pTGTTTGGC) and ON1-5' Np in 50% v/vacetonitrile.

3.3.2 Attachment of N'-methyl-N'-naphthalen-1-yl-ethane-1,2-diamine to oligonucleotide probes N'-methyl-N'-naphthalen-1-yl-ethane-1,2-diamine was attached via a phosphoramidate link to the terminal 5'-phosphate of ON1 (5'pTGTTTGGC) and the 3'-phosphate of ON2 (CGATTCTG3'p) by the procedure described, but using N'-methyl-N'-naphthalen-1-yl-ethane-1,2-diamine dihydrochloride (2 mg, 7.3 μmol dissolved in 100 μl of DMF and 3 μl triethylamine). The product was purified by reverse-phase HPLC (eluted by 0.5 M LiClO$_4$ with a gradient from 0 to 40% acetonitrile). Products were identified by UV/visible spectroscopy and appropriate fractions were lyophilised. Typical yields were around 80%. The UV/visible absorption spectra of unmodified ON1 and ON1-5'Np are shown in FIG. 28. The shoulder at 310 nm on the 260 nm absorption band indicates the presence of naphthalene.

Bis-attachment of N'-Methyl-N'-naphthalen-1-yl-ethane-1,2-diamine dihydrochloride to oligonucleotide probes.

Two equivalents of N'-methyl-N'-naphthalen-1-yl-ethane-1,2-diamine dihydrochloride were attached via phosphoramidate links to the terminal 5'-phosphate of ON1 (5'pT-GTTTGGC) or to the 3'-phosphate of ON2 (CGATTCTG3'p) to the cetyltrimethylammonium salts of the oligonucleotides (~1 μmol) dissolved in DMF (200 μl) were added triphenylphosphine (80 mg, 300 μmol) and 2',2'-dipyridyl disulfide (70 mg, 318 μmol), and the reaction mixture incubated at 37° C. for 10 min. 4-N',N'-Dimethylaminopyridine (40 mg, 329 μmol) was then added and the reaction mixture incubated for a further 10 minutes at 37° C. N'-Methyl-N'-naphthalen-1-yl-ethane-1,2-diamine dihydrochloride (4 mg, 14.6 μmol, dissolved in 100 μl of DMF and 3 μl triethylamine) was added. The reaction mixture was incubated at 50° C. for 24 hours, precipitated as described above and purified using reverse-phase HPLC (eluted by an aqueous solution of 0.05 M LiClO$_4$ with a gradient from 0 to 60% acetonitrile). Products were identified by UV/visible spectroscopy and appropriate fractions were lyophilised.

The invention claimed is:

1. A method of analysing a sample to determine the presence or otherwise therein of a target polynucleotide sequence, the method comprising the steps of
   (a) treating the sample under hybridising conditions with
      (i) a first polynucleotide probe labelled with a first exciplex partner moiety able on photoirradiation to form an exciplex with a second exciplex partner moiety, and
      (ii) a second polynucleotide probe labelled with the second exciplex partner moiety, said first and second probes being adapted to bind to mutually exclusive regions of said target sequence such that said moieties are able to form said exciplex which is detectably different from the first and second moieties,
   (b) effecting photoirradiation to cause exciplex formation, and
   (c) detecting for formation of the exciplex to determine the presence or otherwise of the target polynucleotide sequence
      wherein the sample when irradiated contains an organic solvent selected from 2,2,2-trifluoroethanol, ethylene glycol or ethylene glycol dimethyl ether.

2. The method as claimed in claim 1 wherein the sample on photoirradiation comprises an admixture of water or buffer and the solvent.

3. The method as claimed in claim 1 wherein the sample on photoirradiation comprises more than 30% by volume of the solvent.

4. The method as claimed in claim 3 wherein the sample of photoirradiation comprises more than 40% by volume of the solvent.

5. The method as claimed in claim 4 wherein the sample on photoirradiation comprises more than 50% by volume of the solvent.

6. The method as claimed in claim 5 wherein on photoirradiation the sample comprises at least 70% by volume of the solvent.

7. The method as claimed in claim 3 wherein on photoirradiation the sample comprises a maximum of 80% by volume of the solvent.

8. The method as claimed in claim 1 wherein the solvent is 2,2,2-trifluorethanol.

9. The method as claimed in claim 1 in which, prior to step (a) the sample is heated to destroy any secondary structure.

10. The method as claimed in claim 1 wherein after step (a) the sample is heated and then cooled prior to exciplex formation and detection.

11. The method as claimed in claim 10 wherein said heating after step (a) is to a temperature at which the probes, if hybridised to a target polynucleotide sequence, are denatured from the target sequence.

12. The method as claimed in claim 10 wherein said heating after step (a) is to a temperature not exceeding 90° C.

13. The method as claimed in claim 12 wherein said heating after step (a) is to a temperature not exceeding 70° C.

14. The method as claimed in claim 13 wherein said heating after step (a) is to a temperature not exceeding 60° C.

15. The method as claimed in claim 14 wherein said heating after step (a) is to a temperature not exceeding 50° C.

16. The method as claimed in claim 15 wherein said heating after step (a) is to a temperature not exceeding 40° C.

17. The method as claimed in claim 1 wherein the first polynucleotide probe is labelled at its 5' end with the first exciplex partner moiety.

18. The method as claimed in claim 1 wherein the second polynucleotide probe is labelled at its 3'-end with the second exciplex partner moiety.

19. The method as claimed in claim 1 wherein the first and second exciplex partner moieties are bonded to the first and second polynucleotide probes respectively by linkers.

20. The method as claimed in claim 1 wherein the exciplex forming partner moieties comprise a pyrenyl group as the first partner and the second partner comprises at least one aromatic ring.

21. The method as claimed in claim 20 wherein the second partner is a fused ring system.

22. The method as claimed in claim 21 wherein the second partner is provided with at least one electron donating group.

23. The method as claimed in claim 18 wherein one of the probes has attached thereto a 1-pyrenyl-methylamino group and the other probe has attached thereto either a 2-(N'-methyl-N'-naphthalen-1'ylamino)ethylamino group or a 2-(N'-naphthalen-1'-ylamino)ethylamino (MMN) group, said groups providing the exciplex partner moieties.

24. The method as claimed in claim 19 wherein the combination of one of the exciplex partner moieties and its associated linker group is a 2-(N'-methyl-N'-naphth-1"-ylamino)ethylamino group and the combination of the other exciplex partner moiety and its associated linker group is a pyren-1-yl-methylamino group.

25. The method as claimed in claim 1 wherein the first and second polynucleotide probes bind to the target polynucleotide sequence with the 3' end of one probe being proximal to the 5' end of the other probe such that there is one to three bases of the target polynucleotide sequence between the proximal 3' and 5' ends of the probes as bound to the target polynucleotide sequence.

26. The method as claimed in claim 1 wherein at least one of the probes has at least one base mismatch as compared to the target polynucleotide sequence.

27. The method as claimed in claim 26 wherein at least one of the probes has one or two base mismatches as compared to the target polynucleotides sequence.

28. The method as claimed in claim 1 wherein the target polynucleotide sequence comprises DNA.

29. The method as claimed in claim 1 wherein the target polynucleotide sequence comprises a natural nucleic acid and/or an analogue or derivative of such a nucleic acid.

30. The method as claimed in claim 29 wherein the target nucleotide sequence comprises a nucleic acid analogue, and wherein said analogue is PNA or LNA.

31. The method as claimed in claim 1 wherein the target polynucleotide sequence comprises RNA.

32. The method as claimed in claim 31 wherein the first and second probes are DNA probes.

33. The method as claimed in claim 1 wherein the probes are DNA, RNA or analogues or derivatives of a nucleic acid.

34. The method as claimed in claim 33 wherein the probes comprise LNA or PNA.

35. The method as claimed in claim 1 wherein the probes contain a mixture of at least two of DNA, RNA and analogues or derivatives of nucleic acid in their sequence.

36. The method as claimed in claim 1 wherein the target polynucleotide sequence and the first and second polynucleotide probes are free in solution.

37. The method as claimed in claim 1 wherein at least one of the target polynucleotide sequence and/or at least one of the probes is immobilised with there being also at least one of the target polynucleotide sequence and/or at least one of the probes being free in solution.

38. The method as claimed in claim 37 wherein immobilisation is on a solid substrate.

39. The method as claimed in claim 38 wherein immobilisation is on a chip, microarray, a nanoparticle or other surface.

40. The method as claimed in claim 12 wherein said heating after step (a) is to a temperature not exceeding 80° C.

* * * * *